(12) United States Patent
Alvarez et al.

(10) Patent No.: US 10,023,623 B2
(45) Date of Patent: *Jul. 17, 2018

(54) FUSION POLYPEPTIDES COMPRISING AN ACTIVE PROTEIN LINKED TO A MUCIN-DOMAIN POLYPEPTIDE

(71) Applicant: Alkermes, Inc., Waltham, MA (US)

(72) Inventors: Juan Alvarez, Chelmsford, MA (US); Jean Chamoun, Waltham, MA (US); Heather C. Losey, Lexington, MA (US)

(73) Assignee: Alkermes, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/841,809

(22) Filed: Sep. 1, 2015

(65) Prior Publication Data

US 2016/0052983 A1   Feb. 25, 2016

Related U.S. Application Data

(63) Continuation of application No. 13/911,818, filed on Jun. 6, 2013, now Pat. No. 9,156,897.

(60) Provisional application No. 61/778,575, filed on Mar. 13, 2013, provisional application No. 61/723,081, filed on Nov. 6, 2012, provisional application No. 61/657,378, filed on Jun. 8, 2012, provisional application No. 61/657,264, filed on Jun. 8, 2012, provisional application No. 61/657,285, filed on Jun. 8, 2012.

(51) Int. Cl.

| C07K 14/47 | (2006.01) |
|---|---|
| C07K 14/54 | (2006.01) |
| C07K 14/55 | (2006.01) |
| C07K 14/545 | (2006.01) |
| C07K 14/715 | (2006.01) |
| C07K 14/50 | (2006.01) |
| C07K 14/705 | (2006.01) |
| C07K 14/71 | (2006.01) |
| C07K 14/575 | (2006.01) |
| A61K 38/00 | (2006.01) |
| A61K 39/00 | (2006.01) |

(52) U.S. Cl.
CPC .......... *C07K 14/55* (2013.01); *C07K 14/4713* (2013.01); *C07K 14/4727* (2013.01); *C07K 14/50* (2013.01); *C07K 14/54* (2013.01); *C07K 14/545* (2013.01); *C07K 14/5412* (2013.01); *C07K 14/5443* (2013.01); *C07K 14/57563* (2013.01); *C07K 14/70503* (2013.01); *C07K 14/71* (2013.01); *C07K 14/7155* (2013.01); *A61K 38/00* (2013.01); *A61K 2039/505* (2013.01); *C07K 2319/00* (2013.01); *C07K 2319/02* (2013.01); *C07K 2319/30* (2013.01); *C07K 2319/31* (2013.01); *C07K 2319/74* (2013.01); *C07K 2319/91* (2013.01)

(58) Field of Classification Search
CPC .............. A61K 2039/505; A61K 38/00; C07K 14/4713; C07K 14/4727; C07K 14/50; C07K 14/54; C07K 14/5412; C07K 14/5443; C07K 14/545; C07K 14/55; C07K 14/57563; C07K 14/70503; C07K 14/71; C07K 14/7155

See application file for complete search history.

(56) References Cited

U.S. PATENT DOCUMENTS

| 2005/0260222 | A1 | 11/2005 | Gupta et al. |
| 2005/0265995 | A1 | 12/2005 | Tomlinson et al. |
| 2008/0286211 | A1* | 11/2008 | Barker ................ A61K 9/0031 424/45 |

FOREIGN PATENT DOCUMENTS

| JP | 2010536341 A | 12/2010 | |
| WO | 199946392 A1 | 9/1999 | |
| WO | 2005034863 A2 | 4/2005 | |
| WO | 2007020889 A1 | 2/2007 | |
| WO | 2007062844 A1 | 6/2007 | |
| WO | 2007063907 A1 | 6/2007 | |
| WO | WO 2007062844 A1 * | 6/2007 | ......... C07K 14/4727 |
| WO | 2009153960 A1 | 12/2009 | |
| WO | 2010091122 A1 | 8/2010 | |

OTHER PUBLICATIONS

Hasanain Shikari, Effect of Topical IL-1RA on Signs and Symptoms of Dry Eye Disease in Patients With Ocular Graft-versus-host Disease (GVHD), ARVO Annual meeting, Abstract, Mar. 2012, vol. 53, 579.*
Uniprot Protein Database, Protein Accession Q8N3074, Human Mucin 20, accessed on Oct. 16, 2016.*
Nomellini, J.F., et al., "S-Layer-Mediated Display of the Immunoglobulin G-Binding Domain of Streptococcal Protein G on the Surface of Caulobacter crescentus: Development of an Immunoactive Reagent," Applied and Environmental Microbiology, 73(10): pp. 3245-3253 (Mar. 2007).

(Continued)

*Primary Examiner* — Hasan S Ahmed
*Assistant Examiner* — Erinne R Dabkowski
(74) *Attorney, Agent, or Firm* — Elmore Patent Law Group, P.C.; Darlene Vanstone; Carolyn Elmore

(57) ABSTRACT

The present invention provides fusion proteins comprising a mucin-domain polypeptide covalently linked to an active protein that has improved properties (e.g. pharmacokinetic and/or physicochemical properties) compared to the same active protein not linked to mucin-domain polypeptide, as well as methods for making and using the fusion proteins of the invention.

2 Claims, 21 Drawing Sheets

(56) References Cited

OTHER PUBLICATIONS

Fontenot, D., et al., "Human Immunodeficiency Virus (HIV) antigens: Structure and Serology of Multivalent Human Mucin MUC1-HIV V3 Chimeric Proteins," Proc. Natl. Acad. Sci. USA, vol. 92, pp. 315-319 (Jan. 1995).
Shen, H., et al., "Deletion of the Linker Connecting the Catalytic and Cellulose-Binding Domains of Endoglucanase A (CENA) of Cellulomonas fimi Alters Its Conformation and Catalytic Activity," The Journal of Biological Chemistry, 266 (17): pp. 11335-11340 (1991).
Chen, X., et al., "Fusion Protein Linkers: Property, Design and Functionality," Advanced Drug Delivery Reviews 65 (10): pp. 1357-1369 (2012).

* cited by examiner

FUSION POLYPEPTIDES COMPRISING AN ACTIVE PROTEIN LINKED TO A MUCIN-DOMAIN POLYPEPTIDE

RELATED APPLICATION(S)

This application is a continuation of U.S. application Ser. No. 13/911,818, filed Jun. 6, 2013 which claims the benefit of U.S. Provisional Application Nos. 61/657,264, filed on Jun. 8, 2012; 61/778,575, filed Mar. 13, 2013; 61/657,378, filed Jun. 8, 2012; 61/723,081, filed Nov. 6, 2012; 61/657,285, filed Jun. 8, 2012 and 61/778,812, filed Mar. 13, 2013. The entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on May 31, 2013, is named 4000.3058WO_SL.txt and is 27,431 bytes in size.

BACKGROUND OF THE INVENTION

The pharmacokinetics, pharmacodistribution, solubility, stability, enhancement of effector function and receptor binding of protein therapeutics can be significantly influenced by the carbohydrate moiety of glycosylated proteins. In addition, many biologically active peptides and proteins have limited solubility, or become aggregated during recombinant productions, requiring complex solubilization and refolding procedures. Furthermore, protein and peptide therapeutics with molecular weights lower than 60 kilodaltons (kD) often suffer from short half-lives due to renal clearance.

Current strategies employed to extend serum half-life of protein therapeutics primarily fall within two general categories: 1) utilization of FcRn-mediated recycling and 2) increase of hydrodynamic volume. Specific approaches which have been described include conjugation, binding, or fusion to FcRn-binding proteins or domains (Fc, albumin) for the former strategy, and multimerization, chemical coupling to polymers or carbohydrates (such as PEG, Colominic acid, or Hydroxyethyl starch), incorporation of N-glycosylation sites for the latter. However, the production of Fc-fusion proteins is a time-consuming, inefficient, and expensive process that requires additional manufacturing steps and often complex purification procedures. In addition, chemical coupling strategies, PEGylation being the most widely used, result in significant increases in production costs due to the addition of conjugation and purification steps and reduced overall yields. Recently, other recombinant PEG mimetics produced through fusion of a long, flexible polypeptide sequence, such as those described in U.S. 2010/0239554 A1, have also been described. Although this technology circumvents the additional conjugation step, the added peptide sequence, being non-endogenous, has the potential for immunogenicity.

Mucin proteins and mucin-domains of proteins contain a high degree of glycosylation which structurally allows mucin proteins and other polypeptides comprising mucin domains to behave as stiffened random coils. This stiffened random coiled structure in combination with the hydrophilic branched hydrophilic carbohydrates that make up the heavily glycosylated mucin domains is particularly useful in for increasing the hydrodynamic radius of the active protein beyond what would be expected based on the molecular weight of the expressed protein. Also because of the high level of glycosylation, addition of a mucin domain has the potential to modify the physicochemical properties of a protein such as charge, solubility and viscoelastic properties of concentrated solutions of the active protein.

The fusion protein compositions and methods of the present invention improve the biological, pharmacological, safety, and/or pharmaceutical properties of an active protein.

SUMMARY OF THE INVENTION

The present invention provides fusion proteins comprising a mucin-domain polypeptide covalently linked to an active protein that has improved properties (e.g. pharmacokinetic and/or physicochemical properties) compared to the same active protein not linked to mucin-domain polypeptide, as well as methods for making and using the fusion proteins of the invention.

In one embodiment the invention provides a fusion protein comprising a mucin-domain polypeptide linked to an active protein wherein at least one pharmacokinetic or physicochemical property of the active protein is improved as compared to the corresponding active protein that is not fused to the mucin-domain polypeptide.

In one embodiment the invention provides nucleic acid sequences encoding the fusion protein of the invention as well as vectors and host cells for expressing the nucleic acids of the invention.

In one embodiment the invention provides methods for extending the serum half life of a therapeutic active protein.

In one embodiment the invention provides improving the solubility of a therapeutic active protein.

In one embodiment the invention provides pharmaceutical compositions comprising the fusion proteins of the invention.

In one embodiment, the invention provides methods of treating diseases, conditions and disorders in subject in need of treatment using the pharmaceutical compositions of the invention.

DETAILED DESCRIPTION OF THE INVENTION

Figure 1:
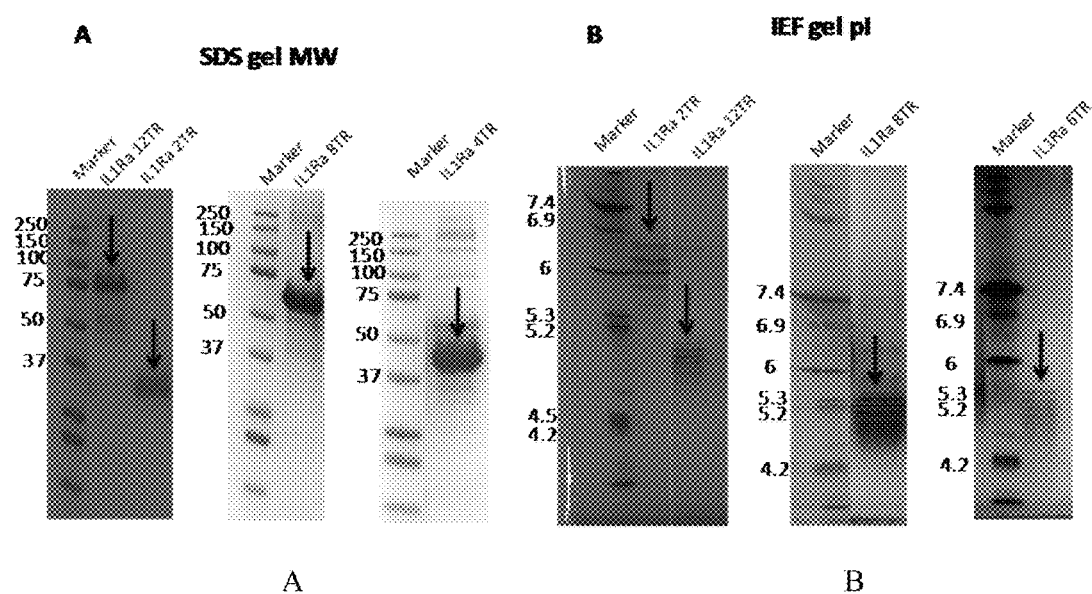
FIG. 1. Coomassie Blue-stained SDS/polyacrylamide gel (A) and IEF gel (B) of IL1Ra mucin constructs. Arrows indicate the proteins of interest. Multiplicity of bands of in IEF gel indicate differentially charged species, most likely due to differences in N-glycosylation.
Figure 2:
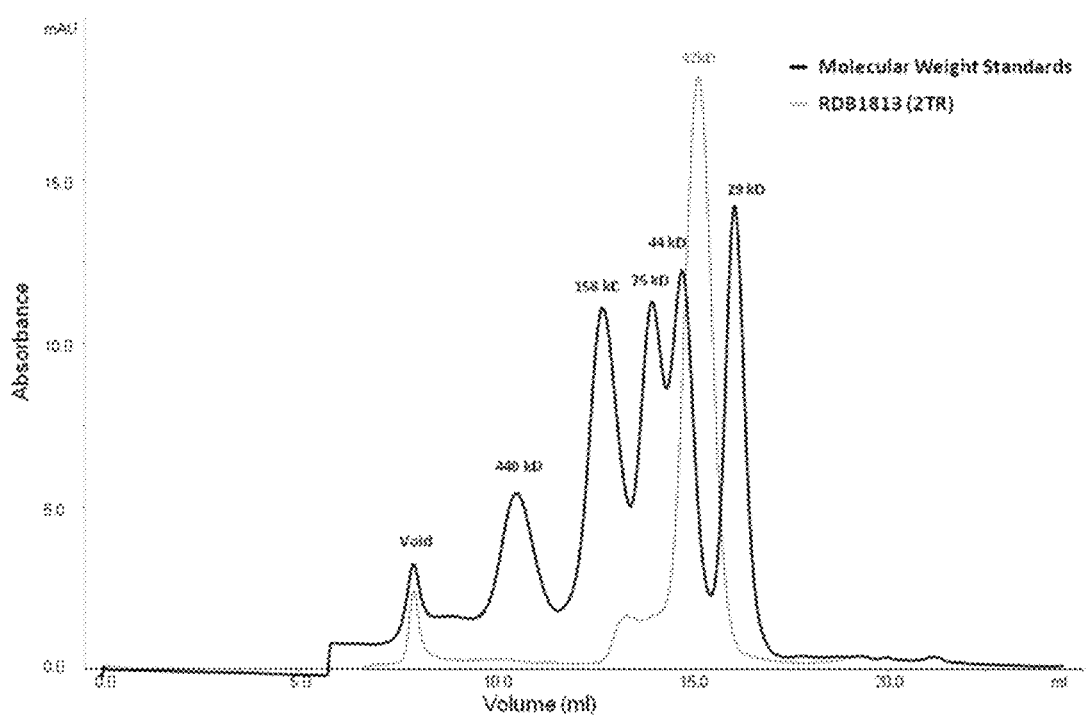
FIG. 2. Gel filtration chromatogram of RDB1813 (grey) and molecular size standards (black). Molecular weights of the standards and apparent molecular weight of RDB1813 are listed above each eluting peak.
Figure 3:
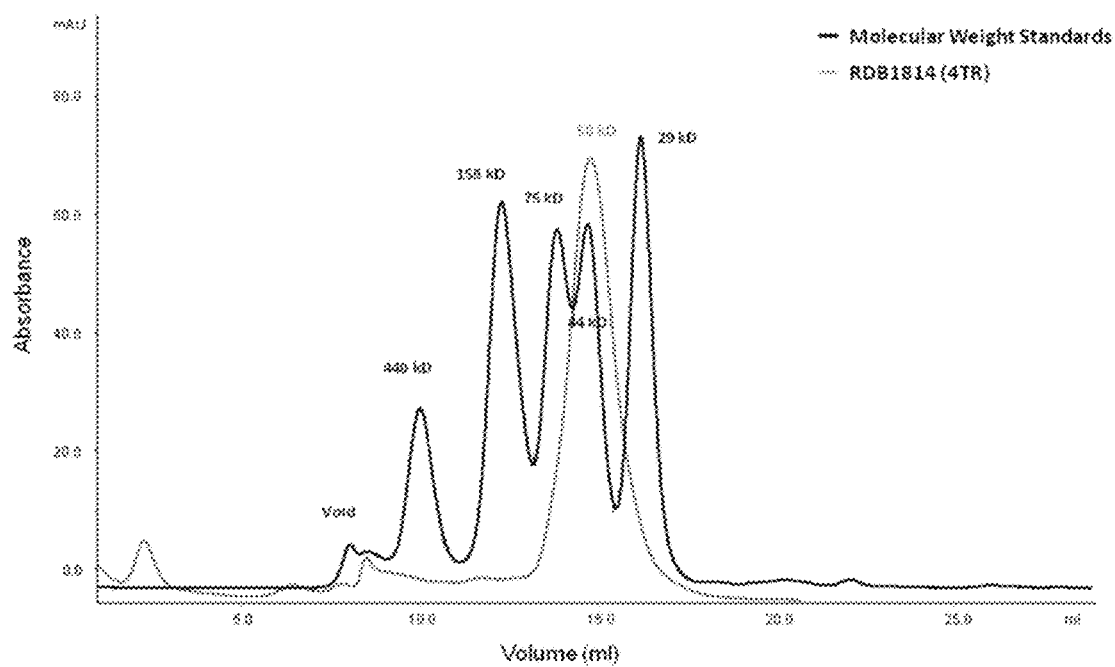
FIG. 3. Gel filtration chromatogram of RDB1814 (grey) and molecular size standards (black). Molecular weights of the standards and apparent molecular weight of RDB1814 are listed above each eluting peak.
Figure 4:
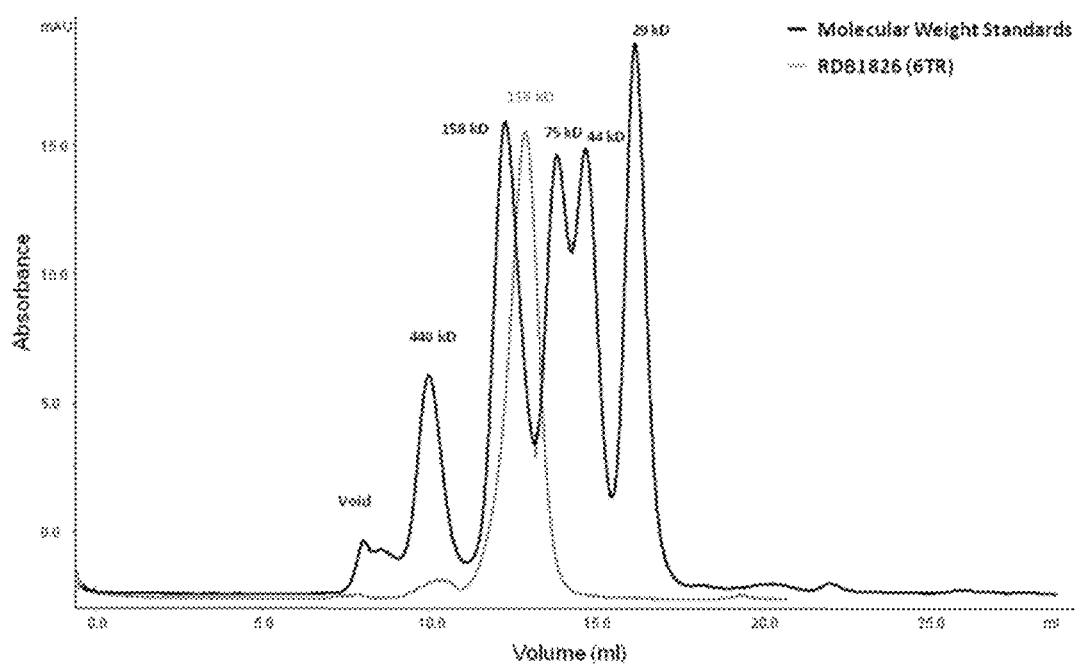
FIG. 4. Gel filtration chromatogram of RDB1826 (grey) and molecular size standards (black). Molecular weights of the standards and apparent molecular weight of RDB1826 are listed above each eluting peak.
Figure 5:
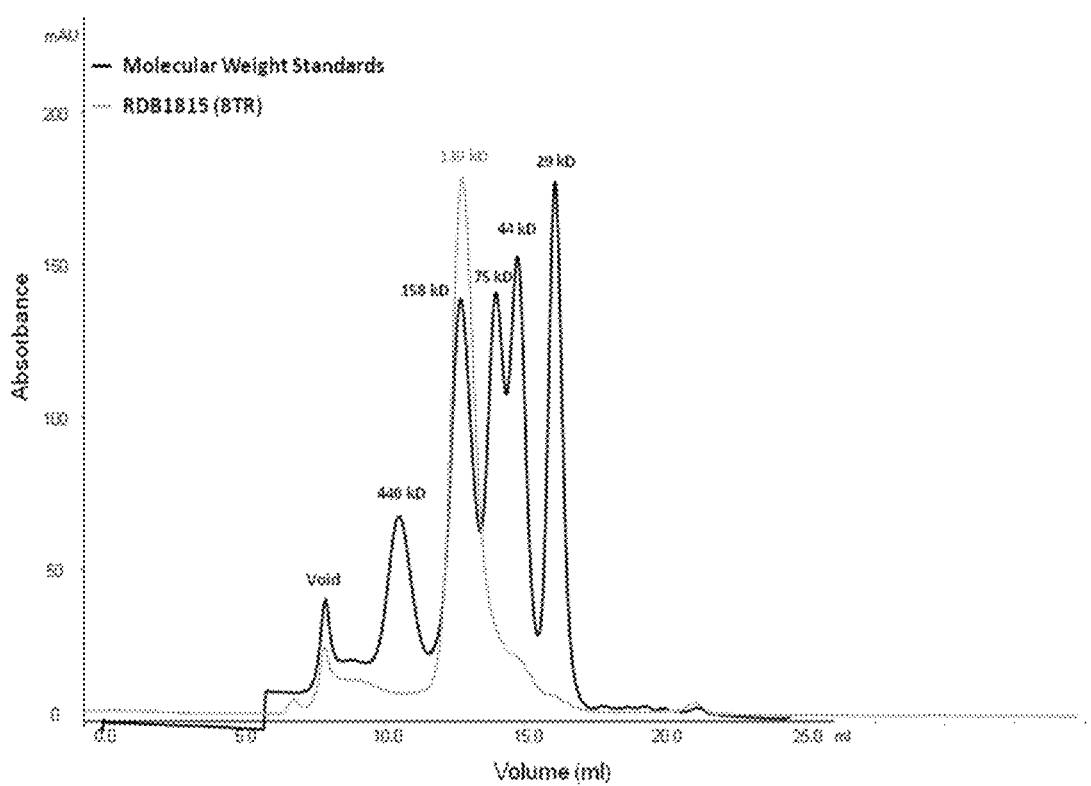
FIG. 5. Gel filtration chromatogram of RDB1815 (grey) and molecular size standards (black). Molecular weights of the standards and apparent molecular weight of RDB1815 are listed above each eluting peak.
Figure 6:
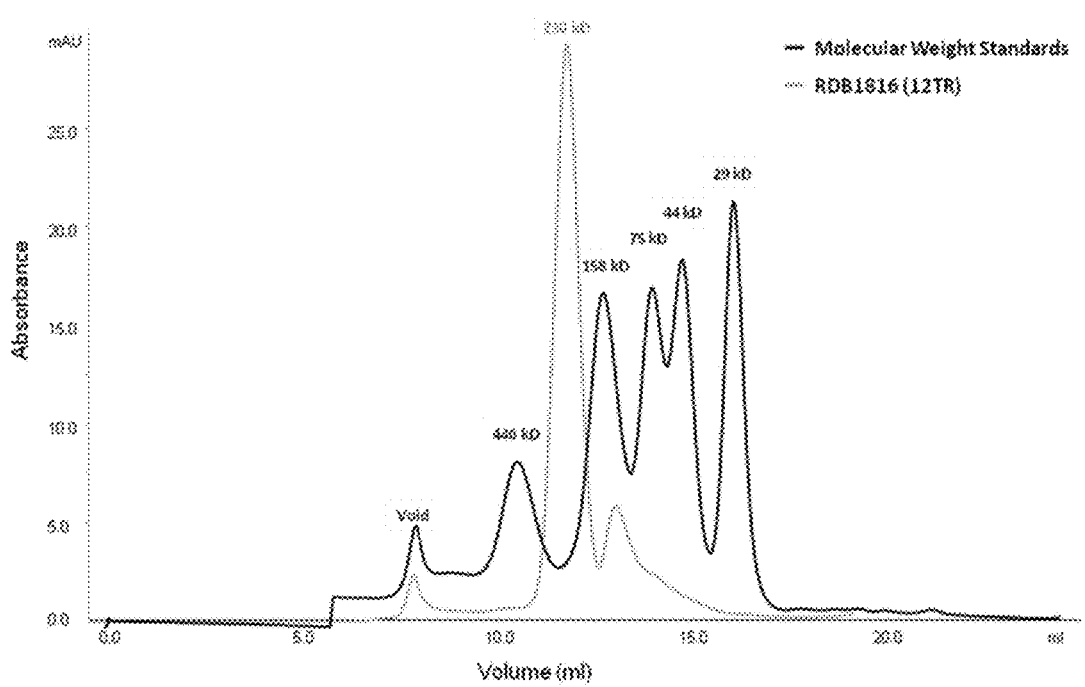
FIG. 6. Gel filtration chromatogram of RDB1816 (grey) and molecular size standards (black). Molecular weights of the standards and apparent molecular weight of RDB1816 are listed above each eluting peak.

A description of preferred embodiments of the invention follows.

Definitions

As used herein, the following terms have the meanings ascribed to them unless specified otherwise.

As used in the specification and claims, the singular forms "a", "an" and "the" include plural references unless the context clearly dictates otherwise. For example, the term "a cell" includes a plurality of cells, including mixtures thereof.

The terms "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component.

As used herein the term "amino acid" refers to either natural and/or unnatural or synthetic amino acids, including but not limited to glycine and both the D or L optical isomers, and amino acid analogs and peptidomimetics. Standard single or three letter codes are used to designate amino acids.

The term "non-naturally occurring," as applied to sequences and as used herein, means polypeptide or polynucleotide sequences that do not have a counterpart to, are not complementary to, or do not have a high degree of homology with a wild-type or naturally-occurring sequence found in a mammal. For example, a non-naturally occurring polypeptide may share no more than 99%, 98%, 95%, 90%, 80%, 70%, 60%, 50% or even less amino acid sequence identity as compared to a natural sequence when suitably aligned.

The terms "glycosylation" and "glycosylated" are used interchangeably herein to mean the carbohydrate portion of a protein or the process by which sugars are post-translationally attached to proteins during their production in cells to form glyco-proteins. Glycosylation of proteins is a post-translational event and refers to the attachment of glycans to serine and threonine and, to a lesser extent to hydroxyproline and hydroxylysine in the case of O-linked glycosylation, or asparagine, in the case of N-linked glycosylation.

A "fragment" is a truncated form of a native active protein that retains at least a portion of the therapeutic and/or biological activity. A "variant" is a protein with sequence homology to the native active protein that retains at least a portion of the therapeutic and/or biological activity of the active protein. For example, a variant protein may share at least 70%, 75%, 80%, 85%, 90%, 95%, 96%, 97%, 98% or 99% amino acid sequence identity with the reference active protein. As used herein, the term "active protein moiety" includes proteins modified deliberately, as for example, by site directed mutagenesis, insertions, or accidentally through mutations.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is generally greater than that of its naturally occurring counterpart. In general, a polypeptide made by recombinant means and expressed in a host cell is considered to be "isolated."

An "isolated" polynucleotide or polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal or extra-chromosomal location different from that of natural cells.

"Conjugated", "linked," "fused," and "fusion" are used interchangeably herein. These terms refer to the joining together of two more chemical elements or components, by whatever means including chemical conjugation or recombinant means. For example, a promoter or enhancer is operably linked to a coding sequence if it affects the transcription of the sequence. Generally, "operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature).

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide that is known to comprise additional residues in one or both directions.

"Heterologous" means derived from a genotypically distinct entity from the rest of the entity to which it is being compared. For example, a glycine rich sequence removed from its native coding sequence and operatively linked to a coding sequence other than the native sequence is a heterologous glycine rich sequence. The term "heterologous" as applied to a polynucleotide, a polypeptide, means that the polynucleotide or polypeptide is derived from a genotypically distinct entity from that of the rest of the entity to which it is being compared.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components.

"Recombinant" as applied to a polynucleotide means that the polynucleotide is the product of various combinations of in vitro cloning, restriction and/or ligation steps, and other procedures that result in a construct that can potentially be expressed in a host cell.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

"Homology" or "homologous" refers to sequence similarity or interchangeability between two or more polynucleotide sequences or two or more polypeptide sequences. When using a program such as BestFit to determine sequence identity, similarity or homology between two different amino acid sequences, the default settings may be used, or an appropriate scoring matrix, such as blosum45 or blosum80, may be selected to optimize identity, similarity or homology scores. Preferably, polynucleotides that are homologous are those which hybridize under stringent conditions as defined herein and have at least 70%, preferably at least 80%, more preferably at least 90%, more preferably 95%, more preferably 97%, more preferably 98%, and even more preferably 99% sequence identity to those sequences.

The terms "stringent conditions" or "stringent hybridization conditions" includes reference to conditions under which a polynucleotide will hybridize to its target sequence, to a detectably greater degree than other sequences (e.g., at least 2-fold over background). Generally, stringency of hybridization is expressed, in part, with reference to the temperature and salt concentration under which the wash step is carried out. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short polynucleotides (e.g., 10 to 50 nucleotides) and at least about 60° C. for long polynucleotides (e.g., greater than 50 nucleotides) for example, "stringent conditions" can include hybridization in 50% formamide, 1 M NaCl, 1% SDS at 37° C., and three washes for 15 min each in 0.1×SSC/1% SDS at 60 to 65° C. Alternatively, temperatures of about 65° C., 60° C., 55° C., or 42° C. may be used. SSC concentration may be varied from about 0.1 to 2×SSC, with SDS being present at about 0.1%. Such wash temperatures are typically selected to be about 5° C. to 20° C. lower than the thermal melting point for the specific sequence at a defined ionic strength and pH. The Tm is the temperature (under defined ionic strength and pH) at which 50% of the target sequence hybridizes to a perfectly matched probe. An equation for calculating Tm and conditions for nucleic acid hybridization are well known and can be found in Sambrook, J. et al. (1989) *Molecular Cloning: A Laboratory Manual*, 2$^{nd}$ ed., Vol. 1-3, Cold Spring Harbor Press, Plainview N.Y.; specifically see Volume 2 and Chapter 9. Typically, blocking reagents are used to block non-specific hybridization. Such blocking reagents include, for instance, sheared and denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined polynucleotide sequence, for example, as defined by a particular SEQ ID number, or may be measured over a shorter length, for example, over the length of a fragment taken from a larger, defined polynucleotide sequence, for instance, a fragment of at least 45, at least 60, at least 90, at least 120, at least 150, at least 210 or at least 450 contiguous residues. Such lengths are exemplary only, and it is understood that any fragment length supported by the sequences shown herein, in the Tables, Figures or Sequence Listing, may be used to describe a length over which percentage identity may be measured.

"Percent (%) amino acid sequence identity," with respect to the polypeptide sequences identified herein, is defined as the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

Those skilled in the art can determine appropriate parameters for measuring alignment, including any algorithms needed to achieve maximal alignment over the full length of the sequences being compared. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the Tables, Figures or Sequence Listing, may be used to describe a length over which percentage identity may be measured.

A "vector" is a nucleic acid molecule, preferably self-replicating in an appropriate host, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

"Degradation resistance," as applied to a polypeptide, refers to the ability of the polypeptides to withstand degradation in blood or components thereof, which typically involves proteases in the serum or plasma, or within a formulation intended as a storage or delivery vehicle for a protein. The degradation resistance can be measured by combining the protein with human (or mouse, rat, monkey, as appropriate) blood, serum, plasma, or a formulation, typically for a range of days (e.g. 0.25, 0.5, 1, 2, 4, 8, 16 days), at specified temperatures such as −80° C., −20° C., 0° C., 4° C., 25° C., and 37° C. The intact protein in the samples is then measured using standard protein quantitation techniques. The time point where 50% of the protein is degraded is the "degradation half-life" of the protein.

The term "half-life" typically refers to the time required for the plasma concentration of a drug to be reduced by one-half. The terms "half-life", "$t_{1/2}$", "elimination half-life" and "circulating half-life" are used interchangeably herein.

The "hydrodynamic radius" is the apparent radius ($R_h$ in nm) of a molecule in a solution calculated from diffusional properties. The "hydrodynamic radius" of a protein affects its rate of diffusion in aqueous solution as well as its ability to migrate in gels of macromolecules. The hydrodynamic radius of a protein is influenced by its molecular weight as well as by its structure, including shape and compactness, and its hydration state. Methods for determining the hydrodynamic radius are well known in the art, such as by the use of DLS and size exclusion chromatography. Most proteins have globular structure, which is the most compact three-dimensional structure a protein can have with the smallest hydrodynamic radius. Some proteins adopt a random and open, unstructured, or 'linear' conformation and as a result have a much larger hydrodynamic radius compared to typical globular proteins of similar molecular weight.

"Physiological conditions" refer to a set of conditions in a living host as well as in vitro conditions, including temperature, salt concentration, pH, that mimic those conditions of a living subject. A host of physiologically relevant conditions for use in in vitro assays have been established. Generally, a physiological buffer contains a physiological concentration of salt and is adjusted to a neutral pH ranging from about 6.5 to about 7.8, and preferably from about 7.0 to about 7.5. A variety of physiological buffers is listed in Sambrook et al. (1989). Physiologically relevant temperature ranges from about 25° C. to about 38° C., and preferably from about 35° C. to about 37° C.

"Controlled release agent", "slow release agent", "depot formulation" or "sustained release agent" are used interchangeably to refer to an agent capable of extending the duration of release of a polypeptide of the invention relative to the duration of release when the polypeptide is administered in the absence of agent. Different embodiments of the present invention may have different release rates, resulting in different therapeutic amounts.

The term "antagonist", as used herein, includes any molecule that partially or fully blocks, inhibits, or neutralizes a biological activity of a native polypeptide disclosed herein. Methods for identifying antagonists of a polypeptide may comprise contacting a native polypeptide with a candidate antagonist molecule and measuring a detectable change in one or more biological activities normally associated with the native polypeptide. In the context of the present invention, antagonists may include proteins, nucleic acids, carbohydrates, antibodies or any other molecules that decrease the effect of an active protein.

The term "agonist" is used in the broadest sense and includes any molecule that mimics a biological activity of a native polypeptide disclosed herein. Suitable agonist molecules specifically include agonist antibodies or antibody fragments, fragments or amino acid sequence variants of native polypeptides, peptides, small organic molecules, etc. Methods for identifying agonists of a native polypeptide may comprise contacting a native polypeptide with a candidate agonist molecule and measuring a detectable change in one or more biological activities normally associated with the native polypeptide.

"Activity" for the purposes herein refers to an action or effect of a component of a fusion protein consistent with that of the corresponding native active protein, wherein "biological activity" or "bioactivity" refers to an in vitro or in vivo biological function or effect, including but not limited to receptor binding, antagonist activity, agonist activity, or a cellular or physiologic response.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease in humans or other animals, or to otherwise enhance physical or mental well being of humans or animals, caused by a fusion protein of the invention other than the ability to induce the production of an antibody against an antigenic epitope possessed by the active protein. Determination of a therapeutically effective amount is well within the capability of those skilled in the art, especially in light of the detailed disclosure provided herein.

The terms "therapeutically effective amount" and "therapeutically effective dose", as used herein, refers to an amount of a active protein, either alone or as a part of a fusion protein composition, that is capable of having any detectable, beneficial effect on any symptom, aspect, measured parameter or characteristics of a disease state or condition when administered in one or repeated doses to a subject. Such effect need not be absolute to be beneficial.

The term "therapeutically effective dose regimen", as used herein, refers to a schedule for consecutively administered doses of an active protein, either alone or as a part of a fusion protein composition, wherein the doses are given in therapeutically effective amounts to result in sustained beneficial effect on any symptom, aspect, measured parameter or characteristics of a disease state or condition.

Fusion Proteins

In various aspects the invention provides fusion proteins that comprise a mucin-domain polypeptide linked to an active protein. Such proteins are also referred to herein as "mucinylated" proteins. As used herein, a "fusion protein" of the invention comprises a mucin-domain polypeptide linked to an active protein. In one embodiment the mucin-domain polypeptide and the active protein normally exist in separate proteins and are brought together in the fusion protein; or they may normally exist in the same protein but are placed in a new arrangement in the fusion protein. The compositions and methods of the invention are particularly useful for enhancing the pharmacokinetic properties, such as half-life of an active protein when fused with a mucin-domain polypeptide. In one embodiment the fusion proteins of the invention retain all or a portion of the biologic and/or therapeutic activity of the corresponding active protein not linked to a mucin-domain polypeptide. In one embodiment the therapeutic/biological activity of the active protein is improved when fused with a mucin-domain polypeptide to form a fusion protein of the invention.

In one embodiment, the fusion protein in accordance with the invention specifically excludes immunoglobulin molecules or any molecules containing an Fc domain, or any fragment thereof. In one embodiment, the fusion protein or any portion thereof is not glycosylated by $\alpha 1,3$, galactosyltransferase or $\beta 1,6$-acetylglucosaminyltransferase. In one embodiment, the fusion protein does not bind an antibody specific for $\alpha$Gal. In one embodiment the fusion protein of the invention does not bind a Gal $\alpha 1,3$Gal specific antibody.

Mucin proteins and mucin-domains of proteins contain a high degree of glycosylation which structurally allows mucin proteins and other polypeptides comprising mucin domains to behave as stiffened random coils. This stiffened random coiled structure in combination with the hydrophilic branched hydrophilic carbohydrates that make up the heavily glycosylated mucin domains is particularly useful in for increasing the hydrodynamic radius of the active protein beyond what would be expected based on the molecular weight of the expressed protein. Also because of the high level of glycosylation, addition of a mucin domain also has the potential to modify the physicochemical properties of a protein such as charge, solubility and viscoelastic properties of concentrated solutions of the active protein. Mucinylated fusion proteins of the invention have several advantages over the prior art strategies for extending the half life of proteins. Fusion proteins of the invention may be produced via standard expression means without the need for further conjugation and purification steps. Mucin-domain polypeptides may be linked to the active protein via either the N- or C-terminus of the active protein. Mucin-domain polypeptides are structurally less restrictive than other fusion partners in that they are monomeric, non-globular proteins having reduced bulk and a lowered risk of impact on bioactivity. The use of mucin domains lowers the risk of endogenous bioactivities such as Fc effector functions. When used to prepare human therapeutics, the fusion proteins of the invention may comprise fully human sequences with high glycosylation to reduce the risk of immunogenicity.

The activity of the fusion protein compositions of the invention, including functional characteristics or biologic and pharmacologic activity and parameters that result, may be determined by any suitable screening assay known in the art for measuring the desired characteristic. The activity and structure of the fusion proteins may be measured by assays described herein, assays of the Examples, or by methods known in the art to ascertain the half life, degree of solubility, structure and retention of biologic activity of the compositions of the invention as well as comparisons with active proteins that are not fusion proteins of the invention.

When referring to the fusion protein, the term "linked" or "fused" or "fusion" is intended to indicate that the mucin-domain polypeptide and the active proteins are expressed as a single polypeptide in cells in a manner that allows for 0-linked glycosylation of the mucin-domain polypeptide and maintains the activity of the active protein. In one embodiment the mucin-domain polypeptide may optionally be linked to the active protein via an amino acid linker. The amino acid linker may further optionally comprise a cleavage sequence that may be designed to release the active protein upon administration of the fusion protein to a subject.

Optionally, the fusion protein comprising the active protein fused to the mucin-domain polypeptide may be further fused to one or more additional moieties intended to enhance the activity or impart additional activities to the fusion protein. In one embodiment, the fusion protein comprises the structure: A-M-B, wherein A is an N-terminal fusion partner, M is a mucin domain, and B is a C-terminal fusion partner. A and B may comprise similar and dissimilar identities. In one aspect of this embodiment, A and B are bioactive moieties which can act independently or synergistically in a manner that includes, but is not limited to, agonism, antagonism, enzymatic activity, targeting to specific proteins or cells, chemical reactivity, or oligomerization. In another aspect, when A and B are the same, enhancement of activity is driven through avidity.

A fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *Current Protocols in Molecular Biology*, John Wiley & Sons, 1992). Many expression vectors are commercially available to assist with fusion moieties and will be discussed in more detail below.

Mucin-Domain Polypeptide

A "mucin-domain polypeptide" is defined herein as any protein comprising a "mucin domain". A mucin domain is rich in potential glycosylation sites, and has a high content of serine and/or threonine and proline, which can represent greater than 40% of the amino acids within the mucin domain. A mucin domain is heavily glycosylated with predominantly O-linked glycans. A mucin-domain polypeptide has at least about 60%, at least 70%, at least 80%, or at least 90% of its mass due to the glycans. Mucin domains may comprise tandem amino acid repeat units (also referred to herein as TR) that may vary in length from about 8 amino acids to 150 amino acids per each tandem repeat unit. The number of tandem repeat units may vary between 1 and 25 in a mucin-domain polypeptide of the invention.

Mucin-domain polypeptides of the invention include, but are not limited to, mucin proteins. A "portion thereof" is meant that the mucin polypeptide linker comprises at least one mucin domain of a mucin protein. Mucin proteins include any protein encoded for by a MUC gene (i.e., MUC1, MUC2, MUC3A, MUC3B, MUC4, MUC5AC, MUC5B, MUC6, MUC7, MUC8, MUC9, MUC11, MUC12, MUC13, MUC15, MUC16, MUC17, MUC19, MUC20, MUC21). The mucin domain of a mucin protein is typically flanked on either side by non-repeating amino acid regions. A mucin-domain polypeptide may comprise all or a portion of a mucin protein (e.g. MUC20) including the extracellular portion of the mucin protein, the signal sequence portion of the mucin protein, the transmembrane domain of the mucin protein, and/or the cytoplasmic domain of the mucin protein. A mucin-domain polypeptide may comprise all or a portion of a mucin protein of a soluble mucin protein. Preferably the mucin-domain polypeptide comprises the extracellular portion of a mucin protein.

A mucin domain polypeptide may also comprise all or a portion of a protein comprising a mucin domain but that is not encoded by a MUC gene. Such naturally occurring proteins that are not encoded by a MUC gene but that comprise mucin domains include, but are not limited to, membrane-anchored proteins such as transmembrane immunoglobulin and mucin domain (TIM) family proteins, fractalkine (neurotactin), P-selectin glycoprotein ligand 1 (PSGL-1, CD162), E-selectin, L-selectin, P-selectin, CD34, CD43 (leukosialin, sialophorin), CD45, CD68, CD96, CD164, GlyCAM-1, MAdCAM, red blood cell glycophorins, glycocalicin, glycophorin, LDL-R, ZP3, endosialin, decay accelerating factor (daf, CD55), podocalyxin, endoglycan, alpha-dystroglycan, neurofascin, EMR1, EMR2, EMR3, EMR4, ETL and epiglycanin.

A mucin-domain polypeptide may also comprise a non-naturally occurring polypeptide having a mucin domain as that term is defined herein. In one embodiment, the mucin-domain polypeptide is designed de novo to comprise a mucin domain in accordance with the invention.

In one embodiment a mucin domain polypeptide comprises domains of tandem amino acid repeats that are rich in Pro, Ser and Thr. In one aspect of this embodiment, the number of tandem repeat units within a mucin domain polypeptide of the invention is between 1 and 25. Preferably, the number of tandem repeat units within a mucin domain polypeptide is between 2 and 20. More preferably, the number of tandem repeat units within a mucin domain polypeptide is at least about 4. In a further aspect of this embodiment, the percentage of serine and/or threonine and proline residues within a mucin domain polypeptide of the invention is at least 10%. Preferably, the percentage of serine and/or threonine and proline residues within a mucin domain polypeptide of the invention is at least 20%. More preferably, the percentage of serine and/or threonine and proline residues within a mucin domain polypeptide of the invention is greater than 30%. In a final aspect of this embodiment, each tandem amino acid repeat unit within the mucin domain is comprised of at least 8 amino acids. Preferably, each unit is comprised of at least 16 amino acids. More preferably, each unit is comprised of at least 19 amino acids, and each unit may vary in length from about 19 amino acids to 150 amino.

In one embodiment the mucin-domain polypeptide comprises at least 32 amino acids, comprising at least 40% Serine, Threonine, and Proline. In one embodiment, a mucin-domain polypeptide in accordance with the invention comprises at least 2, 4, 8, 10 or 12 tandem amino acid repeating units of at least 8 amino acids in length per tandem repeating unit. Preferred amino acid sequences of a tandem repeating unit include, but are not limited to those of Table I. The mucin-domain polypeptide, and/or nucleic acids encoding the mucin-domain polypeptide, may be constructed using mucin-domain encoding sequences of proteins that are known in the art and are publicly available through sources such as GenBank.

TABLE I

| Name | Tandem Repeat (TR) Amino Acid Sequence (# of aa's) | Number of TR/MUC* | Accession Number[+] | Notes |
|---|---|---|---|---|
| MUC1 | PAPGSTAPPAHGVTSAPDTR (20) [SEQ ID NO: 11] | 21-125; 41 and 85 are most common | P15941 | Multiple variants of MUC1 exist |
| MUC2 | ITTTTTVTPTPTPTGTQTPTTTP (23) [SEQ ID NO: 12] | 99 | Q02817 | Major TR; alternative TR sequences exist |
| MUC3 (A) | ITTTETTSHDTPSFTSS (17) [SEQ ID NO: 13] | 20 | Q02505 | Degenerate TR sequence; long serine-rich and threonine-rich sequence also exist |
| MUC4 | ATPLPVTDTSSASTGH (16) [SEQ ID NO: 14] | 145-395 | Q99102 | Degenerate TR sequence, long serine-rich and threonine-rich sequence also exist |
| MUC5AC | TTSTTSAP (8) [SEQ ID NO: 15] | (46, 17, 34, 58)[∞] | P98088 | Consensus sequence T-T-S-T-T-S-A-P (SEQ ID NO: 15) |
| MUC5B | ATGSTATPSSTPGTTHTPPVLTTTATTPT (29) [SEQ ID NO: 16] | (11, 11, 17, 11, 23)[∞] | Q9HC84 | Degenerate TR sequence |
| MUC6 | PTS | NA | Q6W4X9 | NA |
| MUC7 | TTAAPPTPSATTQAPPSSSAPPE (23) [SEQ ID NO: 17] | 5-6 | Q8TAX7 | Degenerate TR sequence |
| MUC11/12 | EESTTVHSSPGATGTALFP (19) [SEQ ID NO: 18] | 28 | Q9UKN1 | Consensus sequence E-E-S-X-X-X-H-X-X-P-X-X-T-X-T-X-X-X-P (SEQ ID NO: 25) |

TABLE I-continued

| Name | Tandem Repeat (TR) Amino Acid Sequence (# of aa's) | Number of TR/MUC* | Accession Number+ | Notes |
| --- | --- | --- | --- | --- |
| MUC13 | PTS | NA | Q9H3R2 | |
| MUC14 | PTS | NA | | |
| MUC15 | PTS | NA | Q8N387 | |
| MUC16 | PTS | NA | Q8WXI7 | |
| MUC17 | SSSPTPAEGTSMPTSTYSEGRTPLTSMPVSTT LVATSAISTLSTTPVDTSTPVTNSTEA (60) [SEQ ID NO: 19] | 59-60 | Q685J3 | Degenerate TR sequence |
| MUC19 | PTS | NA | Q7Z5P9 | Repeats of G-V-T-G-T-T-G-P-S-A (SEQ ID NO: 26) |
| MUC20 | SESSASSDGPHPVITPSRA (19) [SEQ ID NO: 20] | 11-12 | Q8N307 | |
| MUC21 | ATNSESSTVSSGIST (15) [SEQ ID NO: 21] | 28 | Q5SSG8 | Degenerate TR sequence |
| MUC22 | PTS | NA | E2RYF6 | |
| TIM-1 | VPTTTT (6) [SEQ ID NO: 22] | 11 | Q96D42 | Degenerate TR sequence |
| TIM-4 | PTS | NA | Q96H15 | |
| Fractalkine | Mucin-like region (PTS) | NA | P78423 | |
| Macrosialin (CD68) | Mucin-like region (PTS) | NA | P34810 | |
| CD96 | PTS | NA | P40200 | |
| Endosialin | Pro-rich region | NA | Q9HCU0 | |
| DAF (CD55) | Pro/Thr-rich region | NA | P08174 | |
| Podocalyxin | Thr-rich region | NA | O00592 | |
| EMR1 | Ser/Thr-rich region | NA | Q14246 | |
| PSGL-1 | QTTQPAATEA (10) [SEQ ID NO: 23] | 12 | Q14242 | Degenerate TR sequence |

MUC8 and MUC9 are omitted; no reliable data
PTS proline/serine/threonine rich sequence
*approximate; TR number is reported as a range in most cases
+ Uniprot number
∞ The number n of TR is different in specific regions
NA Not announced In one embodiment a mucin-domain polypeptide total sequence length is from 32 to 200. As increased half life correlates with increasing hydrodynamic radius and, most importantly, an apparent molecular weight of greater than around 60 kD which allows circumvention of renal filtration, the length of the mucin-domain polypeptide is somewhat dependent on the size of the active moiety. For example, a peptide of molecular weight less than 5 kD, may require a mucin-domain polypeptide of 200 amino acids to achieve the desired half-life extension. In contrast, a protein of molecular weight of 40 kD, may only need a mucin-domain polypeptide of 32 amino acids to achieve the desired half-life. Furthermore, mucinylation allows for the half-life to be optimized by increasing or reducing the number of mucin tandem repeats in the mucin-domain peptide of the fusion protein.

Alternatively, the mucin-domain polypeptide moiety is provided as a variant mucin-domain polypeptide having a mutation in the naturally-occurring mucin-domain sequence of a wild type protein. For example, the variant mucin-domain polypeptide comprises additional O-linked glycosylation sites compared to the wild-type mucin-domain polypeptide. Alternatively, the variant mucin-domain polypeptide comprises amino acid sequence mutations that result in an increased number of serine, threonine or proline residues as compared to a wild type mucin-domain polypeptide Alternatively, the variant mucin-domain polypeptide sequences comprise added or subtracted charged residues, including but not limited to aspartic acid, glutamic acid, lysine, histidine, and arginine, which change the pI or charge of the molecule at a particular pH.

Active Protein and Therapeutic Active Protein

As used herein an "active protein" for inclusion in the fusion protein of the invention means a protein of biologic, therapeutic, prophylactic, or diagnostic interest or function and/or is capable of mediating a biological activity. A "therapeutic active protein" as that term is used herein is a protein that is capable of preventing or ameliorating a disease, disorder or conditions when administered to a subject.

In one embodiment, an active protein or therapeutic active protein in accordance with the invention specifically excludes immunoglobulin molecules or any containing an Fc domain, or any fragment thereof.

Of particular interest are active proteins and therapeutic active proteins for which an increase in a pharmacokinetic parameter, increased solubility, increased stability, or some other enhanced pharmaceutical property is sought, or those active proteins for which increasing the half-life would improve efficacy, safety, or result in reduce dosing frequency and/or improve patient compliance. Thus, the fusion proteins of the invention are prepared with various objectives in mind, including improving the therapeutic efficacy of the therapeutic active protein, for example, increasing the in vivo exposure or the length of time that the fusion protein of the invention remains within the therapeutic window when administered to a subject, compared to an active protein not linked to mucin-domain polypeptide.

In one embodiment, a fusion protein of the invention may comprise a single active protein linked to a mucin-domain polypeptide (as described more fully below). In another embodiment, the fusion protein of the invention can comprise a first active protein and a second molecule of the same active protein, resulting in a fusion protein comprising the two active proteins linked through one or more mucin-domain polypeptides. In another embodiment, the fusion protein of the invention can comprise a first active protein and a second distinct active protein, resulting in a fusion protein comprising the two active proteins with differing activities linked through one or more mucin-domain polypeptides.

In one embodiment, an active protein will exhibit a binding specificity to a given target or another desired biological characteristic when used in vivo or when utilized in an in vitro assay. For example, the active protein can be an agonist, a receptor, a ligand, an antagonist, an enzyme, or a hormone. Of particular interest are active proteins used or known to be useful for a disease or disorder wherein an extension in their half-life would permit less frequent dosing or an enhanced pharmacologic effect. Also of interest are active proteins that have a narrow therapeutic window between the minimum effective dose or blood concentration ($C_{min}$) and the maximum tolerated dose or blood concentration ($C_{max}$). In such cases, the linking of the active protein to a fusion protein comprising a mucin-domain polypeptide can result in an improvement in these properties, making them more useful as therapeutic or preventive agents compared to active protein not linked to a mucin-domain polypeptide.

The active proteins of the invention that are therapeutic active proteins can have utility in the treatment in various therapeutic or disease categories, including but not limited to: glucose and insulin disorders, metabolic disorders, cardiovascular diseases, coagulation/bleeding disorders, growth disorders or conditions, tumorigenic conditions, inflammatory conditions, autoimmune conditions, and other diseases and disease categories wherein a therapeutic protein or peptide not linked to a mucin-domain polypeptide exhibits a suboptimal half-life, or wherein a therapeutic protein or peptide does not exist.

An active protein of the invention can be a native, full-length protein or can be a fragment or a sequence variant of an active protein that retains at least a portion of the therapeutic activity of the native active protein. In one embodiment, the active proteins in accordance with the invention can be a recombinant polypeptide with a sequence corresponding to a protein found in nature. In another embodiment, the active proteins can be sequence variants, fragments, homologs, and mimetics of a natural sequence that retain at least a portion of the biological activity of the native active protein.

In non-limiting examples, the active protein can be a sequence that exhibits at least about 80% sequence identity, or alternatively 81%, 82%, 83%, 84%, 85%, 86%, 87%, 88%, 89%, 90%, 91%, 92%, 93%, 94%, 95%, 96%, 97%, 98%, 99%, or 100% sequence identity to the native active protein or a variant of a native active protein. Such proteins and peptides include but are not limited to the following: bioactive peptides (such as GLP-1, exendin-4, oxytocin, opiate peptides), cytokines, growth factors, chemokines, lymphokines, ligands, receptors, hormones, enzymes, antibodies and antibody fragments, domain antibodies, nanobodies, single chain antibodies, engineered antibody "alternative scaffolds" such as DARPins, centyrins, adnectins, and growth factors. Examples of receptors include the extracellular domain of membrane associated receptors (such as TNFR2, VEGF receptors, IL-1RI, IL-1RAcP, IL-4 receptor, hGH receptor, CTLA-4, PD-1, IL-6Rα, FGF receptors), soluble receptors which have been cleaved from their transmembrane domains, 'dummy' or 'decoy' receptors (such as IL-1RII, TNFRSF11B, DcR3), and any chemically or genetically modified soluble receptors. Examples of enzymes include activated protein C, factor VII, collagenase; agalsidase-beta; dornase-alpha; alteplase; pegylated-asparaginase; asparaginase; and imiglucerase. Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-β), interferon gamma (IFNγ), interferon gamma inducing factor I (IGIF), transforming growth factor beta (TGF-β), RANTES (regulated upon activation, normal T-cell expressed and presumably secreted), macrophage inflammatory proteins (e.g., MIP-1-α and MIP-1-β, *Leishmania* elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF a type II receptor, erythropoietin (EPO), insulin and soluble glycoproteins e.g., gp120 and gp160 glycoproteins. The gp120 glycoprotein is a human immunodeficiency virus (HIV) envelope protein, and the gp160 glycoprotein is a known precursor to the gp120 glycoprotein.

In one embodiment, the biologically active polypeptide is GLP-1. In another embodiment, the biologically active polypeptide is nesiritide, human B-type natriuretic peptide (hBNP). In yet another embodiment, the biologically active polypeptide is secretin, which is a peptide hormone composed of an amino acid sequence identical to the naturally occurring porcine secretin consisting of 27 amino acids. In one embodiment, the biologically active polypeptide is enfuvirtide, a linear 36-amino acid synthetic polypeptide which is an inhibitor of the fusion of HIV-1 with CD4+ cells. In one embodiment, the biologically active polypeptide is bivalirudin, a specific and reversible direct thrombin inhibitor. Antihemophilic Factor (AHF) may be selected as the active polypeptide. The mean in vivo half-life of HEMOFIL M™ AHF is known to be 14.7±5.1 hours (n=61). In another embodiment, erythropoietin is the biologically active polypeptide. Erythropoietin is a 165 amino acid glycoprotein manufactured by recombinant DNA technology and has the same biological effects as endogenous erythropoietin. In adult and pediatric patients with chronic renal failure, the elimination half-life of unmodified plasma erythropoietin after intravenous administration is known to range from 4 to 13 hours. In still another embodiment, the biologically active polypeptide is Reteplase. Reteplase is a non-glycosylated deletion mutein of tissue plasminogen activator (tPA), comprising the kringle 2 and the protease domains of human tPA. Based on the measurement of thrombolytic activity, the effective half-life of unmodified. Reteplase is known to be approximately 15 minutes.

In one preferred embodiment, the active polypeptide is Anakinra, a recombinant, nonglycosylated form of the human interleukin-1 receptor antagonist or the glycosylated form expressed in mammalian cells (IL-1Ra). In one case, Anakinra consists of 153 amino acids and has a molecular weight of 17.3 kilodaltons. It may be produced by recombinant DNA technology using an E. coli bacterial expression system. The glycosylated version of IL-1Ra can be produced in mammalian expression systems. The in vivo half-life of unmodified Anakinra is known to range from 4 to 6 hours.

In another preferred embodiment, the active polypeptide exendin-4. In one case, exendin-4 consists of 39 amino acids. It may be produced by recombinant DNA technology using an E. coli bacterial expression system. The in vivo half-life of unmodified exendin-4 is known to be 0.5 hours iv. [Ai, G., et al.; Pharmacokinetics of exendin-4 in Wistar rats; Journal of Chinese Pharmaceutical Sciences; 17 (2008) 6-10].

Becaplermin may also be selected as the active polypeptide. Becaplermin is a recombinant human platelet-derived growth factor (rhPDGF-BB) for topical administration. Becaplermin may be produced by recombinant DNA technology by insertion of the gene for the B chain of platelet derived, growth factor (PDGF) into the yeast strain Saccharomyces cerevisiae. One form of Becaplermin has a molecular weight of approximately 25 kD and is a homodimer composed of two identical polypeptide chains that are bound together by disulfide bonds. The active polypeptide may be Oprelvekin, which is a recombinant form of interleukin eleven (IL-11) that is produced in Escherichia coli (E. coli) by recombinant DNA technology. In one embodiment, the selected biologically active polypeptide has a molecular mass of approximately 19,000 daltons, and is non-glycosylated. The polypeptide is 177 amino acids in length and differs from the 178 amino acid length of native IL-11 only in lacking the amino-terminal proline residue, which is known not to result in measurable differences in bioactivity either in vitro or in vivo. The terminal half-life of unmodified Oprelvekin is known to be approximately 7 hrs. Yet another embodiment provides for a biologically active polypeptide which is Glucagon, a polypeptide hormone identical to human glucagon that increases blood glucose and relaxes smooth muscles of the gastrointestinal tract. Glucagon may be synthesized in a special non-pathogenic laboratory strain of E. coli bacteria that have been genetically altered by the addition of the gene for glucagon. In a specific embodiment, glucagon is a single-chain polypeptide that contains 29 amino acid residues and has a molecular weight of 3,483. The in vivo half-life is known to be short, ranging from 8 to 18 minutes.

G-CSF may also be chosen as the active polypeptide. Recombinant granulocyte-colony stimulating factor or G-CSF is used following various chemotherapy treatments to stimulate the recovery of white blood cells. The reported half-life of recombinant G-CSF is only 3.5 hours.

In one embodiment the biologically active polypeptide can be interferon alpha (IFN alpha). Chemically PEG-modified interferon-alpha 2a is Clinically validated for the treatment of hepatitis C. This PEGylated protein requires weekly injection and slow release formulations with longer half-life are desirable.

Additional cellular proteins include, but are not limited to: VEGF, VEGF-R1, VEGF-R2, VEGF-R3, Her-1, Her-2, Her-3, EGF-1, EGF-2, EGF-3, Alpha3, eMet, ICOS, CD40L, LEA-1, c-Met, ICOS, LFA-1, IL-6, B7.1, B7.2, OX40, IL-1b, TACI, IgE, BAFF, or BLys, TPO-R, CD19, CD20, CD22, CD33, CD28, IL-1-R1, TNFα, TRAIL-R1, Complement Receptor 1, FGFa, Osteopontin, Vitronectin, Ephrin A1-A5, Ephrin B1-B3, alpha-2-macroglobulin, CCL1, CCL2, CCL3, CCL4, CCL5, CCL6, CCL7, CXCL8, CXCL9, CXCL10, CXCL11, CXCL12, CCL13, CCL14, CCL15, CXCL16, CCL16, CCL17, CCL18, CCL19, CCL20, CCL21, CCL22, PDGF, TGFb, GMCSF, SCF, p40 (IL12/IL23), IL1b, IL1a, IL1ra, IL2, IL3, IL4, IL5, IL6, IL8, IL10, IL12, IL15, IL23, Fas, FasL, Flt3 ligand, 41BB, ACE, ACE-2, KGF, FGF-7, SCF, Netrin1,2, IFNa,b,g, Caspase-2, 3,7,8,10, ADAM S1,S5,8,9,15,TS1,TS5; Adiponectin, ALCAM, ALK-1, APRIL, Annexin V, Angiogenin, Amphiregulin, Angiopoietin-1,2,4, B7-1/CD80, B7-2/CD86, B7-H1, B7-H2, B7-H3, Bcl-2, BACE-1, BAK, BCAM, BDNF, bNGF, bECGF, BMP2,3,4,5,6,7,8; CRP, Cadherin-6,8,11; Cathepsin A, B, C, D, E, L, S, V, X; CD11a/LFA-1, LFA-3, GP2b3a, GH receptor, RSV F protein, IL-23 (p40, p19), IL-12, CD80, CD86, CD28, CTLA-4, a4P1, a4137, TNF/Lymphotoxin, IgE, CD3, CD20, IL-6, IL-6R, BLYS/ BAFF, IL-2R, HER2, EGFR, CD33, CD52, Digoxin, Rho (D), Varicella, Hepatitis, CMV, Tetanus, Vaccinia, Antivenom, Botulinum, Trail-R1, Trail-R2, cMet, TNF-R family, such as LA NGF-R, CD27, CD30, CD40, CD95, Lymphotoxin a/b receptor, Ws1-1 TL1A/TNFSF15, BAFF, BAFF-R/TNFRSF13C, TRAIL R2/TNFRSF10B, TRAIL R2/TNFRSF10B, Fas/TNFRSF6 CD27/TNFRSF7, DR3/ TNFRSF25, HVEM/TNFRSF14, TROY/TNFRSF19, CD40 Ligand/TNFSF5, BCMA/TNFRSF17, CD30/TNFRSF8, LIGHT/TNFSF14, 4-1BB/TNFRSF9, CD40/TNFRSF5, GITR/TNFRSF18, Osteoprotegerin/TNFRSF11B, RANK/ TNFRSF11A, TRAIL R3/TNFRSF10C, TRAIL/TNFSF10, TRANCE/RANK L/TNFSF11, 4-1BB Ligand/TNFSF9, TWEAK/TNFSF12, CD40 Ligand/TNFSFS, Fas Ligand/ TNFSF6, RELT/TNFRSF19L, APRIL/TNFSF13, DcR3/ TNFRSF6B, TNF R1/TNFRSF1A, TRAIL R1/TNFRSF10A, TRAIL R4/TNFRSF10D, CD30 Ligand/

TNFSF8, GITR Ligand/TNFSF18, TNFSF18, TAC1/TNFRSF13B, NGF R/TNFRSF16, OX40 Ligand/TNFSF4, TRAIL R2/TNFRSF10B, TRAIL R3/TNFRSF10C, TWEAK R/TNFRSF12, BAFF/BLyS/TNFSF13, DR6/TNFRSF21, TNF-alpha/TNFSF1A, Pro-TNF-alpha/TNFSF1A, Lymphotoxin beta R/TNFRSF3, Lymphotoxin beta R (LTbR)/Fc Chimera, TNF R1/TNFRSF1A, TNF-beta/TNFSF1B, PGRP-S, TNF R1/TNFRSF1A, TNT RII/TNFRSF1B, EDA-A2, TNF-alpha/TNFSF1A, EDAR, XEDAR, TNF RI/TNFRSF1A 4EBP1, 14-3-3 zeta, 53BP1, 2B4/SLAMF4, CCL21/6Ckine, 4-1 BB/TNFRSF9, 8D6A, 4-1BB Ligand/TNFSF9,8-oxo-dG, 4-Amino-1,8-naphthalimide, A2B5, Aminopeptidase LRAP/ERAP2, A33, Aminopeptidase N/ANPEP, Aag, Aminopeptidase P2/XPNPEP2, ABCG2, Aminopeptidase P1/XPNPEP1, ACE, Aminopeptidase PILS/ARTS1, ACE-2, Amnionless, Actin, Amphiregulin, beta-Actin, AMPK alpha 1/2, Activin A, AMPK alpha 1, Activin AB, AMPK alpha 2, Activin B, AMPK beta 1, Activin C, AMPK beta 2, Activin RIA/ALK-2, Androgen R/NR3C4, Activin RIB/ALK-4, Angiogenin, Activin RIIA, Angiopoietin-1, Activin RIIB, Angiopoietin-2, ADAMS, Angiopoietin-3, ADAM9, Angiopoietin-4, ADAM10, Angiopoietin-like 1, ADAM12, Angiopoietin-like 2, ADAM15, Angiopoietin-like 3, TACE/ADAM17, Angiopoietin-like 4, ADAM19, Angiopoietin-like 7/CDT6, ADAM33, Angiostatin, ADAMTS4, Annexin A1/Annexin I, ADAMTSS, Annexin A7, ADAMTS1, Annexin A10, ADAMTSL-1/Punctin, Annexin V, Adiponectin/Acrp30, ANP, AEBSF, AP Site, Aggrecan, APAF-1, Agrin, APC, AgRP, APE, AGTR-2, APT, AIF, APLP-1, Akt, APLP-2, Akt1, Apolipoprotein AI, Akt2, Apolipoprotein B, Akt3, APP, Serum Albumin, APRIL/TNFSF13, ALCAM, ARC, ALK-1, Artemin, ALK-7, Arylsulfatase A/ARSA, Alkaline Phosphatase, ASAH2/N-acylsphingosine Amidohydrolase-2, alpha 2u-Globulin, ASC, alpha-1-Acid Glycoprotein, ASGR1, alpha-Fetoprotein, ASK1, ALS, ATM, Ameloblastin, ATRIP, AMICA/JAML, Aurora A, AMIGO, Aurora B, AMIGO2, Axin-1, AMIGO3, Ax1, Aminoacylase/ACY1, Azurocidin/CAP37/HBP, Aminopeptidase A/ENPEP, B4GALT1, BIM, B7-1/CD80, 6-Biotin-17-NAD, B7-2/CD86, BLAME/SLAMF8, B7-H1/PD-L1, CXCL13/BLC/BCA-1, B7-H2, BLIMP1, B7-H3, Blk, B7-H4, BMI-1, BACE-1, BMP-1/PCP, BACE-2, BMP-2, Bad, BMP-3, BAFF/TNFSF13B, BMP-3b/GDF-10, BAFF R/TNFRSF13C, BMP-4, Bag-1, BMP-5, BAK, BMP-6, BAMBI/NMA, BMP-7, BARD1, BMP-8, Bax, BMP-9, BCAM, BMP-10, Bcl-10, BMP-15/GDF-9B, Bcl-2, BMPR-1A/ALK-3, Bcl-2 related protein A1, BMPR-IB/ALK-6, Bcl-w, BMPR-II, Bcl-x, BNIP3L, Bcl-xL, BOC, BCMA/TNFRSF17, BOK, BDNF, BPDE, Benzamide, Brachyury, Common beta Chain, B-Raf, beta IG-H3, CXCL14/BRAK, Betacellulin, BRCA1, beta-Defensin 2, BRCA2, BID, BTLA, Biglycan, Bub-1, Bik-like Killer Protein, c-jun, CD90/Thy1, c-Rel, CD94, CCL6/C10, CD97, C1q R1/CD93, CD151, C1qTNF1, CD160, C1qTNF4, CD163, C1qTNF5, CD164, Complement Component C1r, CD200, Complement Component C1s, CD200 R1, Complement Component C2, CD229/SLAMF3, Complement Component C3a, CD23/Fc epsilon RII, Complement Component C3d, CD2F-10/SLAMF9, Complement Component CSa, CDSL, Cadherin-4/R-Cadherin, CD69, Cadherin-6, CDC2, Cadherin-8, CDC25A, Cadherin-11, CDC25B, Cadherin-12, CDCP1, Cadherin-13, CDO, Cadherin-17, CDX4, E-Cadherin, CEACAM-1/CD66a, N-Cadherin, CEACAM-6, P-Cadherin, Cerberus 1, VE-Cadherin, CFTR, Calbindin D, cGMP, Calcineurin A, Chem R23, Calcineurin B, Chemerin, Calreticulin-2, Chemokine Sampler Packs, CaM Kinase II, Chitinase 3-like 1, cAMP, Chitotriosidase/CHIT1, Cannabinoid R1, Chk1 Cannabinoid R2/CB2/CNR2, Chk2, CAR/NR113, CHL-1/L1CAM-2, Carbonic Anhydrase I, Choline Acetyltransferase/ChAT, Carbonic Anhydrase II, Chondrolectin, Carbonic Anhydrase III, Chordin, Carbonic Anhydrase IV, Chordin-Like 1, Carbonic Anhydrase Va., Chordin-Like 2, Carbonic Anhydrase VB, CINC-1, Carbonic Anhydrase VI, CINC-2, Carbonic Anhydrase VII, CINC-3, Carbonic Anhydrase VIII, Claspin, Carbonic Anhydrase IX, Claudin-6, Carbonic Anhydrase X, CLC, Carbonic Anhydrase XII, CLEC-1, Carbonic Anhydrase XIII, CLEC-2, Carbonic Anhydrase XIV, CLECSF13/CLEC4F, Carboxymethyl Lysine, CLECSF8, Carboxypeptidase A1/CPA1, CLF-1, Carboxypeptidase A2, CL-P1/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147, Carnosine Dipeptidase 1, CNP, Caronte, CNTF, CART, CNTF R alpha, Caspase, Coagulation Factor II/Thrombin, Caspase-1, Coagulation Factor III/Tissue Factor, Caspase-2, Coagulation Factor VII, Caspase-3, Coagulation Factor X, Caspase-4 Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component C1rLP, beta-Catenin, Complement Component C1qA, Cathepsin 1, Complement Component C1qC, Cathepsin 3, Complement Factor D, Cathepsin 6, Complement Factor 1, Cathepsin A, Complement MASP3, Cathepsin B, Connexin 43, Cathepsin C/DPPI, Contactin-1, Cathepsin D, Contactin-2/TAG1, Cathepsin E, Contactin-4, Cathepsin F, Contactin-5, Cathepsin H, Corin, Cathepsin L, Cornulin, Cathepsin O, CORS26/C1qTNF, 3, Cathepsin S, Rat Cortical Stem Cells, Cathepsin V, Cortisol, Cathepsin X/Z/P, COUP-TF I/NR2F1, CBP, COUP-TF II/NR2F2, CCI, COX-1, CCK-A R, COX-2, CCL28, CRACC/SLAMF7, CCR1, C-Reactive Protein, CCR2, Creatine Kinase, Muscle/CKMM, CCR3, Creatinine, CCR4, CREB, CCR5, CREG, CCR6, CRELD1, CCR7, CRELD2, CCR8, CRHBP, CCR9, CRHR-1, CCR10, CRIM1, CD155/PVR, Cripto, CD2, CRISP-2, CD3, CRISP-3, CD4, Crossveinless-2, CD4+/45RA−, CRTAM, CD4+/45RO−, CRTH-2, CD4+/CD62L−/CD44, CRY1, CD4+/CD62L+/CD44, Cryptic, CD5, CSB/ERCC6, CD6, CCL27/CTACK, CD8, CTGF/CCN$^2$, CD8+/45RA−, CTLA-4, CD8+/45RO−, Cubilin, CD9, CX3CR1, CD14, CXADR, CD27/TNFRSF7, CXCL16, CD27 Ligand/TNFSF7, CXCR3, CD28, CXCR4, CD30/TNFRSF8, CXCR5, CD30 Ligand/TNFSF8, CXCR6, CD31/PECAM-1, Cyclophilin A, CD34, Cyr61/CCN1, CD36/SR-B3, Cystatin A, CD38, Cystatin B, CD40/TNFRSF5, Cystatin C, CD40 Ligand/TNFSFS, Cystatin D, CD43, Cystatin E/M, CD44, Cystatin F, CD45, Cystatin H, CD46, Cystatin H2, CD47, Cystatin S, CD48/SLAMF2, Cystatin SA, CD55/DAF, Cystatin SN, CD58/LFA-3, Cytochrome c, CD59, Apocytochrome c, CD68, Holocytochrome c, CD72, Cytokeratin 8, CD74, Cytokeratin 14, CD83, Cytokeratin 19, CD84/SLAMF5, Cytonin, D6, DISP1, DAN, Dkk-1, DANCE, Dkk-2, DARPP-32, Dkk-3, DAX1/NROB1, Dkk-4, DCC, DLEC, DCIR/CLEC4A, DLL1, DCAR, DLL4, DcR3/TNFRSF6B, d-Luciferin, DC-SIGN, DNA Ligase IV, DC-SIGNR/CD299, DNA Polymerase beta, DcTRAIL R1/TNFRSF23, DNAM-1, DcTRAIL, R2/TNFRSF22, DNA-PKcs, DDR1, DNER, DDR2, Dopa Decarboxylase/DDC, DEC-205, DPCR-1, Decapentaplegic, DPP6, Decorin, DPPA4, Dectin-1/

CLEC7A, DPPA5/ESG1, Dectin-2/CLEC6A, DPPII/QPP/ DPP7, DEP-1/CD148, DPPIV/CD26, Desert Hedgehog, DR3/TNFRSF25, Desmin, DR6/TNFRSF21, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-1, EphA6, ECE-2, EphA7, ECF-L/CHI3L3, EphA8, ECM-1, EphB1, Ecotin, EphB2, EDA, EphB3, EDA-A2, EphB4, EDAR, EphB6, EDG-1, Ephrin, EDG-5, Ephrin-A1, EDG-8, Ephrin-A2, eEF-2, Ephrin-A3, EGF, Ephrin-A4, EGF R, Ephrin-A5, EGR1, Ephrin-B, EG-VEGF/PK1, Ephrin-B1, eIF2 alpha, Ephrin-B2, eIF4E, Ephrin-B3, Elk-1, Epigen, EMAP-II, Epimorphin/Syntaxin 2, EMMPRIN/CD147, Epiregulin, CXCL5/ENA, EPR-1/Xa Receptor, Endocan, ErbB2, Endoglin/CD105, ErbB3, Endoglycan, ErbB4, Endonuclease III, ERCC1, Endonuclease IV, ERCC3, Endonuclease V, ERK1/ERK2, Endonuclease VIII, ERK1, Endorepellin/Perlecan, ERK2, Endostatin ERK3, Endothelin-1, ERK5/BMK1, Engrailed-2, ERR alpha/NR3B1, EN-RAGE, ERR beta/NR3B2, Enteropeptidase/Enterokinase, ERR gamma/NR3B3, CCL11/Eotaxin, Erythropoietin, CCL24/Eotaxin-2, Erythropoietin R, CCL26/Eotaxin-3, ESAM, EpCAM/TROP-1, ER alpha/NR3A1, EPCR, ER beta/NR3A2, Eph, Exonuclease III, EphA1, Exostosin-like 2/EXTL2, EphA2, Exostosin-like 3/EXTL3, EphA3, FABP1, FGF-BP, FABP2, FGF R1-4, FABP3, FGF R1, FABP4, FGF R2, FABP5, FGF R3, FABP7, FGF R4, FABP9, FGF R5, Complement Factor B, Fgr, FADD, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP1, FLRG, FATP4, FLRT1, FATP5, FLRT2, Fc gamma R1/CD64, FLRT3, Fe gamma RIIB/CD32b Flt-3, Fc gamma RIIC/CD32c, Flt-3 Ligand, Fc gamma RIIA/CD32a, Follistatin, Fc gamma RIII/CD16, Follistatin-like 1, FcRH1/IRTA5, FosB/G0S3, FcRH2/IRTA4, FoxD3, FcRH4/IRTA1, FoxJ1, FcRH5/IRTA2, FoxP3, Fc Receptor-like 3/CD16-2, Fpg, FEN-1, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-10, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-21, FXR/NR1H4, FGF-22, Fyn, FGF-23, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF18, GABA-A-R alpha 5, GLI-1, GABA-A-R alpha 6, GLI-2, GABA-A-R beta 1, GLP/EHMT1, GABA-A-R beta 2, GLP-1 R, GABA-A-R beta 3, Glucagon, GABA-A-R gamma 2, Glucosamine (N-acetyl)-6-Sulfatase/GNS, GABA-B-R2, GluR1, GAD1/GAD67, GluR2/3, GAD2/GAD65, GluR2, GADD45 alpha, GluR3, GADD45 beta, Glut1, GADD45 gamma, Glut2, Galectin-1, Glut3, Galectin-2, Glut4, Galectin-3, GlutS, Galectin-3 BP, Glutaredoxin 1, Galectin-4, Glycine R, Galectin-7, Glycophorin A, Galectin-8, Glypican 2, Galectin-9, Glypican 3, GalNAc4S-65T, Glypican 5, GAP-43, Glypican 6, GAPDH, GASP-CSF, Gas1, GM-CSF R alpha, Gas6, GMF-beta, GASP-1/WFIKKNRP, gp130, GASP-2/WFIKKN, Glycogen Phosphorylase BB/GPBB, GATA-1, GPR15, GATA-2, GPR39, GATA-3, GPVI, GATA-4, GR/NR3C1, GATA-5, Gr-1Ly-6G, GATA-6, Granulysin, GBL, Granzyme A, GCNF/NR6A1, Granzyme B, CXCL6/GCP-2, Granzyme D, G-CSF, Granzyme G, G-CSF R, Granzyme H, GDF-1, GRASP, GDF-3 GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-1, GSK-3 alpha, GFR alpha-1/GDNF R alpha-1, GSK-3 beta, GFR alpha-2/GDNF R alpha-2, EGN1T, H2AX, Histidine, H60, HM74A, HAI-1, HMGA2, HAI-2, HMGB1, HAI-2A, TCF-2/HNF-1 beta, HAI-2B, HNF-3 beta/FoxA2, HAND1, HNF-4 alpha/NR2A1, HAPLN1, HNF-4 gamma/NR2A2, Airway Trypsin-like Protease/HAT, HO-1/HMOX1/HSP32, HB-EGF, HO-2/HMOX2, CCL14a/HCC-1, HPRG, CCL14b/HCC-3, Hrk, CCL16/HCC-4, HRP-1, alpha HCG, HS6ST2, Hck, HSD-1, HCR/CRAM-A/B, HSD-2, HDGF, HSP10/EPF, Hemoglobin, HSP27, Hepassocin, HSP60, HES-1, HSP70, HES-4, HSP90, HGF, HTRA/Protease Do, HGF Activator, HTRA1/PRSS11, HGF R, HTRA2/Omi, HIF-1 alpha, HVEM/TNFRSF14, HIF-2 alpha, Hyaluronan, HIN-1/Secretoglobulin 3A1,4-Hydroxynonenal, Hip, CCL1/1-309/TCA-3, IL-10, cIAP (pan), IL-10 R alpha, cIAP-1/HIAP-2, IL-10 R beta, cIAP-2/HIAP-1, IL-11, IBSP/Sialoprotein II, IL-11 R alpha, ICAM-1/CD54, IL-12, ICAM-2/CD102, IL-12/IL-23 p40, ICAM-3/CD50, IL-12 R beta 1, ICAM-5, IL-12 R beta 2, ICAT, IL-13, ICOS, IL-13 R alpha 1, Iduronate 2-Sulfatase/IDS, IL-13 R alpha 2, IFN, IL-15, IFN-alpha, IL-15 R alpha, IFN-alpha 1, IL-16, IFN-alpha 2, IL-17, IFN-alpha 4b, IL-17 R, IFN-alpha A, IL-17 RCC, IFN-alpha B2, IL-17 RD, IFN-alpha C, IL-17B, IFN-alpha D, IL-17B R, IFN-alpha F, IL-17C, IFN-alpha G, IL-17D, IFN-alpha H2, IL-17E, IFN-alpha 1, IL-17F, IFN-alpha J1, IL-18/IL-1F4, IFN-alpha K, IL-18 BPa, IFN-alpha WA, IL-18 BPc, IFN-alpha/beta R1, IL-18 BPd, IFN-alpha/beta R2, IL-18 R alpha/IL-1 R5, IFN-beta, IL-18 R beta/IL-1 R7, IFN-gamma IL-19, IFN-gamma R1, IL-20, IFN-gamma R2, IL-20 R alpha, IFN-omega, IL-20 R beta, IgE, IL-21, IGFBP-1, IL-21 R, IGFBP-2, IL-22, IGFBP-3, IL-22 R, IGFBP-4, IL-22BP, IGFBP-5, IL-23, IGFBP-6, IL-23 R, IGFBP-L1, IL-24, IGFBP-rp1/IGFBP-7, IL-26/AK155, IGFBP-rP10, IL-27, IGF-I, IL-28A, IGF-I R, IL-28B, IGF-II, IL-29/IFN-lambda 1, IGF-II R, IL-31, IgG, IL-31 RA, IgM, IL-32 alpha, IGSF2, IL-33, IGSF4A/SynCAM, ILT2/CD85j, IGSF4B, ILT3/CD85k, IGSF8, ILT4/CD85d, IgY, ILT5/CD85a, IkB-beta, ILT6/CD85e, IKK alpha, Indian Hedgehog, IKK epsilon, INSRR, IKK gamma, Insulin, IL-1 alpha/IL-1F1, Insulin R/CD220, IL-1 beta/IL-1F2, Proinsulin, IL-1ra/IL-1F3, Insulysin/IDE, IL-1FIL1 delta, Integrin alpha 2/CD49b, IL-1F6/FIL1 epsilon, Integrin alpha 3/CD49c, IL-1F7/FIL1 zeta, Integrin alpha 3 beta 1/VLA-3, IL-IF8/FIL1 eta, Integrin alpha 4/CD49d, IL-1F9/IL-1H1, Integrin alpha 5/CD49e, IL-1F10/IL-1HY2, Integrin alpha 5 beta 1, IL-1 R1, Integrin alpha 6/CD49f, IL-1 RII, Integrin alpha 7, IL-1 R3/IL-1 R AcP, Integrin alpha 9, IL-1 R4/ST2, Integrin alpha E/CD103, IL-1 R6/IL-1 R rp2, Integrin alpha L/CD11a, IL-1 R8, Integrin alpha L beta 2, IL-1 R9, Integrin alpha M/CD11b, IL-2, Integrin alpha M beta 2, IL-2 R alpha, Integrin alpha V/CD51, IL-2 R beta, Integrin alpha V beta 5, IL-3, Integrin alpha V beta 3, IL-3 R alpha, Integrin alpha V beta 6, IL-3 R beta, Integrin alpha X/CD11c IL-4, Integrin beta 1/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL10/IP-10/CRG-2, IL-7 R alpha/CD127, IRAK1, CXCR1/IL-8 RA, IRAK4, CXCR2/IL-8 RB, IRS-1, CXCL8/IL-8, Islet1, IL-9, CXCL11/1-TAC, IL-9 R, Jagged 1, JAM-4/IGSFS, Jagged 2, JNK, JAM-A, JNK1/JNK2, JAM-B/VE-JAM, JNK1, JAM-C, JNK2, Kininogen, Kallikrein 3/PSA, Kininostatin, Kallikrein 4, KIR/CD158, Kallikrein 5, KIR2DL1, Kallikrein 6/Neurosin, KIR2DL3, Kallikrein 7, KIR2DL4/CD158d. Kallikrein 8/Neuropsin, KIR2DS4, Kallikrein 9, KIR3DL1, Plasma Kallikrein/KLKB1, KIR3DL2, Kallikrein 10, Kirre12, Kallikrein 11, KLF4, Kallikrein 12, KLFS, Kallikrein 13, KLF6, Kallikrein 14, Klotho, Kallikrein 15, Klotho beta, KC, KOR, Keap1, Kremen-1, Kell, Kremen-2, KGF/FGF-7, LAG-3, LINGO-2, LAIR1, Lipin 2, LAIR2, Lipocalin-1, Laminin alpha 4, Lipocalin-2/NGAL, Laminin gamma 1,5-Lipoxygenase, Laminin I, LXR alpha/NR1H3, Laminin S, LXR beta/NR1H2, Laminin-1, Livin, Laminin-5, LIX, LAMP, LMIR1/CD300A, Langerin, LMIR2/CD300c, LAR, LMIR3/CD300LF, Latexin, LMIRS/CD300LB, Layilin, LMIR6/CD300LE, LBP, LMO2, LDL R, LOX-1/SR-E1, LECT2, LRH-1/NR5A2, LEDGE, LRIG1, Lefty, LRIG3, Lefty-1, LRP-1, Lefty-A, LRP-6, Legumain, LSECtin/CLEC4G, Leptin, Lumican, Leptin R, CXCL15/Lungkine, Leukotriene B4, XCL1/Lymphotactin, Leukotriene B4 R1, Lymphotoxin, LIF, Lymphotoxin beta/TNFSF3, LIF R alpha, Lymphotoxin beta R/TNFRSF3, LIGHT/TNFSF14, Lyn, Limitin, Lyp, LIMPII/SR-2, Lysyl Oxidase Homolog 2, LIN-28, LYVE-1, LINGO-1, alpha 2-Macroglobulin, CXCL9/MIG, MAD2L1, Mimecan, MAdCAM-1, Mindin, MafB, Mineralocorticoid R/NR3C2, MafF, CCL3L1/MIP-1 alpha Iisoform LD78 beta, MafG, CCL3/MIP-1 alpha, MafK, CCL4L1/LAG-1, MAG/Siglec-4-a, CCL4/MIP-1 beta, MANF, CCL15/MIP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-1, Mash1, MIP-II, Matrilin-2, MIP-III, Matrilin-3, MIS/AMH, Marlin-4, MIS R11, Matriptase/ST14, MIXL1, MBL, MKK3/MKK6, MBL-2, MKK3, Melanocortin 3R/MC3R, MKK4, MCAM/CD146, MKK6, MCK-2, MKK7, Mc1-1, MKP-3, MCP-6, MLH-1, CCL2/MCP-1, MLK4 alpha, MCP-11, MMP, CCL8/MCP-2, MMP-1, CCL/MCP-3/MARC, MMP-2, CCL13/MCP-4, MMP-3, CCL12/MCP-5, MMP-7, M-CSF, MMP-8, M-CSF R, MMP-9, MCV-type II, MMP-10, MD-1, MMP-11, MD-2, MMP-12, CCL22/MDC, MMP-13, MDL-1/CLECSA, MMP-14, MDM2, MMP-15, MEA-1, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mrell, Mesothelin, MRP1 Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-1, MGL2, Musashi-1, MGMT, Musashi-2, MIA, MuSK MICA, MutY DNA Glycosylase, MICB, MyD88, MICL/CLEC12A, Myeloperoxidase, beta 2 Microglobulin, Myocardin, Midkine, Myocilin, MIF, Myoglobin, NAIP NGFI-B gamma/NR4A3, Nanog, NgR2/NgRH1, CXCL7/NAP-2, NgR3/NgRH2, Nbs1, Nidogen-1/Entactin, NCAM-1/CD56, Nidogen-2, NCAM-L1, Nitric Oxide, Nectin-1, Nitrotyrosine, Nectin-2/CD112, NKG2A, Nectin-3, NKG2C, Nectin-4, NKG2D, Neogenin, NKp30, Neprilysin/CD10, NKp44, Neprilysin-2/MMEL1/MMEL2, NKp46/NCR1, Nestin, NKp80/KLRF1, NETO2, NKX2.5, Netrin-1, NMDA R, NR1 Subunit, Netrin-2, NMDA R, NR2A Subunit, Netrin-4, NMDA R, NR2B Subunit, Netrin-Gla, NMDA R, NR2C Subunit, Netrin-G2a, N-Me-6,7-diOH-TIQ, Neuregulin-1/NRG1, Nodal, Neuregulin-3/NRG3, Noggin, Neuritin, Nogo Receptor, NeuroD1, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAM1, NRAGE, NF-H, NrCAM, NFkB1, NRL, NFkB2, NT-3, NF-L, NT-4, NF-M, NTB-A/SLAMF6, NG2/MCSP, NTH1, NGF R/TNFRSF16, Nucleostemin, beta-NGF, Nurr-1/NR4A2, NGFI-B alpha/NR4A1, OAS2, Orexin B, OBCAM, OSCAR, OCAM, OSF-2/Periostin, OCIL/CLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Olig1, Osteocrin, Olig2, Ostcopontin, Olig3, Osteoprotegerin/TNFRSF11B, Oligodendrocyte Marker 01, Otx2, Oligodendrocyte Marker 04, OV-6, OMgp, OX40/TNFRSF4, Opticin, OX40 Ligand/TNFSF4, Orexin A, OAS2, Orexin B, OBCAM, OSCAR, OCAM, OSF-2/Periostin, OCIL/CLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF11B, Oligodendrocyte Marker 01, Otx2, Oligodendrocyte Marker 04, OV-6, OMgp, OX40/TNFRSF4, Opticin, OX40 Ligand/TNFSF4, Orexin A, RACK1, Ret, Rad1, REV-ERB alpha/NR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBO1, RAGE, ROBO2, Ra1A/Ra1B, ROBO3, Ra1A, ROBO4, Ra1B, ROR/NR1F1-3 (pan), RANK/TNFRSF11A, ROR alpha/NR1F1, CCL5/RANTES, ROR gamma/NR1F3, Rap1A/B, RTK-like Orphan Receptor 1/ROR1, RAR alpha/NR1B1, RTK-like Orphan Receptor 2/ROR2, RAR beta/NR1B2, RP105, RAR gamma/NR1B3, RPA2, Ras, RSK (pan), RBP4, RSK1/RSK2, RECK, RSK1, Reg 2/PAP, RSK2, Reg I, RSK3, Reg II, RSK4, Reg III, R-Spondin 1, Reg Ma, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, S100A10, SLITRK5, S100A8, SLP1, S100A9, SMAC/Diablo, S100B, Smad1, STOOP, Smad2, SALL1, Smad3, delta-Sareoglycan, Smad4, Sca-1/Ly6, Smad5, SCD-1, Smad7, SCF, Smad8, SCF R/c-kit, SMC1, SCGF, alpha-Smooth Muscle Actin, SCL/Tall, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, S or CS1, beta-Secretase, S or CS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX10, Semaphorin 6B, SOX17, Semaphorin 6C, SOX21 Semaphorin 6D, SPARC, Semaphorin 7A, SPARC-like 1, Separase, SP-D, Serine/Threonine Phosphatase Substrate I, Spinesin, Serpin A1, F-Spondin, Serpin A3, SR-AI/MSR, Serpin A4/Kallistatin, Src, Serpin A5/Protein C Inhibitor, SREC-I/SR-F1, Serpin A8/Angiotensinogen, SREC-II, Serpin B5, SSEA-1, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G1/C1 Inhibitor, Stanniocalcin 2, Serpin 12, STAT1 Serum Amyloid A1, STAT2, SF-1/NR5A1, STAT3, SGK, STAT4, SHBG, STAT5a/b, SHIP, STAT5a, SHP/NROB2, STAT5b, SHP-1, STAT6, SHP-2, VE-Statin, SIGIRR, Stella/Dppa3, Siglec-2/CD22, STRO-1, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu—Zn SOD, SIGNR4, Superoxide Dismutase-2/Mn-SOD, SIRP beta 1, Superoxide Dismutase-3/EC-SOD, SKI, Survivin, SLAM/CD150, Synapsin 1, Sleeping Beauty Transposase, Syndecan-1/CD138, Slit3, Syndecan-2, SLITRK1, Syndecan-3, SLITRK2, Syndecan-4, SLITRK4, TAC1/TNFRSF13B, TMEFF1/Tomoregulin-1, TAO2, TMEFF2, TAPP1 TNF-alpha/TNFSF1A, CCL17/TARC, TNF-beta/TNFSF1B, Tau, TNF R1/TNFRSF1A, TC21/R-Ras2, TNF R11/TNFRSF1B, TCAM-1, TOR, TCCR/WSX-1, TP-1, TC-PIP, TP63/TP73L, TDG, TR, CCL25/TECK, TR alpha/NR1A1, Tenascin C, TR beta 1/NR1A2, Tenascin R, TR2/NR2C1, TER-119, TR4/NR2C2, TERT, TRA-1-85, Testican 1/SPOCK1, TRADD, Testican 2/SPOCK2, TRAF-1, Testican 3/SPOCK3, TRAF-2, TFPI, TRAF-3, TFPI-2, TRAF-4, TGF-alpha, TRAF-6, TGF-beta, TRAIL/TNFSF10, TGF-beta 1, TRAIL R1/TNFRSF10A, LAP (TGF-beta 1), TRAIL R2/TNFRSF10B, Latent TGF-beta 1, TRAIL R3/TNFRSF10C, TGF-beta 1.2, TRAIL R4/TNFRSF10D, TGF-beta 2, TRANCE/TNFSF11, TGF-beta 3, TfR (Transferrin R), TGF-beta 5, Apo-Transferrin, Latent TGF-beta bp1, Holo-Transferrin, Latent TGF-beta bp2, Trappin-2/Elafin, Latent TGF-beta bp4, TREM-1, TGF-beta RI/ALK-5, TREM-2, TGF-beta RII, TREM-3, TGF-beta RIIb, TREML1/TLT-1, TGF-beta RIII, TRF-1, Thermolysin, TRF-2, Thioredoxin-1, TRH-degrading Ectoenzyme/TRHDE, Thioredoxin-2, TRIMS, Thioredoxin-80, Tripeptidyl-Peptidase 1, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF19, Thrombospondin-4, Trypsin 1, Thymopoietin, Trypsin 2/PRSS2, Thymus Chemokine-1, Trypsin 3/PRSS3, Tie-1, Tryptase-5/Prss32, Tic-2, Tryptase alpha/TPS1, TIM-1/KIM-1/HAVCR, Tryptase beta-1/MCPT-7, TIM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-1, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF12, TLRS, Tyk2, TLR6, Phospho-Tyrosine, TLR9, Tyrosine Hydroxylase, TLX/NR2E1, Tyrosine Phosphatase Substrate I, Ubiquitin, UNC5H3, Ugi, UNC5H4, UGRP1, UNG, ULBP-1, uPA, ULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/Flt-4, Vasostatin, Versican, Vav-1, VGSQ, VCAM-1, VHR, VDR/NR111, Vimentin, VEGF, Vitronectin, VEGF-B, VLDLR, VEGF-C, vWF-A2, VEGF-D, Synuclein-alpha, Ku70, WASP, Wnt-7b, WIF-1, Wnt-8a WISP-1/CCN4, Wnt-8b, WNK1, Wnt-9a, Wnt-1, Wnt-9b, Wnt-3a, Wnt-10a, Wnt-4, Wnt-10b, Wnt-5a, Wnt-11, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

Other active polypeptides include: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleukin, denileukin diftitox, interferon alfa-n3 (injection), interferon alfa-n1, DL-8234, interferon, Suntory (gamma-1 a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP-401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphanate, octocog alfa, Factor VIII, palifermin, Indikinase, tenecteplase, alteplase, pamiteplase, reteplase, nateplase, monteplase, follitropin alfa, rFSH, hpFSH, micafungin, pegfilgrastim, lenogastim, nartograstim, sermorelin, glucagon, exenatide, pramlintide, imiglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enfuvirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasermin, Roferon-A, interferon-alpha 2, Alfaferone, interferon alfacon-1, interferon alpha, Avonex' recombinant human luteinizing hormone, dornase alfa, trafermin, ziconotide, taltirelin, diboterminalfa, atosiban, becaplermin, eptifibatide, Zemaira, CTC-111, Shanvac-B, HPV vaccine (quadrivalent), NOV-002, octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexiganan acetate, ADI-PEG-20, LD1-200, degarelix, cintredekin besudotox, FavId, MDX-1379, ISAtx-247, liraglutide, teriparatide (osteoporosis), tifacogin, AA-4500, T4N5 liposome lotion, catumaxomab, DWP-413, ART-123, Chrysalin, desmoteplase, amediplase, corifollitropin alpha, TH-9507, teduglutide, Diamyd, DWP-412, growth hormone (sustained release injection), recombinant G-CSF, insulin (inhaled, AIR), insulin (inhaled, Technosphere), insulin (inhaled, AERX), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneation), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-1 (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-50-4798, interleukin-4, PRX-321, Pepscan, iboctadekin, rh lactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax- P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosin beta-4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, TP-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotide acetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, all phosphatase, EP-2104R, Melanotan-II, bremelanotides, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B 19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBR1-93.02, MTB72F vaccine (tuberculosis), MVA-Ag85A vaccine (tuberculosis), FAR-404, BA-210, recombinant plague F1V vaccine, AG-702, OXSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, PIA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3881L-3, TST-10088, PRO-1762, Combotox, cholecystokinin-B/gastrin-receptor binding peptides, 111In-hEGF, AE-37, trastuzumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A2 (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1001 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV-4710, ALG-889, Org-41259, rhCC10, F-991, thymopentin (pulmonary diseases), r(m) CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S. pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HGV vaccine (core antigen+ISCOMATRIX), hPTH(1-34) (transdermal, ViaDerm), 768974, SYN-101, PGN-0052, aviscumine, BIM-23190, tuberculosis vaccine, multi-epitope tyrosinase peptide, cancer vaccine, enkastim, APC-8024, G1-5005, ACC-001, TTS-CD3, vascular-targeted TNF (solid tumors), desmopressin (buccal controlled-release), onercept, TP-9201.

The nucleic acid and amino acid sequences of numerous active proteins are well known in the art and descriptions and sequences are available in public databases such as Chemical Abstracts Services Databases (e.g., the CAS Registry), GenBank, GenPept, Entrez Nucleotide, Entrez Protein, The Universal Protein Resource (UniProt) and subscription provided databases such as GenSeq (e.g., Derwent). Polynucleotide sequences may be a wild type polynucleotide sequence encoding a given active protein (e.g., either full length or mature), or in some instances the sequence may be a variant of the wild type polynucleotide sequence (e.g., a polynucleotide which encodes the wild type active protein, wherein the DNA sequence of the polynucleotide has been optimized, for example, for expression in a particular species; or a polynucleotide encoding a variant of the wild type protein, such as a site directed mutant or an allelic variant. It is well within the ability of the skilled artisan to use a wild-type or consensus cDNA sequence or a codon-optimized variant of a active protein to create fusion protein constructs contemplated by the invention using methods known in the art and/or in conjunction with the guidance and methods provided herein, and described more fully in the Examples.

Pharmacokinetic Properties of the Fusion Proteins

The invention provides fusion proteins of therapeutic active proteins with enhanced pharmacokinetics compared to the therapeutic active protein not linked to a mucin-polypeptide domain, that, when used at the optimal dose determined for the composition by the methods described herein, can achieve enhanced pharmacokinetics compared to a comparable dose of the therapeutic active protein not linked to a mucin-domain polypeptide in accordance with the invention. As used herein, a "comparable dose" means a dose with an equivalent moles/kg for the therapeutic active protein that is administered to a subject in a comparable fashion. It will be understood in the art that a "comparable dosage" of the fusion protein would represent a greater weight of agent but would have essentially the same mole-equivalents of the therapeutic active protein in the dose of the fusion protein and/or would have the same approximate molar concentration relative to the therapeutic active protein.

The pharmacokinetic (PK) properties of a therapeutic active protein that can be enhanced by linking a mucin polypeptide domain to the therapeutic active protein include half-life, area under the curve (AUC), $C_{max}$, $T_{max}$, peak-totrough concentration ratio, and volume of distribution. The enhancements in PK properties can lead to improvements in efficacy due to increased exposure, reduction in adverse events due to a reduction in dose and a dampening of $C_{max}$, and a reduction in dosing frequency. As described more fully in the Examples, the invention provides fusion proteins comprising a mucin-domain polypeptide linked to a therapeutic active protein that increase the half-life for the administered fusion protein, compared to the corresponding therapeutic active protein not linked to the fusion protein, of at least about two-fold longer, or at least about three-fold, or at least about four-fold, or at least about five-fold, or at least about six-fold, or at least about seven-fold, or at least about eight-fold, or at least about nine-fold, or at least about ten-fold, or at least about 15-fold, or at least a 20-fold or greater an increase in half-life compared to the therapeutic active not linked to the fusion protein.

Similarly, the fusion proteins of the invention can have an increase in AUC of at least about 50%, or at least about 60%, or at least about 70%, or at least about 80%, or at least about 90%, or at least about 100%, or at least about 150%, or at least about 200%, or at least about 300% increase in AUC compared to the corresponding therapeutic active protein not linked to the fusion protein. The pharmacokinetic parameters of half-life and AUC of a fusion protein of the invention can be determined by standard methods involving dosing, the taking of blood samples at times intervals, and the assaying of the protein using ELISA, HPLC, radioassay, or other methods known in the art or as described herein, followed by standard calculations of the data to derive the half-life and other PK parameters.

The increases in half-life result in a reduction of the peak-to-trough concentration ratio, smoothening the concentration vs. time profile when multiple doses are delivered. The more consistent exposure can result in improved efficacy as well as a reduction in adverse events, which are often driven by a high $C_{max}$ (supratherapeutic concentrations). The extended duration of individual doses, also reduces the dose frequency, resulting in reduction of any delivery-related adverse events (such as injection site reactions), improved compliance, and added convenience for the patient.

Physicochemical and Pharmaceutical Properties

In addition to enhancing the PK properties of a therapeutic, fusion to a mucin-domain polypeptides may useful for improving the pharmaceutical or physicochemical properties (such as the degree of aqueous solubility) of the therapeutic active peptide or protein. Solubility improvements can be mediated both through addition of the highly hydrophilic carbohydrates on the mucin as well as through selection of the proper mucin-polypeptide sequence, which may additionally contain ionizable residues such as aspartic acid, glutamic acid, histidine, lysine, and arginine. The ionizable residues result in the modulation of the pI of the fusion protein and thereby the total charge of the protein in a particular formulation.

The fusion proteins of the invention can be constructed and assayed, using methods described herein, to confirm the physicochemical properties of the fusion protein result in the desired properties. In one embodiment, the mucin-domain polypeptide is selected such that the fusion protein has an aqueous solubility that is within at least about 25% greater compared to a therapeutic active protein not linked to the fusion protein, or at least about 30%, or at least about 40%, or at least about 50%, or at least about 75%, or at least about 100%, or at least about 200%, or at least about 300%, or at least about 400%, or at least about 500%, or at least about 1000% greater than the corresponding therapeutic active protein not linked to the fusion protein. Preferred mucin-domain polypeptide sequences can have at least 80% sequence identity, or about 90%, or about 91%, or about 92%, or about 93%, or about 94%, or about 95%, or about 96%, or about 97%, or about 98%, or about 99%, to about 100% sequence identity to mucin-domain polypeptide selected from Table I.

Uses of the Fusion Proteins

In another aspect, the invention provides a method of for achieving a beneficial effect in a disease, disorder or condition mediated by therapeutic active protein. The present invention addresses disadvantages and/or limitations of therapeutic active proteins that have a relatively short terminal half-life and/or a narrow therapeutic window between the minimum effective dose and the maximum tolerated dose.

In one embodiment, the invention provides a method for achieving a beneficial affect in a subject comprising the step of administering to the subject a therapeutically- or prophylactically-effective amount of a fusion protein. The effective amount can produce a beneficial effect in helping to treat a disease or disorder. In some cases, the method for achieving a beneficial effect can include administering a therapeutically effective amount of a fusion protein composition to treat a subject for diseases and disease categories wherein a therapeutic protein or peptide not linked to a mucin-domain polypeptide exhibits a suboptimal half life. In other cases, the method for achieving a beneficial effect can include administering a therapeutically effective amount of a fusion protein composition to treat a subject for diseases and disease categories wherein a therapeutic protein or peptide does not exist. In still further cases, the method for achieving a beneficial effect can include administering a therapeutically effective amount of a fusion protein composition to treat a subject for diseases and disease categories wherein a therapeutic protein or peptide exhibits a suboptimal stimulatory or suboptimal inhibitory effect as an agonist or antagonist, respectively.

Diseases amenable to treatment by administration of the compositions of the invention include without limitation cancer, inflammatory diseases, arthritis, osteoporosis, infections in particular hepatitis, bacterial infections, viral infections, genetic diseases, pulmonary diseases, type 1 diabetes, type 2 diabetes, hormone-related disease, Alzheimer's disease, cardiac diseases, myocardial infarction, deep vain thrombosis, diseases of the circulatory system, hypertension, hypotension, allergies, pain relief, dwarfism and other growth disorders, intoxications, blot clotting diseases, diseases of the innate immune system, embolism, wound healing, healing of burns, Crohn's disease, asthma, ulcer, sepsis, glaucoma, cerebrovascular ischemia, respiratory distress syndrome, corneal ulcers, renal disease, diabetic foot ulcer, anemia, factor IX deficiency, factor VIII deficiency, factor VII deficiency, mucositis, dysphagia, thrombocyte disorder, lung embolism, infertility, hypogonadism, leucopenia, neutropenia, endometriosis, Gaucher disease, obesity, lysosome storage disease, AIDS, premenstrual syndrome, Turners syndrome, cachexia, muscular dystrophy, Huntington's disease, colitis, SARS, Kaposi sarcoma, liver tumor, breast tumor, glioma, Non-Hodgkin lymphoma, Chronic myelocytic leukemia; Hairy cell leukemia; Renal cell carcinoma; Liver tumor; Lymphoma; Melanoma, multiple sclerosis, Kaposis sarcoma, papilloma virus, emphysema, bronchitis, periodontal disease, dementia, parturition, non small cell lung cancer, pancreas tumor, prostate tumor, acromegaly, psoriasis, ovary tumor, Fabry disease, lysosome storage disease.

In one embodiment, the method comprises administering a therapeutically-effective amount of a pharmaceutical composition comprising a fusion protein comprising a therapeutic active protein linked to an mucin-domain polypeptide and at least one pharmaceutically acceptable carrier to a subject in need thereof that results in greater improvement in at least one parameter, physiologic condition, or clinical outcome mediated by the therapeutic active protein of the fusion protein compared to the effect mediated by administration of a pharmaceutical composition comprising a therapeutic active protein not linked to mucin-domain polypeptide administered at a comparable dose. In one embodiment, the pharmaceutical composition is administered at a therapeutically effective dose. In another embodiment, the pharmaceutical composition is administered using multiple simultaneous or sequential doses using a therapeutically effective dose regimen (as defined herein) for the length of the dosing period.

As a result of the enhanced pharmacokinetic parameters of the fusion protein, as described herein such as extended half-life, the therapeutic active protein linked to a mucin-domain polypeptide may be administered using longer intervals between doses compared to the corresponding therapeutic active protein not linked to mucin-domain polypeptide to prevent, treat, alleviate, reverse or ameliorate symptoms or clinical abnormalities of the disease, disorder or condition or prolong the survival of the subject being treated.

A therapeutically effective amount of a fusion protein may vary according to factors such as the disease state, age, sex, and weight of the individual, and the ability of the antibody or antibody portion to elicit a desired response in the individual. A therapeutically effective amount is also one in which any toxic or detrimental effects of the fusion protein are outweighed by the therapeutically beneficial effects. A prophylactically effective amount refers to an amount of fusion protein required for the period of time necessary to achieve the desired prophylactic result.

In one embodiment, a method of treatment comprises administration of a therapeutically effective dose of a pharmaceutical composition comprising a fusion protein of the invention to a subject in need thereof that results in an increase in the half-life of the therapeutic active protein as compared to a comparable dose of the therapeutic active protein not linked to a fusion polypeptide of the invention.

In another aspect, the invention provides methods of making fusion proteins to improve ease of manufacture relative half-life extension technologies requiring post-expression chemical coupling, and result in increased stability, increased water solubility, and/or ease of formulation, as compared to the native therapeutic active proteins. In one embodiment, the invention includes a method of increasing the aqueous solubility of a therapeutic active protein comprising the step of linking the therapeutic active protein to a mucin-domain polypeptide selected such that a higher concentration in soluble form of the resulting fusion can be achieved, under physiologic conditions or in a therapeutically acceptable formulation, compared to the therapeutic active protein not linked to a mucin-domain polypeptide. Factors that contribute to the property of mucin-domain polypeptide to confer increased water solubility of active protein when incorporated into a fusion protein include the high percentage of glycosylation, the type of glycans, and the charge on the amino acids of the mucin-domain polypeptide. In some embodiments, the method results in a fusion protein wherein the water solubility is at least about 50%, or at least about 60% greater, or at least about 70% greater, or at least about 80% greater, or at least about 90% greater, or at least about 100% greater, or at least about 150% greater, or at least about 200% greater, or at least about 400% greater, or at least about 600% greater, or at least about 800% greater, or at least about 1000% greater, or at least about 2000% greater, or at least about 4000% greater, or at least about 6000% greater under physiologic conditions, or in a therapeutically acceptable formulation, compared to the native therapeutic active protein.

Nucleic Acid Sequences

The present invention provides isolated polynucleic acids encoding fusion proteins and sequences complementary to polynucleic acid molecules encoding fusion proteins of the invention. In another aspect, the invention encompasses methods to produce polynucleic acids encoding fusion proteins of the invention and sequences complementary to fusion proteins of the invention, including homologous variants. In general, the invention provides methods of producing a polynucleotide sequence coding for a fusion protein and expressing the resulting gene product include assembling nucleotides encoding each of the mucin-domain polypeptides and active proteins, linking the components in frame, incorporating the encoding gene into an appropriate expression vector, transforming an appropriate host cell with the expression vector, and causing the fusion protein to be expressed in the transformed host cell, thereby producing the fusion protein of the invention. Standard recombinant techniques in molecular biology can be used to make the polynucleotides and expression vectors of the present invention. In accordance with the invention, nucleic acid sequences that encode a fusion protein may be used to generate recombinant DNA molecules that direct the expression of fusion proteins in appropriate host cells. Several cloning strategies are envisioned to be suitable for performing the present invention, many of which can be used to generate a construct that comprises a gene coding for a fusion protein or its complement. In one embodiment, the cloning strategy would be used to create a gene that encodes a monomeric fusion protein that comprises an active protein and a mucin-domain polypeptide. In the foregoing embodiments hereinabove described in this paragraph, the gene can further comprise nucleotides encoding spacer sequences that may also encode cleavage sequence(s).

In one approach, a construct is first prepared containing the DNA sequence corresponding to a fusion protein. DNA encoding an active protein and/or a mucin polypeptide domain may be obtained from a cDNA library prepared using standard methods from tissue or isolated cells believed to possess the mRNA of an active protein and to express it at a detectable level. If necessary, the coding sequence can be obtained using conventional primer extension procedures as described in Sambrook, et al., supra, to detect precursors and processing intermediates of mRNA that may not have been reverse-transcribed into cDNA. Accordingly, DNA can be conveniently obtained from a cDNA library prepared from such sources. The encoding gene(s) may also be obtained from a genomic library or created by standard synthetic procedures known in the art (e.g., automated nucleic acid synthesis) using DNA sequences obtained from publicly available databases, patents, or literature references. Such procedures are well known in the art and well described in the scientific and patent literature. For example, sequences can be obtained from Chemical Abstracts Services (CAS) Registry Numbers (published by the American Chemical Society) and/or GenBank Accession Numbers available through the National Center for Biotechnology Information (NCBI) webpage, available on the world wide web at ncbi.nlm.nih.gov that correspond to entries in the CAS Registry or GenBank database that contain an amino acid sequence of the active protein or of a fragment or variant of the active protein or of the mucin-domain polypeptide.

A gene or polynucleotide encoding the active protein, for example can be then be cloned into a construct, which can be a plasmid or other vector under control of appropriate transcription and translation sequences for high level protein expression in a biological system. In a later step, a second gene or polynucleotide coding for the mucin-domain polypeptide for example is genetically fused to the nucleotides encoding the N- and/or C-terminus of the active protein gene by cloning it into the construct adjacent and in frame with the gene(s) coding for the active protein.

The resulting polynucleotides encoding the fusion polypeptides can then be individually cloned into an expression vector. The nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature.

Suitable vectors, hosts, and expression systems are well known to those skilled in the art of recombinant expression. Various vectors are publicly available. The vector may, for example, be in the form of a plasmid, cosmid, viral particle, or phage. Both expression and cloning vectors contain a nucleic acid sequence that enables the vector to replicate in one or more selected host cells, and further allows expression and post-translational modification of the recombinant protein within the host cell.

The present invention also provides a host cell for expressing the monomeric fusion protein compositions disclosed herein. Examples of suitable eukaryotic host cells include, but are not limited to yeast hosts such as *Saccharomyces cerevisiae, Pichia pastoris*, and *Hansenula polymorpha*; insect hosts such as *Spodoptera frugiperda* Sf9, *Spodoptera frugiperda* Sf21, and High Five cells; and mammalian hosts such as mouse fibroblast cells (C 127-BPV), Chinese hamster ovary cells (CHO-DHFR, CHO-NEO-SPLA, CHO-GS), and mouse myeloma cells (NSO-GS).

Expressed fusion proteins may be purified via methods known in the art or by methods disclosed herein. Procedures such as gel filtration, affinity purification, salt fractionation, ion exchange chromatography, size exclusion chromatography, hydroxyapatite adsorption chromatography, hydrophobic interaction chromatography and gel electrophoresis may be used; each tailored to recover and purify the fusion protein produced by the respective host cells. Methods of purification are described in Robert K. Scopes, Protein Purification: Principles and Practice, Charles R. Castor (ed.), Springer-Verlag 1994, and Sambrook, et al., supra. Multi-step purification separations are also described in Baron, et al., *Crit. Rev. Biotechnol.* 10:179-90 (1990) and Below, et al., *J. Chromatogr. A*. 679:67-83 (1994).

Pharmaceutical Compositions

The present invention provides pharmaceutical compositions comprising fusion proteins of the invention. In one embodiment, the pharmaceutical composition comprises the fusion protein and at least one pharmaceutically acceptable carrier. Fusion proteins of the present invention can be formulated according to known methods to prepare pharmaceutically useful compositions, whereby the polypeptide is combined with a pharmaceutically acceptable carrier vehicle, such as aqueous solutions or buffers, pharmaceutically acceptable suspensions and emulsions. Examples of non-aqueous solvents include propyl ethylene glycol, polyethylene glycol and vegetable oils. Therapeutic formulations are prepared for storage by mixing the active ingredient having the desired degree of purity with optional physiologically acceptable carriers, excipients or stabilizers, as described in Remington's Pharmaceutical Sciences 16th edition, Osol, A. Ed. (1980), in the form of lyophilized formulations or aqueous solutions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition, the pharmaceutical compositions can also contain other pharmaceutically active compounds or a plurality of compounds of the invention.

More particularly, the present pharmaceutical compositions may be administered for therapy by any suitable route including oral, rectal, nasal, topical (including transdermal, aerosol, buccal and sublingual), vaginal, parenteral (including subcutaneous, subcutaneous or intrathecally by infusion pump, intramuscular, intravenous and intradermal), intravitreal, and pulmonary. It will also be appreciated that the preferred route will vary with the therapeutic agent, condition and age of the recipient, and the disease being treated.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another preferred embodiment, the pharmaceutical composition is administered subcutaneously. In this embodiment, the composition may be supplied as a lyophilized powder to be reconstituted prior to administration. The composition may also be supplied in a liquid form, which can be administered directly to a patient. In one embodiment, the composition is supplied as a liquid in a pre-filled syringe such that a patient can easily self-administer the composition.

In another embodiment, the compositions of the present invention are encapsulated in liposomes, which have demonstrated utility in delivering beneficial active agents in a controlled manner over prolonged periods of time. Liposomes are closed bilayer membranes containing an entrapped aqueous volume. Liposomes may also be unilamellar vesicles possessing a single membrane bilayer or multilamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. In one embodiment, the liposome may be coated with a flexible water soluble polymer that avoids uptake by the organs of the mononuclear phagocyte system, primarily the liver and spleen. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilic peptide sequences as described in U.S. Pat. Nos. 6,316,024; 6,126,966; 6,056,973 and 6,043,094, the contents of which are incorporated by reference in their entirety.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phasphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino) propane (DOTAP); N-[1-(2,3,-ditetradecyloxy) propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3 [N—(N',N'-dimethylaminoethane)carbamoly] cholesterol (DC-Chol); or dimethyldioctadecylammonium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

For liquid formulations, a desired property is that the formulation be supplied in a form that can pass through a 25, 28, 30, 31, 32 gauge needle for intravenous, intramuscular, intraarticular, or subcutaneous administration.

In other embodiments, the composition may be delivered via intranasal, buccal, or sublingual routes to the brain to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs. Preparation of a pharmaceutical composition for delivery in a subdermally implantable device can be performed using methods known in the art, such as those described in, e.g., U.S. Pat. Nos. 3,992,518; 5,660,848; and 5,756,115.

EXAMPLES

The following examples are offered by way of illustration and are not to be construed as limiting the invention as claimed in any way.

Example 1. Design, Preparation, Expression, and Purification of Mucin Domain Fusion Constructs 1. Design of Mucinylated IL-1Ra Fusion Proteins Fusion proteins of IL-1Ra with varying lengths of mucinylation were designed. The length of the mucin domain was systematically increased by varying the number of mucin tandem repeats. The mucinylated domains of the fusion proteins were based on the tandem repeat (TR) from the human MUC20 protein. Fusion proteins of IL-1Ra with 2TR, 4TR, 6TR, 8TR, and 12TR were designed, designated RDB1813 [SEQ ID NO: 1 (protein); SEQ ID NO: 2 (DNA)], RDB1814 [SEQ ID NO: 3 (protein); SEQ ID NO: 4 (DNA)], RDB1826 [SEQ ID NO: 5 (protein); SEQ ID NO: 6 (DNA)], RDB1815 [SEQ ID NO: 7 (protein); SEQ ID NO: 8 (DNA)], and RDB1816 [SEQ ID NO: 9 (protein); SEQ ID NO: 10 (DNA)], respectively. A linker of 4 glycines (GGGG (SEQ ID NO: 27)) was inserted between the C-terminus of the IL-1Ra sequence and the first mucin TR, and between each set of 2 mucin TR. A His-tag was added to the C-terminus of RDB1813, RDB1814, RDB1815, and RDB1816, and a FLAG tag to the C-terminus of RDB1826 for ease of purification.

2. Design of Mucinylated Exendin-4 Fusion Protein RDB2203

A fusion protein of exendin-4 with 8TR from the human MUC20 protein was designed: RDB2203 [SEQ ID NO: 24]. A linker of 4 glycines (GGGG (SEQ ID NO: 27)) was inserted between the C-terminus of the exendin-4 sequence and the first mucin TR, and between each set of 2 mucin TR. A His-tag was added to the C-terminus for ease of purification, with a spacer (GGGGS (SEQ ID NO: 28)) between the final TR and the His-tag.

3. Gene Synthesis

Synthesis of the genes for expression of the designed constructs was carried out using standard methods.

4. Subcloning of the Synthesized Gene into a Mammalian Expression Vector

A) Preparation of the Expression Vector pcDNA™ (Invitrogen).

5 μg of pcDNA was digested with BamHI and HindIII for two hours at 37° C. The digest was treated with calf alkaline phosphatase to remove the 5' phosphate, thus preventing religation of vector on itself. Buffer was exchange to remove salts from calf alkaline phosphatase reaction. Qiagen's PCR cleanup kit was used following the manufacturer's suggested protocol. The DNA was eluted in 30 μl of H20.

B) Preparation of the Gene of Interest.

The gene of interest was digested with BamHI and HindIII for two hours 37° C. The digestion reaction was run on an E-Gel® CloneWell™ apparatus (Invitrogen) using 0.8% SYBR Green. The fragment corresponding to the gene of interest was isolated from the second row of wells on the gel.

C) Ligation Reaction of the Gene to pcDNA.

The prepared pcDNA (step A) was mixed with the DNA from step B in the presence of T4 ligase and incubated at room temperature for 30 minutes. Following the ligation, the products were transformed into TOP 10 cells (Invitrogen; chemically competent strain of E. coli) and the correct clone was picked and stored as a glycerol stock at the −80° C.

5. Expression of Mucinylated IL-1Ra and Exendin-4 Fusion Proteins

All the proteins were expressed in CHO cells using FreeStyle™ MAX Reagent (Invitrogen) following the manufacturer's protocol. Briefly, a day prior to transfection the cells were seeded at $0.5 \times 10^6$ cells/mL, and on the day of transfection they were adjusted to $1 \times 10^6$ cells/mL as recommended by manufacturer. For a 1 liter transfection, two tubes (A and B) of media (OptiPRO™, Invitrogen) were prepared, each containing about 19 ml. 1 mg of DNA was added to tube A, and 1 ml of FreeStyle™ MAX Reagent was added to tube B. Immediately the contents of both tubes were mixed and incubated at room temperature for 15 minutes. After the incubation period the mixture was added slowly to the 1 liter of CHO cells. After transfection, the cells were left for 6 to 7 days and then the supernatant was collected.

6. Purification of Mucinylated IL-1Ra and Exendin-4 Fusion Proteins

Purification of the His-tagged expressed proteins was carried out on a nickel column. After binding the protein, the column was washed with up to 5 column volumes of buffer A (50 mM Tris pH8 and 500 mM NaCl). The bound protein was eluted with an increasing concentration of imidazole (20 to 500 mM). The purified protein was dialyzed overnight against PBS.

RDB1826 was purified on an anti-FLAG column. After binding the protein, the column was washed with up to 5 column volumes of PBS. The protein was eluted at pH3 and directly neutralized with Tris buffer pH7. The purified protein was dialyzed overnight against PBS.

Example 2. Molecular Weights and pIs of Mucin-IL-1Ra Constructs

IL-1Ra-mucin fusion proteins RDB1813 (IL1Ra 2TR), RDB1814 (IL1Ra 4TR), RDB1815 (IL1Ra 8TR), and RDB1816 (IL1Ra 12TR) were characterized using SDS/PAGE (FIG. 1A). The apparent molecular weight of all the constructs is significantly higher than the calculated molecular weight of the polypeptide sequence, consistent with the expected high level of glycosylation. The respective calculated molecular weights of the polypeptides for RDB1813, RDB1814, RDB1815, and RDB1816 are 22 kD, 26.2 kD, 34.8 kD, and 43.3 kD, and their respective apparent molecular weights based on their mobility on the gel are 35 kD, 45 kD, 65 kD, and 80 kD (FIG. 1A; arrows).

The isoelectric points of constructs RDB1813 (IL1Ra 2TR), RDB1826 (IL1Ra 6TR), RDB1815 (IL1Ra 8TR), and RDB1816 (IL1Ra 12TR) were measured using isoelectric focusing (FIG. 1B). All constructs were heterogenous with respect to charge, with multiple bands around the PI of the protein. The PI's of the protein were largely in line with their calculated PI's based on the polypeptide sequence, suggesting the O-glycans are not heavily sialylated. The multiplicity of bands is most likely due to differences in N-glycosylation.

All constructs were further characterized by analytical gel filtration on a Superdex 200 column (FIGS. 2-6). Gel filtration separates proteins based on their hydrodynamic volume under native conditions (i.e. unlike SDS/PAGE, it is non-denaturing). Elution times can be calibrated with globular protein standards such that the apparent molecular weight for an unknown globular protein can be calculated. As elution time is more directly related to hydrodynamic radius rather than actual molecular weight, apparent molecular weights which are significantly higher than their calculated molecular weights suggest non-globular (ie, elongated or rod-like) structures, high levels of glycosylation, and/or high levels of hydration.

On gel filtration, the apparent molecular weights for RDB1813, RDB1814, RDB1826, RDB1815, and RDB1816 are, 42 kD, 50 kD, 118 kD, 139 kD, and 230 kD, respectively (FIGS. 2-6). The apparent molecular weights of all the mucin constructs were significantly higher than both their calculated molecular weights (based upon the amino acid sequence alone) and their mobility on SDS/PAGE. These observations are highly consistent with both the high level of glycosylation and the expected rod-like structure of the mucin constructs.

Example 3. Antagonist Activities of Mucin-IL-1Ra Constructs

HEK-Blue™ IL-1β cells (Invivogen) are human embryonic kidney cells specifically designed to detect bioactive IL-1β in vitro by monitoring the IL-1β-induced expression of an NF-κB/AP-1 secreted embryonic alkaline phosphatase (SEAP) reporter gene. SEAP can be readily monitored when using the SEAP detection medium QUANTI-Blue™ (Invivogen). IL-1Ra inhibits this IL-1β-induced signal through binding IL-1RI, preventing the binding of IL-1RAcP, and thus assembly of the full signaling complex. The ability of the mucin-IL1Ra constructs RDB1813 (IL1Ra 2TR), RDB1814 (IL1Ra 4TR), RDB1826 (IL1Ra 6TR), RDB1815 (IL1Ra 8TR), and RDB1816 (IL1Ra 12TR) to inhibit IL-1β-induced SEAP was evaluated. IL1Ra (anakinra) that lacks a fused mucin domain was used as a positive antagonist control.

100 μL of media containing HEK-Blue™ IL-1β cells were plated into 96-well microtiter plates to a final concentration of 50,000 cells/well. Mucin-IL1Ra constructs RDB1813 (IL1Ra 2TR), RDB1814 (IL1Ra 4TR), RDB1826 (IL1Ra 6TR), RDB1815 (IL1Ra 8TR), and RDB1816 (IL1Ra 12TR) were prepared at initial concentrations of 12 nM (RDB1813), 4.8 nM (RDB1814), 34.5 nM (RDB1826), 2.4 nM (RDB1815), and 11.6 nM (RDB1816), then serially diluted and added in duplicate test samples to the HEK-Blue™ IL-1β cells. IL-1β at 0.015 nM was used in all test samples to induce SEAP. 0.117 nM IL-1β alone, and 11.76 nM IL1Ra+0.015 nM IL-1β were used in control samples. The samples were incubated at 37° C., for 20-24 hours and evaluated using the QUANTI-Blue™ assay.

Figure 7:
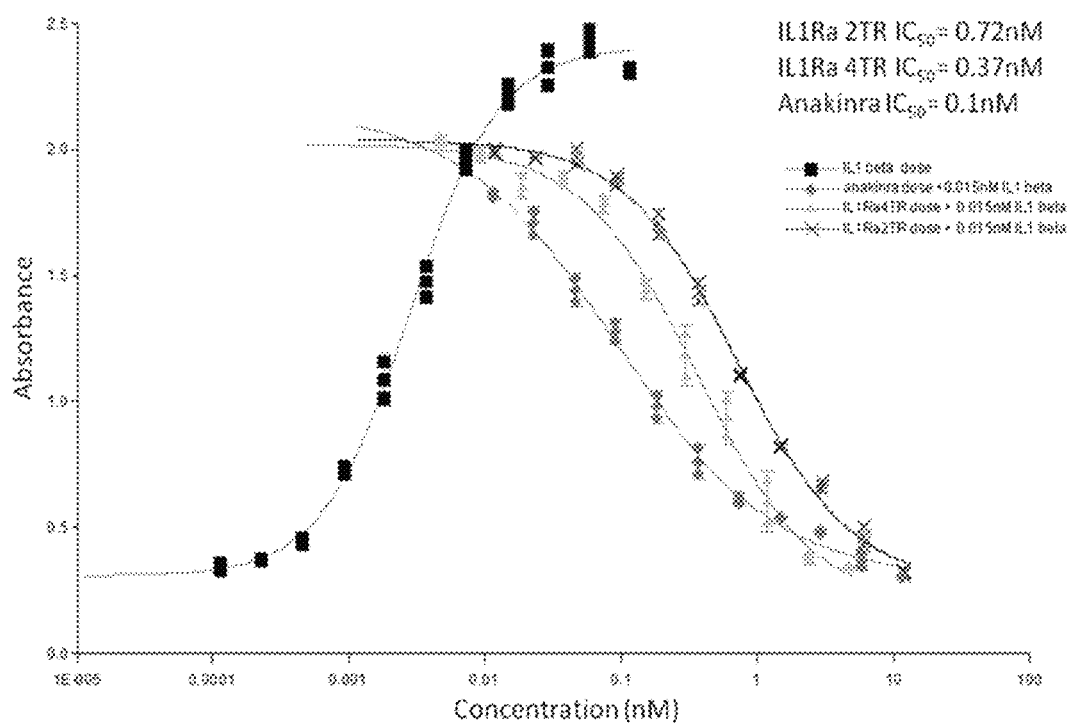
FIG. 7 Inhibition of IL1β signaling by RDB1813 (2TR) and RDB1814 (4TR) in the HEK-blue assay. Activity of IL1β (—■—) as a function of its concentration in the absence of inhibition. Inhibition by RDB1813 (-✱-), RDB1814 (—▲—) and IL1Ra (Anakinra —◆—) were measured in the presence of 15 pM of IL1β. All measurements were made in duplicate. Estimated values of $IC_{50}$ are reported in the top right corner of the figure.
Figure 8:
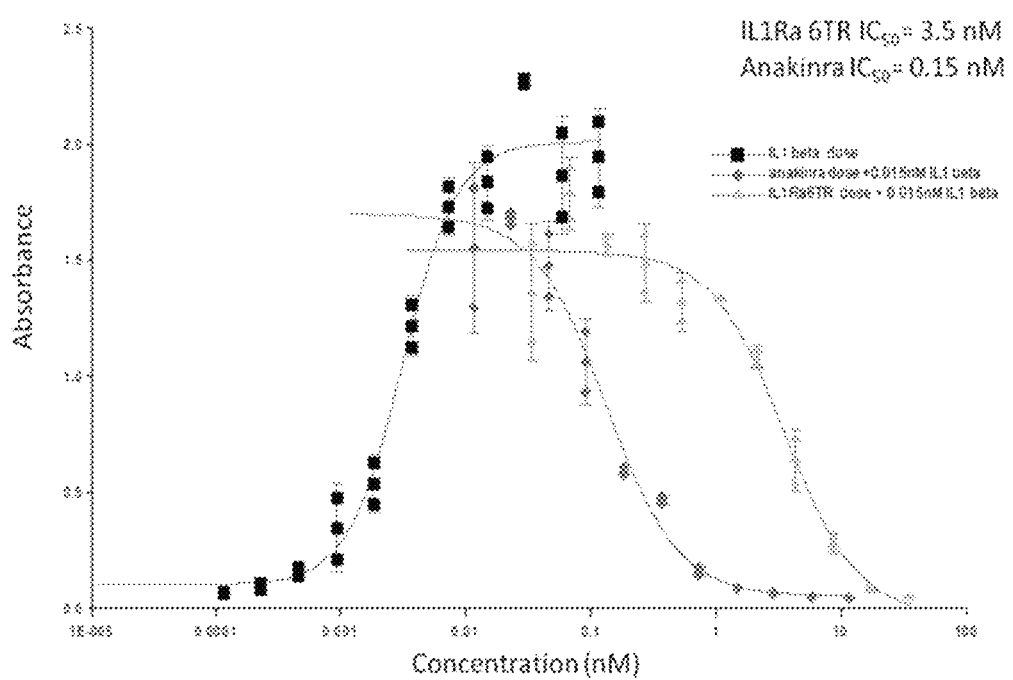
FIG. 8. Inhibition of IL1β signaling by RDB1826 (6TR) in the HEK-blue assay. Activity of IL1β (—■—) as a function of its concentration in the absence of inhibition. Inhibition by RDB1826 (—▲—) and IL1Ra (Anakinra —◆—) were measured in the presence of 15 pM of IL1β. All measurements were made in duplicate. Estimated values of $IC_{50}$ are reported in the top right corner of the figure.
Figure 9:
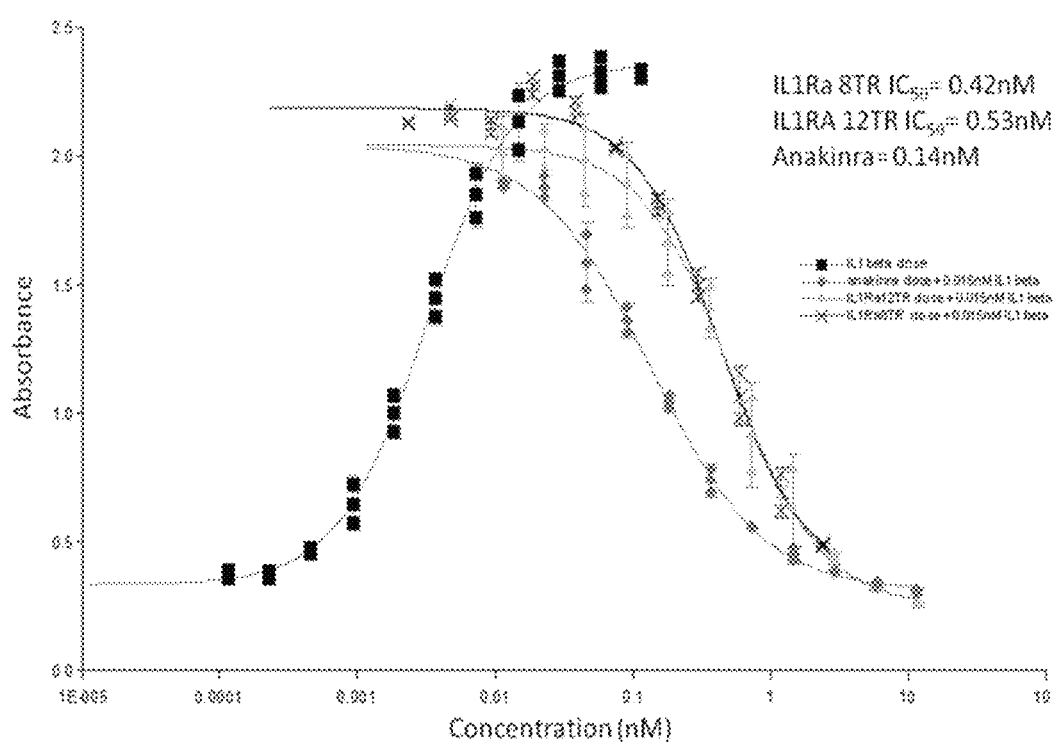
FIG. 9 Inhibition of IL1β signaling by RDB1815 (8TR) and RDB1816 (12TR) in the HEK-blue assay. Activity of IL1β (—■—) as a function of its concentration in the absence of inhibition. Inhibition by RDB1815 (-✱-), RDB1816 (—▲—) and IL (Anakinra —◆—) were measured in the presence of 15 pM of IL1β. All measurements were made in duplicate. Estimated values of $IC_{50}$ are reported in the top right corner of the figure.
Figure 10:
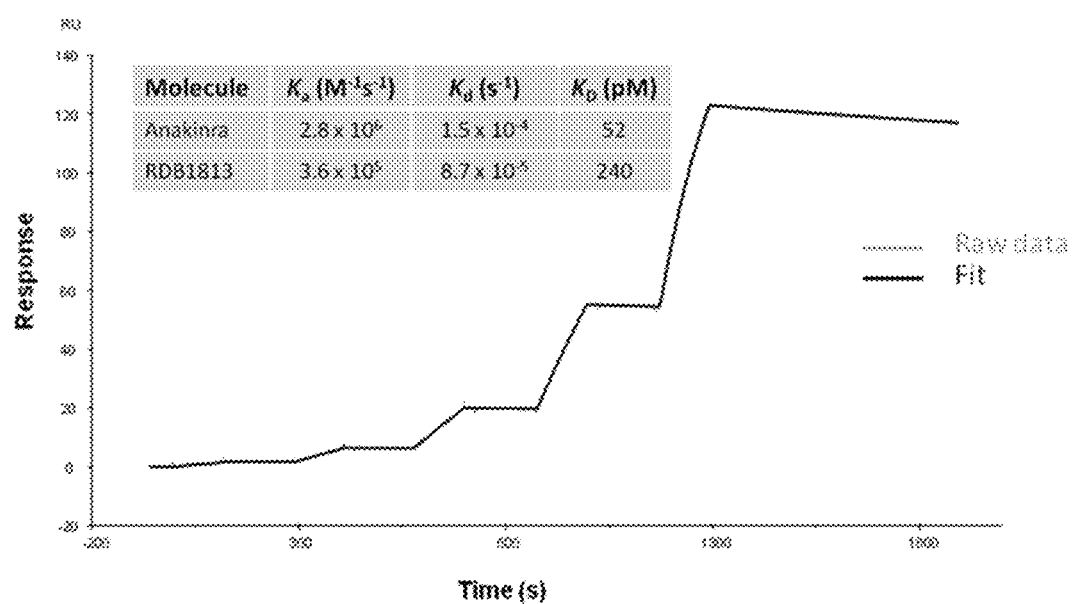
FIG. 10. Surface Plasmon Resonance (SPR) measurements of RDB1813 binding to immobilized mouse IL1RI receptor. Sensorgrams and fitted curves are in grey and black, respectively. The kinetic parameters for RDB1813 and Anakinra (data not shown) are in the inset.
Figure 11:
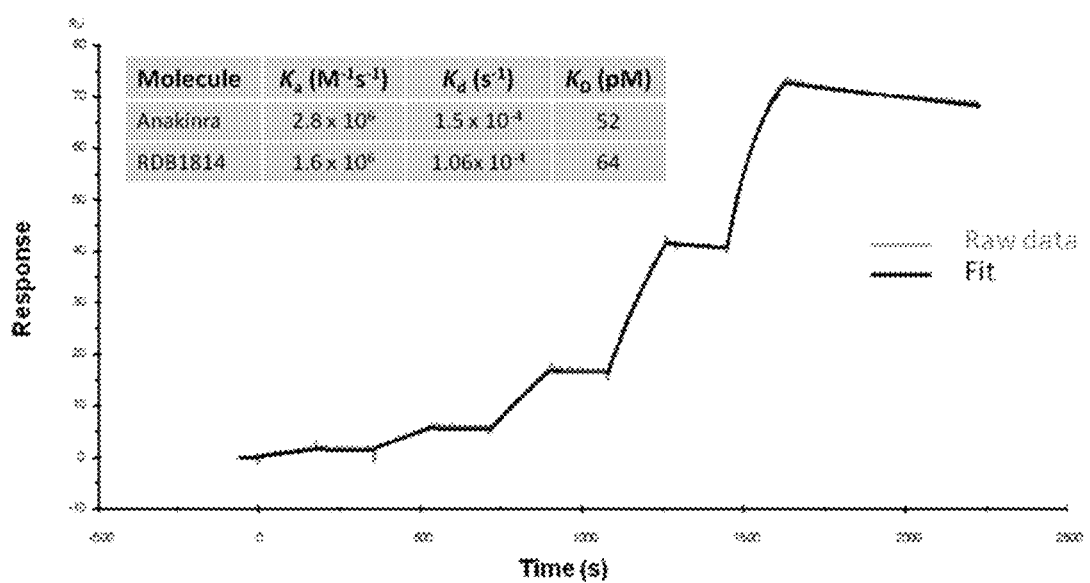
FIG. 11. Surface Plasmon Resonance (SPR) measurements of RDB1814 binding to immobilized mouse IL1RI receptor. Sensorgrams and fitted curves are in grey and black, respectively. The kinetic parameters for RDB1814 and Anakinra (data not shown) are in the inset.
Figure 12:
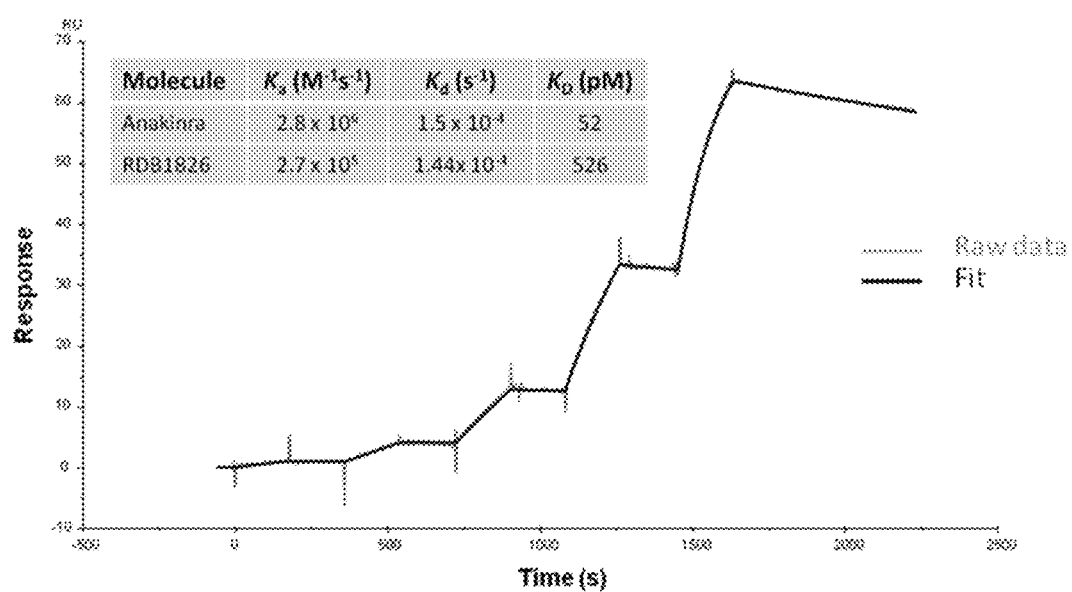
FIG. 12. Surface Plasmon Resonance (SPR) measurements of RDB1826 binding to immobilized mouse IL1RI receptor. Sensorgrams and fitted curves are in grey and black, respectively. The kinetic parameters for RDB1826 and Anakinra (data not shown) are in the inset.
Figure 13:
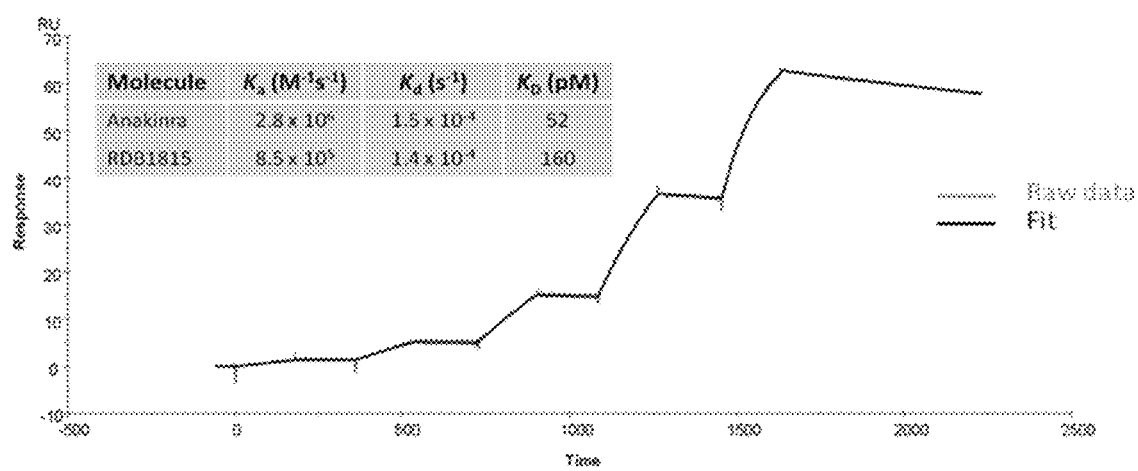
FIG. 13. Surface Plasmon Resonance (SPR) measurements of RDB1815 binding to immobilized mouse IL1RI receptor. Sensorgrams and fitted curves are in grey and black, respectively. The kinetic parameters for RDB1815 and Anakinra (data not shown) are in the inset.

Mucin-IL1Ra constructs RDB1813 (IL1Ra 2TR), RDB1814 (IL1Ra 4TR), RDB1826 (IL1Ra 6TR), RDB1815 (IL1Ra 8TR), and RDB1816 (IL1Ra 12TR) inhibited IL-1β-induced SEAP expression in a dose-dependent fashion, with $IC_{50}$ values of 0.72 nM, 0.37 nM, 3.5 nM, 0.42 nM, and 0.53 nM, respectively, comparing favorably with the control (unmodified IL1Ra) $IC_{50}$ value of 0.1-0.15 nM (FIGS. 7-9). Thus, the inhibitory activity of all mucinlylated constructs is within a few fold of the unmodified IL (non-mucinylated) protein control.

Example 4. Binding Affinity of Mucin-IL-1Ra to IL-1RI

IL-1RI_Fc (fusion protein) was immobilized on a Biacore™ Sensor Chip using the Human Antibody Capture Kit (GE Healthcare). Unmodified IL-1Ra (positive binding control), RDB1813 (IL1Ra 2TR), RDB1814 (IL1Ra 4TR), RDB1815 (IL1Ra 8TR), RDB1816 (IL1Ra 12TR), and RDB1826 (IL1Ra 6TR) were flowed over the chip at 5 concentrations: 20 nM, 6.6 nM, 2.2 nM, 0.74 nM and 0.24 nM. In the First cycle, the 0.24 nM concentration of the specific construct was flowed over the bound ligand on the surface of the chip for 180 seconds, after which a blank solution was passed over the surface to allow the analyte to dissociate. The same procedure was repeated for an additional four times using an increasing concentration from 0.74 to 20 nM for each construct. The resulting sensorgrams were analyzed with the native instrument software to calculate the binding affinities of the constructs (FIGS. 10-14).

Figure 14:
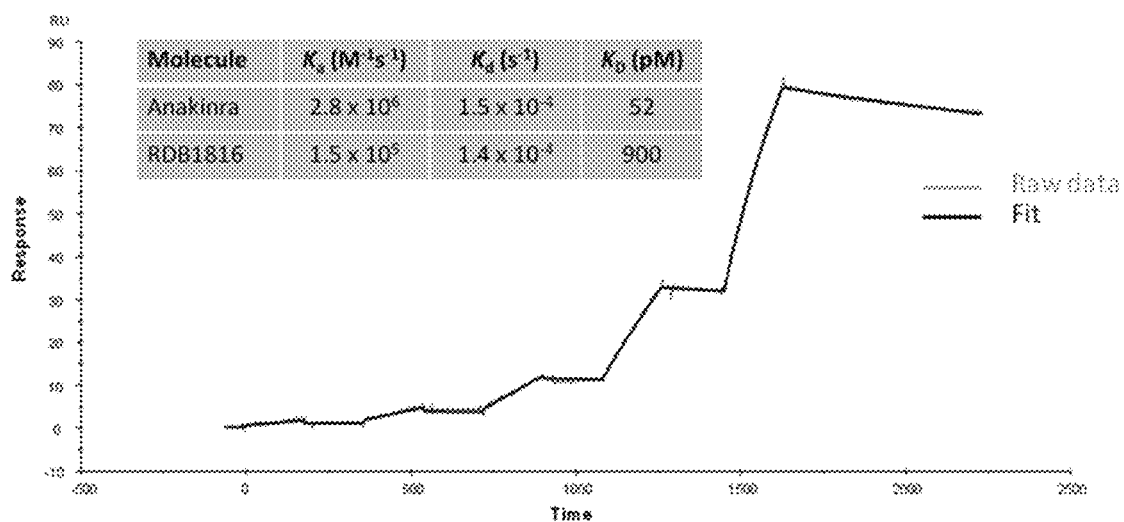
FIG. 14. Surface Plasmon Resonance (SPR) measurements of RDB1816 binding to immobilized mouse IL1RI receptor. Sensorgrams and fitted curves are in grey and black, respectively. The kinetic parameters for RDB1816 and Anakinra (data not shown) are in the inset.

Consistent with their activity data from the cell-based assay, all the constructs retained potent binding affinity for IL-1RI. The calculated binding constants ($K_D$) to IL-1RI for RDB1813 (IL1Ra 2TR), RDB1814 (IL1Ra 4TR), RDB1826 (IL1Ra 6TR), RDB1815 (IL1Ra 8TR), and RDB1816 (IL1Ra 12TR) were 240 pM, 64 pM, 526 pM, 160 pM, and 900 pM, respectively. Thus, the binding affinities of the mucinylated constructs are 4.6-fold (RDB1813), 1.2-fold (RDB1814), 10-fold (RDB1826), 3.1-fold (RDB1815), and 17.3-fold (RDB1816) higher than the unmodified IL-1Ra, whose $K_D$ was determined to be 52 pM. It is important to note that the construct with the weakest affinity to IL-1 RI (i.e. RDB1816) had the largest number of mucin tandem repeats in the series (12TR). RDB1816's loss in affinity was therefore entirely due to a slower association rate ($K_a$=1.5× $10^5$) when compared with unmodified IL-1Ra ($K_a$=2.8× $10^6$), perhaps due to a slower tumbling rate, as the dissociation rate ($K_d$) of RDB1816 ($K_d$=1.4×$10^{-4}$) was the same as for the unmodified IL-1Ra ($K_d$=1.5×$10^{-4}$) (FIG. 14).

Example 5. In Vivo Efficacy of RDB1816

The efficacy and duration of action of RDB1816 (IL1Ra 12TR) was evaluated in the mouse collagen-antibody-induced-arthritis (CAIA) model. Unmodified IL-1Ra is active in this model when continuously infused at a rate of 6 mg/kg/hr, but has no effect as a single 20 mg/kg dose due to its extremely short half-life.

Figure 15:
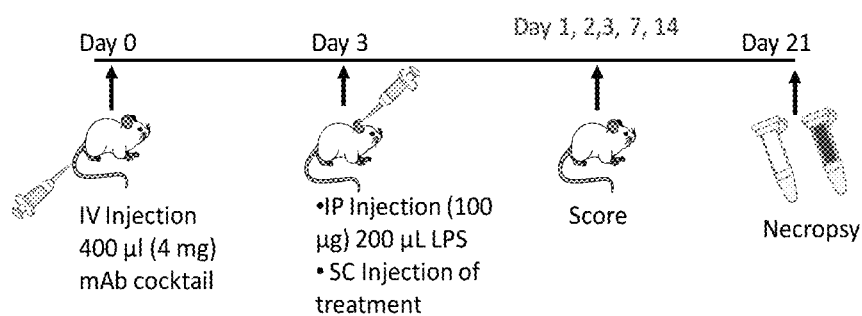
FIG. 15. Experimental design for evaluation of RDB1816 in the mouse CAIA model of inflammation.

The experimental design for the mouse CAIA model is depicted in FIG. 15, with an n of 8 mice per group. Briefly, arthritis is initiated in the mice by intravenous (IV) injection of an anti-collagen antibody cocktail. After 3 days, the inflammatory response was boosted with an intraperitoneal (IP) injection of lipopolysaccharide (LPS), while at the same time, the test compounds RDB1816 (20 mg/kg) and anakinra (unmodified IL-1Ra, 20 mg/kg), and a saline control were delivered subcutaneously (SC). Paw volume was measured across multiple days to assess the degree of inflammation.

Figure 16:
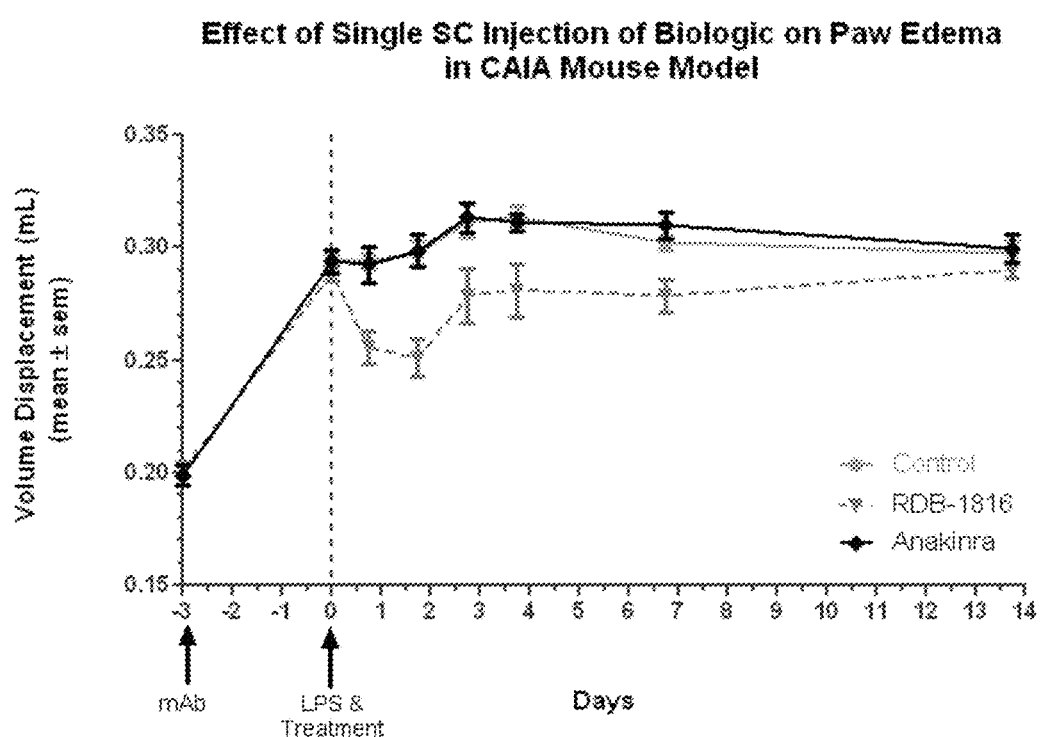
FIG. 16. The inhibitory effects of a single 20 mg/kg injection of RDB1816 (✧), IL1Ra (Anakinra ◆), and saline control (✱) in the mouse CAIA model of inflammation. The black arrows indicate the days of injection with the monoclonal antibody cocktail (mAb) and with LPS and treatment molecule. A group of eight mice were used for each treatment and each time point represents the mean from each group.

The results of the mouse CAIA experiment are depicted in FIG. 16. The anakinra-treated group showed no reduction in inflammation relative to the saline control. This is due to its short half-life resulting in low exposure, as a continuous infusion of anakinra is efficacious in this model. In marked contrast, significant reduction in paw volume was observed in the RDB1816-treated mice relative to both the saline-treated and the anakinra-treated groups. Thus, mucinylation sufficiently increased the exposure of the IL-1Ra molecule to elicit a pharmacodynamic effect.

Example 6. Pharmacokinetics (PK) of RDB1815 and RDB1816

A pharmacokinetic study in rats was conducted to determine the half life of two IL-1Ra-mucin fusion polypeptide constructs: RDB1815 and RDB1816. A single dose of RDB1815 was delivered subcutaneously (5.6 mg/Kg) or intravenously (2.1 mg/Kg), and a single dose of RDB1816 was delivered subcutaneously (6.4 mg/Kg) or intravenously (2.4 mg/Kg), with an n=3 rats per dosage group. Blood was collected at various time points over 6 days and analyzed for IL-1Ra by ELISA.

Figure 17:
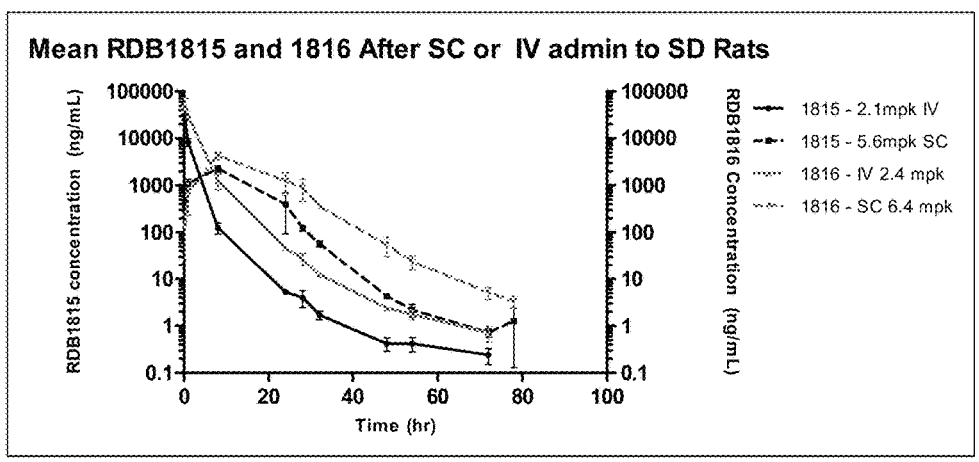
FIG. 17. Pharmacokinetic profile of RDB1815 and RDB186 in rat. The plasma concentration-time profiles are recorded for RDB1815 i.v. (—●—), single injection of 2.1 mg/Kg [mpk]), SC injection (-■-, single injection of 5.6 mpk) and for RDB1816 i.v. (—▼—, single injection 2.4 mpk), SC injection (···, single injection 6.4 mpk). Symbols represent the mean from three different rats per condition. Pharmacokinetic parameters for the SC groups are summarized in the table.

From the pharmacokinetic data (FIG. 17), half lives of 17.9 h and 13.9 h were calculated for RDB1815 and RDB1816, respectively when by IV, and 11.0 h and 8.0 h, respectively when delivered by SC. This represents an extension of half life between 10-fold and 14-fold over reported values for the unmodified IL-1Ra control (Anakinra) Consequently, the exposure of both RDB1815 and RDB1816 are dramatically increased, consistent with the efficacy observed in the mouse CAIA model.

Example 7. Molecular Weight of Mucin-Exendin-4 Construct RDB2203

Figure 18:
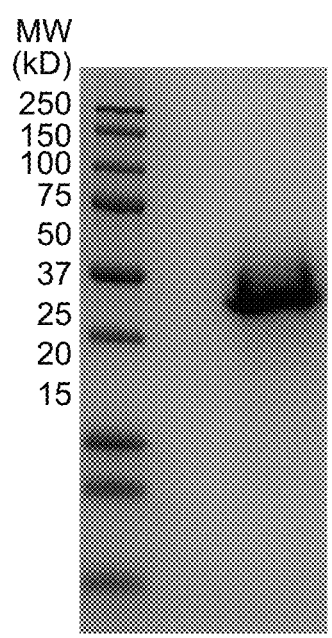
FIG. 18. Coomassie Blue-stained SDS/polyacrylamide gel of exendin-4 mucin construct RDB2203.
Figure 19:
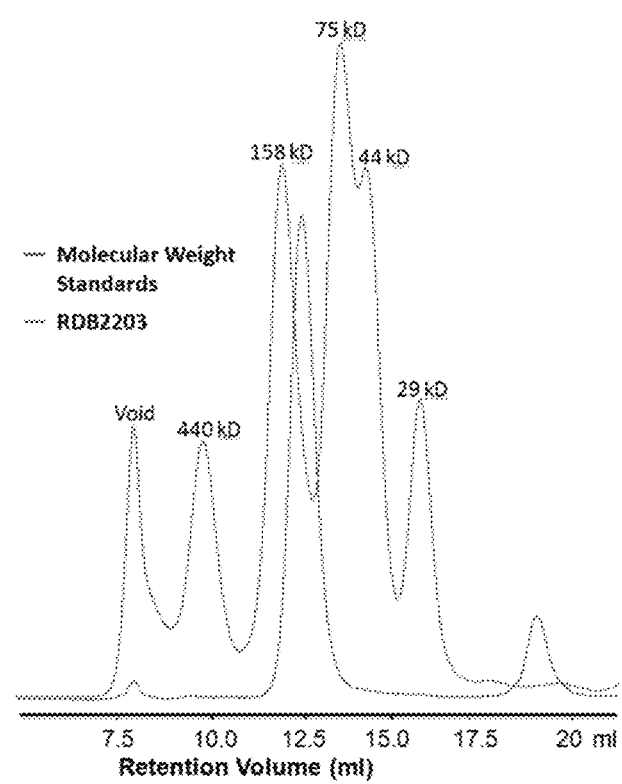
FIG. 19. Gel filtration chromatogram of RDB2203 (grey) and molecular size standards (grey). Molecular weights of the standards are listed above each eluting peak.

RDB2203 was characterized using SDS/PAGE and analytical gel filtration on a Superdex 200 column. By SDS/PAGE, the apparent molecular weight of RDB2203 is about 45 kD, about twice its calculated polypeptide molecular weight of 22.8 kD, consistent with a high level of glycosylation (FIG. 18: molecular markers on the left). By analytical gel filtration, the apparent molecular weight of RDB2203 is 120 kD (single peak between the 158 kD and 75 kD standards), due to the large hydrodynamic radius imparted by the highly glycosylated mucin domain (FIG. 19).

Example 8. Bioactivity of RDB2203

Figure 20:
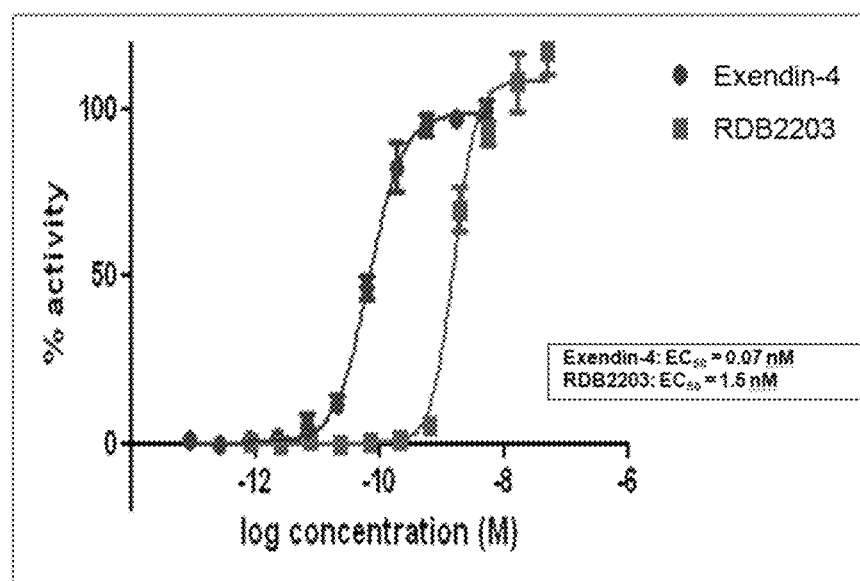
FIG. 20. GLP-1R activity assay for RDB2203 and exendin-4.

The ability of RDB2203 to agonize the GLP-1 receptor was measured using the DiscoveRx PathHunter eXpress GLP-1 receptor cAMP assay. The assay was executed as per the manufacturer's instructions. The results indicate that RDB2203 is a potent agonist of the GLP-1 receptor, demonstrating an $EC_{50}$ of 1.5 nM, which is about 21-fold less potent than the unmodified exendin-4 ($EC_{50}$ of 0.07 nM) (FIG. 20).

Example 9. Pharmacokinetic Profile of RDB2203

Figure 21:
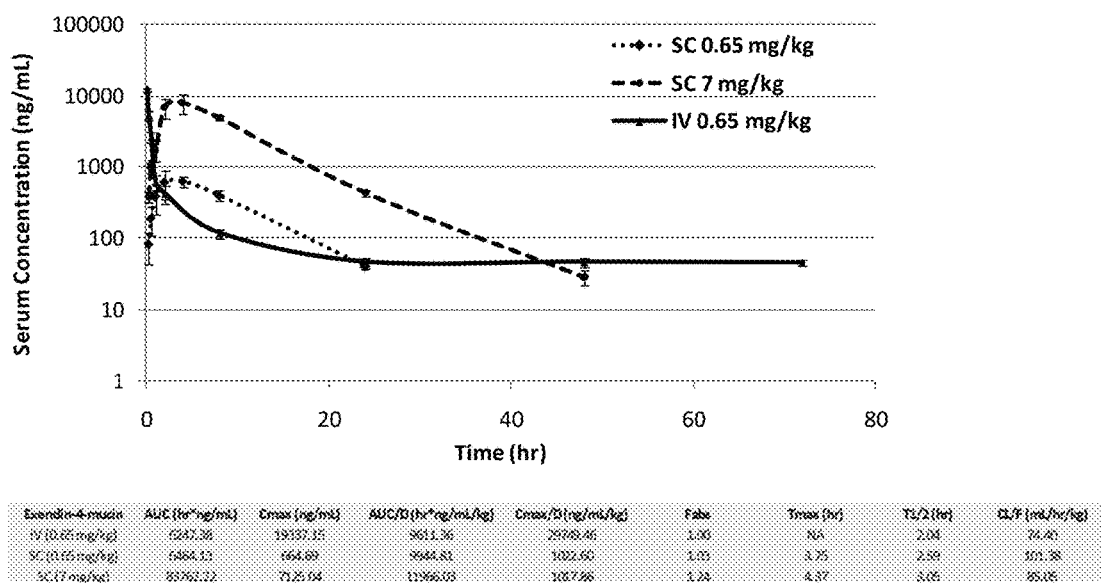
FIG. 21. Pharmacokinetic profile of RDB2203.

RDB2203 was dosed in rats intravenously at 0.65 mg/kg and subcutaneously at 0.65 mg/kg and 7.0 mg/kg. Relative to the un-mucinylated exendin-4[1], RDB2203 exhibited an increase in half-life (2.0 hr vs. 0.5 hr, iv) and reduced clearance (74 ml/hr/kg vs. 200 ml/hr/kg, iv), resulting in an increase in total exposure [[1] Ai, G., et al.; Pharmacokinetics of exendin-4 in Wistar rats; Journal of Chinese Pharmaceutical Sciences; 17 (2008) 6-10] (FIG. 21). Via the subcutaneous route, RDB2203 also displayed improved bioavailability, >95% relative to 65% for the unmodified exendin-4 (FIG. 21).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

SEQUENCE LISTING
1)
PRT
RDB1813
1
SARRPSGRKS SKMQAFRIWD VNQKTFYLRN NQLVAGYLQG
PNVNLEEKID VVPIEPHALF LGIHGGKMCL SCVKSGDETR
LQLEAVNITD LSENRKQDKR FAFIRSDSGP TTSFESAACP
GWFLCTAMEA DQPVSLTNMP DEGVMVTKFY FQEDEGGGGS
ASSESSASSD GPHPVITESR ASSESSASSD GPHPVITESR
GSSHHHHHH

2)
DNA
RDB1813
1
TCCGCTCGAC GACCTTCTGG GCGAAAATCT TCTAAAATGC
AGGCCTTCCG GATTTGGGAT GTGAATCAGA AAACTTTTTA
CCTGAGGAAC AACCAGCTGG TCGCTGGATA CCTGCAGGGA
CCAAACGTGA ATCTGGAGGA GAAAATCGAC GTCGTCCCAA
TCGAACCTCA CGCTCTGTTT CTGGGAATCC ATGGCGGCAA
AATGTGTCTG TCCTGTGTGA AATCTGGCGA CGAGACTAGA
CTGCAGCTGG AGGCTGTGAA TATCACCGAC CTGTCTGAGA
ATCGTAAACA GGACAAACGC TTTGCCTTTA TCCGCTCCGA
TAGTGGACCA ACAACCTCTT TCGAATCTGC TGCTTGCCCT
GGATGGTTTC TGTGTACCGC TATGGAGGCC GATCAGCCTG
TGTCTCTGAC CAATATGCCC GATGAGGGAG TCATGGTGAC
AAAATTCTAC TTTCAGGAGG ATGAGGGCGG AGGCGGTTCT
GCTAGTAGCG AGTCCTCTGC TTCTTCCGAT GGACCTCACC
CCGTGATTAC CGAATCCCGA GCTTCTTCCG AATCTTCTGC
CTCTTCCGAC GGCCCACACC CTGTCATCAC TGAGAGCCGT
GGTTCATCAC ACCACCATCA TCACCACTAG TGA

3)
PRT
RDB1814
1
SARRPSGRKS SKMQAFRIWD VNQKTFYLRN NQLVAGYLQG
PNVNLEEKID VVPIEPHALF LGIHGGKMCL SCVKSGDETR
LQLEAVNITD LSENRKQDKR FAFIRSDSGP TTSFESAACP
GWFLCTAMEA DQPVSLTNMP DEGVMVTKFY FQEDEGGGGS
ASSESSASSD GPHPVITESR ASSESSASSD GPHPVITESR
GGGGSASSES SASSDGPHPV ITESRASSES SASSDGPHPV
ITESRGSSHH HHHH

4)
DNA
RDB1814
1
TCCGCTCGAC GACCTTCTGG GCGAAAATCT TCTAAAATGC
AGGCCTTCCG GATTTGGGAT GTGAATCAGA AAACTTTTTA
CCTGAGGAAC AACCAGCTGG TCGCTGGATA CCTGCAGGGA
CCAAACGTGA ATCTGGAGGA GAAAATCGAC GTCGTCCCAA
TCGAACCTCA CGCTCTGTTT CTGGGAATCC ATGGCGGCAA
AATGTGTCTG TCCTGTGTGA AATCTGGCGA CGAGACTAGA
CTGCAGCTGG AGGCTGTGAA TATCACCGAC CTGTCTGAGA
ATCGTAAACA GGACAAACGC TTTGCCTTTA TCCGCTCCGA
TAGTGGACCA ACAACCTCTT TCGAATCTGC TGCTTGCCCT
GGATGGTTTC TGTGTACCGC TATGGAGGCC GATCAGCCTG
TGTCTCTGAC CAATATGCCC GATGAGGGAG TCATGGTGAC
AAAATTCTAC TTTCAGGAGG ATGAGGGCGG AGGCGGTTCT
GCTAGTAGCG AGTCCTCTGC TTCTTCCGAT GGACCTCACC
CCGTGATTAC CGAATCCCGA GCTTCTTCCG AATCTTCTGC
CTCTTCCGAC GGCCCACACC CTGTCATCAC TGAGAGCCGT
GGTGGCGGTG GATCTGCTAG TAGTGAATCA TCTGCTAGTA
GTGACGGCCC ACACCCCGTG ATTACTGAGA GTCGTGCCTC
TTCCGAATCA TCTGCTAGTA GTGACGGACC TCACCCCGTG
ATCACTGAGT CCCGTGGCTC ATCACCAC CATCATCACC
ACTAGTGA

5)
PRT
RDB1826
1
SARRPSGRKS SKMQAFRIWD VNQKTFYLRN NQLVAGYLQG
PNVNLEEKID VVPIEPHALF LGIHGGKMCL SCVKSGDETR
LQLEAVNITD LSENRKQDKR FAFIRSDSGP TTSFESAACP
GWFLCTAMEA DQPVSLTNMP DEGVMVTKFY FQEDEGGGGS
SESSASSDGP HPVITPSRAS ESSASSDGPH PVITPSRAGG
GGSSESSASS DGPHPVITPS RASESSASSD GPHPVITPSR
AGGGGSSESS ASSDGPHPVI TPSRASESSA SSDGPHPVIT
PSRAGGGGSD YKDDDDK

6)
DNA
RDB1826
1
TCCGCCAGGC GGCCTTCCGG CAGGAAAAGC AGCAAGATGC
AGGCCTTCCG GATCTGGGAC GTGAACCAGA AGACCTTCTA
CCTGCGGAAC AACCAGCTGG TGGCCGGCTA TCTGCAAGGC
CCCAACGTCA ACCTGGAGGA GAAGATCGAC GTCGTCCCTA
TCGAGCCTCA CGCCCTGTTC CTCGGCATCC ACGGCGGAAA
GATGTGCCTG AGCTGCGTGA AGTCCGGCGA CGAGACAAGG
CTCCAGCTCG AGGCCGTGAA TATCACCGAC CTGTCCGAGA
ACCGGAAGCA GGACAAGCGG TTCGCCTTCA TCAGGTCCGA
CAGCGGCCCT ACCACCTCCT TCGAATCCGC CGCTTGTCCT
GGCTGGTTTC TGTGTACCGC TATGGAGGCC GACCAGCCTG
TGTCCCTCAC CAACATGCCT GACGAGGGCG TGATGGTGAC
CAAGTTCTAC TTCCAGGAGG ACGAAGGAGG CGGCGGCTCC

-continued

AGCGAATCCA GCGCCTCCAG CGATGGCCCC CATCCTGTCA

TCACCCCTAG CAGGGCCTCC GAAAGCTCCG CCAGCAGCGA

TGGACCTCAT CCTGTCATTA CACCTAGCAG GGCTGGAGGA

GGAGGCAGCT CCGAGTCCAG CGCTAGCTCC GACGGACCCC

ACCCCGTGAT TACACCCTCC CGGGCTTCCG AGAGCAGCGC

TTCCAGCGAT GGACCTCATC CCGTGATCAC CCCTTCCAGG

GCTGGCGGAG GCGGCTCCAG CGAGAGCAGC GCCTCCAGCG

ACGGCCCCCA CCCTGTGATT ACACCTTCCC GGGCCAGCGA

GAGCTCCGCT AGCAGCGATG GACCCCATCC CGTGATCACA

CCCAGCAGGG CCGGAGGCGG AGGAAGCGAT TACAAGGACG

ACGACGACAA GTAGTGA

7)
PRT
RDB1815
1
SARRPSGRKS SKMQAFRIWD VNQKTFYLRN NQLVAGYLQG

PNVNLEEKID VVPIEPHALF LGIHGGKMCL SCVKSGDETR

LQLEAVNITD LSENRKQDKR FAFIRSDSGP TTSFESAACP

GWFLCTAMEA DQPVSLTNMP DEGVMVTKFY FQEDEGGGGS

ASSESSASSD GPHPVITESR ASSESSASSD GPHPVITESR

GGGGSASSES SASSDGPHPV ITESRASSES SASSDGPHPV

ITESRGGGGS ASSESSASSD GPHPVITESR ASSESSASSD

GPHPVITESR GGGGSASSES SASSDGPHPV ITESRASSES

SASSDGPHPV ITESRGSSHH HHHH

8)
DNA
RDB1815
1
TCCGCTCGAC GACCTTCTGG GCGAAAATCT TCTAAAATGC

AGGCCTTCCG GATTTGGGAT GTGAATCAGA AAACTTTTTA

CCTGAGGAAC AACCAGCTGG TCGCTGGATA CCTGCAGGGA

CCAAACGTGA ATCTGGAGGA GAAAATCGAC GTCGTCCCAA

TCGAACCTCA CGCTCTGTTT CTGGGAATCC ATGGCGGCAA

AATGTGTCTG TCCTGTGTGA ATCTGGCGA CGAGACTAGA

CTGCAGCTGG AGGCTGTGAA TATCACCGAC TGTCTGAGA

ATCGTAAACA GGACAAACGC TTTGCCTTTA TCCGCTCCGA

TAGTGGACCA CAACCTCTT TCGAATCTGC TGCTTGCCCT

GGATGGTTTC TGTGTACCGC TATGGAGGCC GATCAGCCTG

TGTCTCTGAC CAATATGCCC GATGAGGGAG TCATGGTGAC

AAAATTCTAC TTTCAGGAGG ATGAGGGCGG AGGCGGTTCT

GCTAGTAGCG AGTCCTCTGC TTCTTCCGAT GGACCTCACC

CCGTGATTAC CGAATCCCGA GCTTCTTCCG AATCTTCTGC

CTCTTCCGAC GGCCCACACC CTGTCATCAC TGAGAGCCGT

GGTGGCGGTG GATCTGCTAG TAGTGAATCA TCTGCTAGTA

GTGACGGCCC ACACCCCGTG ATTACTGAGA GTCGTGCCTC

TTCCGAATCA TCTGCTAGTA GTGACGGACC TCACCCCGTG

ATCACTGAGT CCCGTGGCGG TGGCGGTTCC GCTTCATCTG

AATCTTCCGC TTCATCCGAT GGTCCCCATC CTGTCATTAC

CGAATCTCGT GCCTCTAGCG AATCATCCGC TTCTAGTGAC

GGTCCCCACC CTGTCATTAC TGAATCCCGA GGCGGCGGTG

GATCTGCTTC TTCCGAATCA TCTGCTTCTA GTGACGGACC

ACACCCTGTC ATTACCGAGA GTAGGGCTTC ATCTGAATCT

TCCGCTTCAT CCGACGGACC ACATCCTGTG ATTACTGAAT

CACGAGGCTC ATCACACCAC CATCATCACC ACTAGTGA

9)
PRT
RDB1816
1
SARRPSGRKS SKMQAFRIWD VNQKTFYLRN NQLVAGYLQG

PNVNLEEKID VVPIEPHALF LGIHGGKMCL SCVKSGDETR

LQLEAVNITD LSENRKQDKR FAFIRSDSGP TTSFESAACP

GWFLCTAMEA DQPVSLTNMP DEGVMVTKFY FQEDEGGGGS

ASSESSASSD GPHPVITESR ASSESSASSD GPHPVITESR

GGGGSASSES SASSDGPHPV ITESRASSES SASSDGPHPV

ITESRGGGGS ASSESSASSD GPHPVITESR ASSESSASSD

GPHPVITESR GGGGSASSES SASSDGPHPV ITESRASSES

SASSDGPHPV ITESRGGGGS ASSESSASSD GPHPVITESR

ASSESSASSD GPHPVITESR GGGGSASSES SASSDGPHPV

ITESRASSES SASSDGPHPV ITESRGSSHH HHHH

10)
DNA
RDB1816
1
TCCGCTCGAC GACCTTCTGG GCGAAAATCT TCTAAAATGC

AGGCCTTCCG GATTTGGGAT GTGAATCAGA AAACTTTTTA

CCTGAGGAAC AACCAGCTGG TCGCTGGATA CCTGCAGGGA

CCAAACGTGA ATCTGGAGGA GAAAATCGAC GTCGTCCCAA

TCGAACCTCA CGCTCTGTTT CTGGGAATCC ATGGCGGCAA

AATGTGTCTG TCCTGTGTGA ATCTGGCGA CGAGACTAGA

CTGCAGCTGG AGGCTGTGAA TATCACCGAC TGTCTGAGA

ATCGTAAACA GGACAAACGC TTTGCCTTTA TCCGCTCCGA

TAGTGGACCA CAACCTCTT TCGAATCTGC TGCTTGCCCT

GGATGGTTTC TGTGTACCGC TATGGAGGCC GATCAGCCTG

TGTCTCTGAC CAATATGCCC GATGAGGGAG TCATGGTGAC

AAAATTCTAC TTTCAGGAGG ATGAGGGCGG AGGCGGTTCT

GCTAGTAGCG AGTCCTCTGC TTCTTCCGAT GGACCTCACC

CCGTGATTAC CGAATCCCGA GCTTCTTCCG AATCTTCTGC

CTCTTCCGAC GGCCCACACC CTGTCATCAC TGAGAGCCGT

GGTGGCGGTG GATCTGCTAG TAGTGAATCA TCTGCTAGTA

```
GTGACGGCCC ACACCCCGTG ATTACTGAGA GTCGTGCCTC

TTCCGAATCA TCTGCTAGTA GTGACGGACC TCACCCCGTG

ATCACTGAGT CCCGTGGCGG TGGCGGTTCC GCTTCATCTG

AATCTTCCGC TTCATCCGAT GGTCCCCATC CTGTCATTAC

CGAATCTCGT GCCTCTAGCG AATCATCCGC TTCTAGTGAC

GGTCCCCACC CTGTCATTAC TGAATCCCGA GGCGGCGGTG

GATCTGCTTC TTCCGAATCA TCTGCTTCTA GTGACGGACC

ACACCCTGTC ATTACCGAGA GTAGGGCTTC ATCTGAATCT

TCCGCTTCAT CCGACGGACC ACATCCTGTG ATTACTGAAT

CACGAGGCGG AGGAGGCTCC GCTTCTAGCG AATCATCTGC

CTCTAGTGAC GGTCCCCATC CCGTCATCAC TGAATCTCGA

GCATCATCTG AGTCATCTGC TTCTAGTGAC GGCCCACACC

CTGTGATTAC TGAGTCCCGG GGAGGCGGCG GTTCTGCCTC

TTCTGAATCC TCTGCTTCTT CCGATGGCCC ACACCCTGTC

ATTACCGAAT CCCGTGCTAG TAGTGAGTCA TCTGCCTCTA

GTGACGGACC TCACCCTGTG ATTACCGAAT CTCGAGGATC

ATCACACCAC CATCATCACC ACTAGTGA

11)
PRT
MUC1 tandem repeat unit (multiple variants)
1
PAPGSTAPPA HGVTSAPDTR

12)
PRT
MUC2 tandem repeat unit
1
ITTTTTVTPT PTPTGTQTPT TTP

13)
PRT
MUC3(A) tandem repeat unit (degenerate sequence)
1
ITTTETTSHD TPSFTSS

14)
PRT
MUC0 tandem repeat unit (degenerate sequence)
1
ATPLPVTDTS SASTGH

15)
PRT
MUC5AC tandem repeat unit
1
TTSTTSAP

16)
PRT
MUC5B tandem repeat unit (degenerate sequence)
1
ATGSTATPSS TPGTTHTPPV LTTTATTPT 17)
PRT
MUC7 tandem repeat unit (degenerate sequence)
1
TTAAPPTPSA TTQAPPSSSA PPE 18)
PRT
muc11/12 tandem repeat unit
1
EESTTVHSSP GATGTALFP 19)
PRT
MUC17 tandem repeat unit (degenerate sequence)
1
SSSPTPAEGT SMPTSTYSEG RTPLTSMPVS TTLVATSAI
STLSTTPVDT STPVTNSTEA 20)
PRT
MUC20 tandem repeat unit
1
SESSASSDGP HPVITPSRA 21)
PRT
MUC21 tandem repeat unit (degenerate sequence)
1
ATNSESSTVS SGIST 22)
PRT
TIM-1 tandem repeat unit (degenerate sequence)
1
VPTTTT 23)
PRT
PSGL-1 tandem repeat unit (degenerate sequence)
1
QTTQPAATEA 24)
PRT
RDB2203
1
HGEGTFTSDLSKQMEEEAVRLFIEWLKNGGPSSGAPPPSGGGGSASS
ESSASSDGPHPVITESRASSESSASSDGPHPVITESRGGGGSASSESSA
SSDGPHPVITESRASSESSASSDGPHPVITESRGGGGSASSESSASSD
GPHPVITESRASSESSASSDGPHPVITESRGGGGSASSESSASSD
GPHPVITESRASSESSASSDGPHPVITESRGGGGSHHHHHH
```

What is claimed is:

1. A fusion protein comprising a mucin-domain polypeptide linked to at least one active protein wherein the active protein is IL-1Ra and the fusion protein comprises amino acids 4-335 of SEQ ID NO: 7 or an amino acid sequence homologous thereto with at least 98% sequence identity over the full length of amino acids 4-335 at the amino acid level and wherein the half-life of the fusion protein is increased by two fold as compared to the half-life of the corresponding active protein that is not fused to the mucin-domain polypeptide.

2. The fusion protein of claim 1 wherein the apparent molecular weight of the fusion protein is higher than the calculated molecular weight of the active protein.

* * * * *

SEQUENCE LISTING

<160> NUMBER OF SEQ ID NOS: 28

<210> SEQ ID NO 1
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Ala Arg Arg Pro Ser Gly Arg Lys Ser Lys Met Gln Ala Phe
1               5                   10                  15

Arg Ile Trp Asp Val Asn Gln Lys Thr Phe Tyr Leu Arg Asn Asn Gln
            20                  25                  30

Leu Val Ala Gly Tyr Leu Gln Gly Pro Asn Val Asn Leu Glu Glu Lys
        35                  40                  45

Ile Asp Val Val Pro Ile Glu Pro His Ala Leu Phe Leu Gly Ile His
    50                  55                  60

Gly Gly Lys Met Cys Leu Ser Cys Val Lys Ser Gly Asp Glu Thr Arg
65                  70                  75                  80

Leu Gln Leu Glu Ala Val Asn Ile Thr Asp Leu Ser Glu Asn Arg Lys
                85                  90                  95

Gln Asp Lys Arg Phe Ala Phe Ile Arg Ser Asp Ser Gly Pro Thr Thr
            100                 105                 110

Ser Phe Glu Ser Ala Ala Cys Pro Gly Trp Phe Leu Cys Thr Ala Met
        115                 120                 125

Glu Ala Asp Gln Pro Val Ser Leu Thr Asn Met Pro Asp Glu Gly Val
130                 135                 140

Met Val Thr Lys Phe Tyr Phe Gln Glu Asp Glu Gly Gly Gly Gly Ser
145                 150                 155                 160

Ala Ser Ser Glu Ser Ser Ala Ser Ser Asp Gly Pro His Pro Val Ile
            165                 170                 175

Thr Glu Ser Arg Ala Ser Ser Glu Ser Ser Ala Ser Ser Asp Gly Pro
        180                 185                 190

His Pro Val Ile Thr Glu Ser Arg Gly Ser Ser His His His His His
        195                 200                 205

His

<210> SEQ ID NO 2
<211> LENGTH: 633
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
tccgctcgac gaccttctgg gcgaaaatct tctaaaatgc aggccttccg gatttgggat      60
gtgaatcaga aaactttta cctgaggaac aaccagctgg tcgctggata cctgcaggga     120
ccaaacgtga atctggagga gaaaatcgac gtcgtcccaa tcgaacctca cgctctgttt     180
ctgggaatcc atggcggcaa aatgtgtctg tcctgtgtga atctggcga cgagactaga     240
ctgcagctgg aggctgtgaa tatcaccgac ctgtctgaga tcgtaaaca ggacaaacgc      300
tttgccttta tccgctccga tagtggacca acaacctctt tcgaatctgc tgcttgccct     360
ggatggtttc tgtgtaccgc tatggaggcc gatcagcctg tgtctctgac caatatgccc     420
gatgagggag tcatggtgac aaaattctac tttcaggagg atgagggcgg aggcggttct     480
gctagtagcg agtcctctgc ttcttccgat ggacctcacc ccgtgattac cgaatcccga     540
gcttcttccg aatcttctgc ctcttccgac ggcccacacc ctgtcatcac tgagagccgt     600
ggttcatcac accaccatca tcaccactag tga                                  633
```

<210> SEQ ID NO 3
<211> LENGTH: 254

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ser Ala Arg Arg Pro Ser Gly Arg Lys Ser Ser Lys Met Gln Ala Phe
1               5                   10                  15

Arg Ile Trp Asp Val Asn Gln Lys Thr Phe Tyr Leu Arg Asn Asn Gln
            20                  25                  30

Leu Val Ala Gly Tyr Leu Gln Gly Pro Asn Val Asn Leu Glu Glu Lys
        35                  40                  45

Ile Asp Val Val Pro Ile Glu Pro His Ala Leu Phe Leu Gly Ile His
    50                  55                  60

Gly Gly Lys Met Cys Leu Ser Cys Val Lys Ser Gly Asp Glu Thr Arg
65                  70                  75                  80

Leu Gln Leu Glu Ala Val Asn Ile Thr Asp Leu Ser Glu Asn Arg Lys
                85                  90                  95

Gln Asp Lys Arg Phe Ala Phe Ile Arg Ser Asp Ser Gly Pro Thr Thr
            100                 105                 110

Ser Phe Glu Ser Ala Ala Cys Pro Gly Trp Phe Leu Cys Thr Ala Met
        115                 120                 125

Glu Ala Asp Gln Pro Val Ser Leu Thr Asn Met Pro Asp Glu Gly Val
    130                 135                 140

Met Val Thr Lys Phe Tyr Phe Gln Glu Asp Glu Gly Gly Gly Gly Ser
145                 150                 155                 160

Ala Ser Ser Glu Ser Ser Ala Ser Ser Asp Gly Pro His Pro Val Ile
                165                 170                 175

Thr Glu Ser Arg Ala Ser Ser Glu Ser Ser Ala Ser Ser Asp Gly Pro
            180                 185                 190

His Pro Val Ile Thr Glu Ser Arg Gly Gly Gly Ser Ala Ser Ser
        195                 200                 205

Glu Ser Ser Ala Ser Ser Asp Gly Pro His Pro Val Ile Thr Glu Ser
    210                 215                 220

Arg Ala Ser Ser Glu Ser Ser Ala Ser Ser Asp Gly Pro His Pro Val
225                 230                 235                 240

Ile Thr Glu Ser Arg Gly Ser Ser His His His His His His
                245                 250

<210> SEQ ID NO 4
<211> LENGTH: 768
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
tccgctcgac gaccttctgg gcgaaaatct tctaaaatgc aggccttccg gatttgggat      60
gtgaatcaga aaacttttta cctgaggaac aaccagctgg tcgctggata cctgcaggga     120
ccaaacgtga atctggagga gaaaatcgac gtcgtcccaa tcgaacctca cgctctgttt     180
ctgggaatcc atggcggcaa aatgtgtctg tcctgtgtga atctggcga cgagactaga      240 ctgcagctgg aggctgtgaa tatcaccgac ctgtctgaga tcgtaaaca ggacaaacgc      300 tttgccttta tccgctccga tagtggacca acaacctctt cgaatctgc tgcttgccct     360

```
ggatggtttc tgtgtaccgc tatggaggcc gatcagcctg tgtctctgac caatatgccc    420
gatgagggag tcatggtgac aaaattctac tttcaggagg atgagggcgg aggcggttct    480
gctagtagcg agtcctctgc ttcttccgat ggacctcacc ccgtgattac cgaatcccga    540
gcttcttccg aatcttctgc ctcttccgac ggcccacacc ctgtcatcac tgagagccgt    600
ggtggcggtg gatctgctag tagtgaatca tctgctagta gtgacggccc acaccccgtg    660
attactgaga gtcgtgcctc ttccgaatca tctgctagta gtgacggacc tcaccccgtg    720
atcactgagt cccgtggctc atcacaccac catcatcacc actagtga                768
```

<210> SEQ ID NO 5
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Ala Arg Arg Pro Ser Gly Arg Lys Ser Lys Met Gln Ala Phe
1               5                   10                  15

Arg Ile Trp Asp Val Asn Gln Lys Thr Phe Tyr Leu Arg Asn Asn Gln
            20                  25                  30

Leu Val Ala Gly Tyr Leu Gln Gly Pro Asn Val Asn Leu Glu Glu Lys
        35                  40                  45

Ile Asp Val Val Pro Ile Glu Pro His Ala Leu Phe Leu Gly Ile His
    50                  55                  60

Gly Gly Lys Met Cys Leu Ser Cys Val Lys Ser Gly Asp Glu Thr Arg
65                  70                  75                  80

Leu Gln Leu Glu Ala Val Asn Ile Thr Asp Leu Ser Glu Asn Arg Lys
                85                  90                  95

Gln Asp Lys Arg Phe Ala Phe Ile Arg Ser Asp Ser Gly Pro Thr Thr
            100                 105                 110

Ser Phe Glu Ser Ala Ala Cys Pro Gly Trp Phe Leu Cys Thr Ala Met
        115                 120                 125

Glu Ala Asp Gln Pro Val Ser Leu Thr Asn Met Pro Asp Glu Gly Val
    130                 135                 140

Met Val Thr Lys Phe Tyr Phe Gln Glu Asp Glu Gly Gly Gly Gly Ser
145                 150                 155                 160

Ser Glu Ser Ser Ala Ser Ser Asp Gly Pro His Pro Val Ile Thr Pro
                165                 170                 175

Ser Arg Ala Ser Glu Ser Ser Ala Ser Ser Asp Gly Pro His Pro Val
            180                 185                 190

Ile Thr Pro Ser Arg Ala Gly Gly Gly Ser Ser Glu Ser Ser Ala
        195                 200                 205

Ser Ser Asp Gly Pro His Pro Val Ile Thr Pro Ser Arg Ala Ser Glu
    210                 215                 220

Ser Ser Ala Ser Ser Asp Gly Pro His Pro Val Ile Thr Pro Ser Arg
225                 230                 235                 240

Ala Gly Gly Gly Gly Ser Ser Glu Ser Ser Ala Ser Ser Asp Gly Pro
                245                 250                 255

His Pro Val Ile Thr Pro Ser Arg Ala Ser Glu Ser Ser Ala Ser Ser
            260                 265                 270

Asp Gly Pro His Pro Val Ile Thr Pro Ser Arg Ala Gly Gly Gly Gly
        275                 280                 285

Ser Asp Tyr Lys Asp Asp Asp Lys
    290             295

<210> SEQ ID NO 6
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
tccgccaggc ggccttccgg caggaaaagc agcaagatgc aggccttccg gatctgggac      60
gtgaaccaga agaccttcta cctgcggaac aaccagctgg tggccggcta tctgcaaggc     120
cccaacgtca acctggagga gaagatcgac gtcgtccta tcgagcctca cgccctgttc      180
ctcggcatcc acggcggaaa gatgtgcctg agctgcgtga agtccggcga cgagacaagg     240
ctccagctcg aggccgtgaa tatcaccgac ctgtccgaga accggaagca ggacaagcgg     300
ttcgccttca tcaggtccga cagcggccct accacctcct tcgaatccgc cgcttgtcct     360
ggctggtttc tgtgtaccgc tatggaggcc gaccagcctg tgtccctcac caacatgcct     420
gacgagggcg tgatggtgac caagttctac ttccaggagg acgaaggagg cggcggctcc     480
agcgaatcca gcgcctccag cgatggcccc catcctgtca tcaccctag cagggcctcc     540
gaaagctccg ccagcagcga tggacctcat cctgtcatta cacctagcag ggctggagga     600
ggaggcagct ccgagtccag cgctagctcc gacggacccc accccgtgat tacaccctcc     660
cgggcttccg agagcagcgc ttccagcgat ggacctcatc ccgtgatcac cccttccagg     720
gctggcggag gcggctccag cgagagcagc gcctccagcg acggccccca ccctgtgatt     780
acaccttccc gggccagcga gagctccgct agcagcgatg accccatcc cgtgatcaca     840
cccagcaggg ccggaggcgg aggaagcgat tacaaggacg acgacgacaa gtagtga       897
```

<210> SEQ ID NO 7
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Ala Arg Arg Pro Ser Gly Arg Lys Ser Lys Met Gln Ala Phe
1               5                  10                  15

Arg Ile Trp Asp Val Asn Gln Lys Thr Phe Tyr Leu Arg Asn Asn Gln
            20                  25                  30

Leu Val Ala Gly Tyr Leu Gln Gly Pro Asn Val Asn Leu Glu Glu Lys
        35                  40                  45

Ile Asp Val Val Pro Ile Glu Pro His Ala Leu Phe Leu Gly Ile His
    50                  55                  60

Gly Gly Lys Met Cys Leu Ser Cys Val Lys Ser Gly Asp Glu Thr Arg
65                  70                  75                  80

Leu Gln Leu Glu Ala Val Asn Ile Thr Asp Leu Ser Glu Asn Arg Lys
                85                  90                  95

Gln Asp Lys Arg Phe Ala Phe Ile Arg Ser Asp Ser Gly Pro Thr Thr
            100                 105                 110

Ser Phe Glu Ser Ala Ala Cys Pro Gly Trp Phe Leu Cys Thr Ala Met
        115                 120                 125

-continued

```
Glu Ala Asp Gln Pro Val Ser Leu Thr Asn Met Pro Asp Glu Gly Val
130                 135                 140

Met Val Thr Lys Phe Tyr Phe Gln Glu Asp Glu Gly Gly Gly Gly Ser
145                 150                 155                 160

Ala Ser Ser Glu Ser Ser Ala Ser Ser Asp Gly Pro His Pro Val Ile
            165                 170                 175

Thr Glu Ser Arg Ala Ser Ser Glu Ser Ser Ala Ser Ser Asp Gly Pro
        180                 185                 190

His Pro Val Ile Thr Glu Ser Arg Gly Gly Gly Ser Ala Ser Ser
    195                 200                 205

Glu Ser Ser Ala Ser Ser Asp Gly Pro His Pro Val Ile Thr Glu Ser
210                 215                 220

Arg Ala Ser Ser Glu Ser Ser Ala Ser Ser Asp Gly Pro His Pro Val
225                 230                 235                 240

Ile Thr Glu Ser Arg Gly Gly Gly Ser Ala Ser Ser Glu Ser Ser
            245                 250                 255

Ala Ser Ser Asp Gly Pro His Pro Val Ile Thr Glu Ser Arg Ala Ser
            260                 265                 270

Ser Glu Ser Ser Ala Ser Ser Asp Gly Pro His Pro Val Ile Thr Glu
        275                 280                 285

Ser Arg Gly Gly Gly Ser Ala Ser Ser Glu Ser Ser Ala Ser Ser
290                 295                 300

Asp Gly Pro His Pro Val Ile Thr Glu Ser Arg Ala Ser Ser Glu Ser
305                 310                 315                 320

Ser Ala Ser Ser Asp Gly Pro His Pro Val Ile Thr Glu Ser Arg Gly
            325                 330                 335

Ser Ser His His His His His His
            340
```

<210> SEQ ID NO 8
<211> LENGTH: 1038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tccgctcgac gaccttctgg gcgaaaatct tctaaaatgc aggccttccg gatttgggat      60
gtgaatcaga aaacttttta cctgaggaac aaccagctgg tcgctggata cctgcaggga     120
ccaaacgtga atctggagga gaaaatcgac gtcgtcccaa tcgaacctca cgctctgttt     180
ctgggaatcc atggcggcaa aatgtgtctg tcctgtgtga atctggcga cgagactaga     240 ctgcagctgg aggctgtgaa tatcaccgac ctgtctgaga tcgtaaaca ggacaaacgc     300 tttgccttta tccgctccga tagtggacca caacctctt tcgaatctgc tgcttgccct     360
ggatggtttc tgtgtaccgc tatggaggcc gatcagcctg tgtctctgac caatatgccc     420
gatgagggag tcatggtgac aaaattctac tttcaggagg atgagggcgg aggcggttct     480
gctagtagcg agtcctctgc ttcttccgat ggacctcacc ccgtgattac cgaatcccga     540
gcttcttccg aatcttctgc ctcttccgac ggccacacc ctgtcatcac tgagagccgt     600
ggtggcggtg gatctgctag tagtgaatca tctgctagta gtgacggccc acaccccgtg     660
attactgaga gtcgtgcctc ttccgaatca tctgctagta gtgacggacc tcaccccgtg     720
atcactgagt cccgtggcgg tggcggttcc gcttcatctg aatcttccgc ttcatccgat     780
```

```
ggtccccatc ctgtcattac cgaatctcgt gcctctagcg aatcatccgc ttctagtgac    840
ggtccccacc ctgtcattac tgaatcccga ggcggcggtg atctgcttc ttccgaatca     900 tctgcttcta gtgacggacc acaccctgtc attaccgaga gtagggcttc atctgaatct    960
tccgcttcat ccgacggacc acatcctgtg attactgaat cacgaggctc atcacaccac   1020
catcatcacc actagtga                                                 1038
```

<210> SEQ ID NO 9
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Ser Ala Arg Arg Pro Ser Gly Arg Lys Ser Lys Met Gln Ala Phe
1               5                   10                  15

Arg Ile Trp Asp Val Asn Gln Lys Thr Phe Tyr Leu Arg Asn Asn Gln
            20                  25                  30

Leu Val Ala Gly Tyr Leu Gln Gly Pro Asn Val Asn Leu Glu Glu Lys
        35                  40                  45

Ile Asp Val Val Pro Ile Glu Pro His Ala Leu Phe Leu Gly Ile His
    50                  55                  60

Gly Gly Lys Met Cys Leu Ser Cys Val Lys Ser Gly Asp Glu Thr Arg
65                  70                  75                  80

Leu Gln Leu Glu Ala Val Asn Ile Thr Asp Leu Ser Glu Asn Arg Lys
                85                  90                  95

Gln Asp Lys Arg Phe Ala Phe Ile Arg Ser Asp Ser Gly Pro Thr Thr
            100                 105                 110

Ser Phe Glu Ser Ala Ala Cys Pro Gly Trp Phe Leu Cys Thr Ala Met
        115                 120                 125

Glu Ala Asp Gln Pro Val Ser Leu Thr Asn Met Pro Asp Glu Gly Val
    130                 135                 140

Met Val Thr Lys Phe Tyr Phe Gln Glu Asp Glu Gly Gly Gly Gly Ser
145                 150                 155                 160

Ala Ser Ser Glu Ser Ser Ala Ser Ser Asp Gly Pro His Pro Val Ile
                165                 170                 175

Thr Glu Ser Arg Ala Ser Ser Glu Ser Ser Ala Ser Ser Asp Gly Pro
            180                 185                 190

His Pro Val Ile Thr Glu Ser Arg Gly Gly Gly Ser Ala Ser Ser
        195                 200                 205

Glu Ser Ser Ala Ser Ser Asp Gly Pro His Pro Val Ile Thr Glu Ser
    210                 215                 220

Arg Ala Ser Ser Glu Ser Ser Ala Ser Ser Asp Gly Pro His Pro Val
225                 230                 235                 240

Ile Thr Glu Ser Arg Gly Gly Gly Ser Ala Ser Ser Glu Ser Ser
                245                 250                 255

Ala Ser Ser Asp Gly Pro His Pro Val Ile Thr Glu Ser Arg Ala Ser
            260                 265                 270

Ser Glu Ser Ser Ala Ser Ser Asp Gly Pro His Pro Val Ile Thr Glu
        275                 280                 285

Ser Arg Gly Gly Gly Ser Ala Ser Ser Glu Ser Ser Ala Ser Ser
    290                 295                 300

Asp Gly Pro His Pro Val Ile Thr Glu Ser Arg Ala Ser Ser Glu Ser
```

|       |       |       |       | 305   |       |       |       | 310   |       |       |       | 315   |       |       |       | 320   |
| ----- | ----- | ----- | ----- | ----- | ----- | ----- | ----- | ----- | ----- | ----- | ----- | ----- | ----- | ----- | ----- | ----- |

Ser Ala Ser Ser Asp Gly Pro His Pro Val Ile Thr Glu Ser Arg Gly
                325                 330                 335

Gly Gly Gly Ser Ala Ser Ser Glu Ser Ser Ala Ser Ser Asp Gly Pro
                340                 345                 350

His Pro Val Ile Thr Glu Ser Arg Ala Ser Ser Glu Ser Ser Ala Ser
                355                 360                 365

Ser Asp Gly Pro His Pro Val Ile Thr Glu Ser Arg Gly Gly Gly Gly
            370                 375                 380

Ser Ala Ser Ser Glu Ser Ser Ala Ser Ser Asp Gly Pro His Pro Val
385                 390                 395                 400

Ile Thr Glu Ser Arg Ala Ser Ser Glu Ser Ser Ala Ser Ser Asp Gly
                405                 410                 415

Pro His Pro Val Ile Thr Glu Ser Arg Gly Ser Ser His His His
                420                 425                 430

His His

<210> SEQ ID NO 10
<211> LENGTH: 1308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
tccgctcgac gaccttctgg gcgaaaatct tctaaaatgc aggccttccg gatttgggat      60
gtgaatcaga aaacttttta cctgaggaac aaccagctgg tcgctggata cctgcaggga     120
ccaaacgtga atctggagga gaaaatcgac gtcgtcccaa tcgaacctca cgctctgttt     180
ctgggaatcc atggcggcaa aatgtgtctg tcctgtgtga atctggcga cgagactaga     240 ctgcagctgg aggctgtgaa tatcaccgac ctgtctgaga tcgtaaaaca ggacaaacgc     300
tttgccttta tccgctccga tagtggacca acaacctctt tcgaatctgc tgcttgccct     360
ggatggtttc tgtgtaccgc tatggaggcc gatcagcctg tgtctctgac caatatgccc     420
gatgagggag tcatggtgac aaaattctac tttcaggagg atgagggcgg aggcggttct     480
gctagtagcg agtcctctgc ttcttccgat ggacctcacc ccgtgattac cgaatcccga     540
gcttcttccg aatcttctgc ctcttccgac ggcccacacc ctgtcatcac tgagagccgt     600
ggtggcggtg gatctgctag tagtgaatca tctgctagta gtgacggccc acaccccgtg     660
attactgaga gtcgtgcctc ttccgaatca tctgctagta gtgacggacc tcaccccgtg     720
atcactgagt cccgtggcgg tggcggttcc gcttcatctg aatcttccgc ttcatccgat     780
ggtccccatc ctgtcattac cgaatctcgt gcctctagcg aatcatccgc ttctagtgac     840
ggtccccacc ctgtcattac tgaatcccga ggcggcggtg gatctgcttc ttccgaatca     900
tctgcttcta gtgacggacc acaccctgtc attaccgaga gtaggcttc atctgaatct     960 tccgcttcat ccgacggacc acatcctgtg attactgaat cacgaggcgg aggaggctcc    1020
gcttctagcg aatcatctgc ctctagtgac ggtccccatc ccgtcatcac tgaatctcga    1080
gcatcatctg agtcatctgc ttctagtgac ggcccacacc ctgtgattac tgagtcccgg    1140
ggaggcggcg ttctgcctc ttctgaatcc tctgcttctt ccgatggccc acaccctgtc     1200
attaccgaat cccgtgctag tagtgagtca tctgcctcta gtgacggacc tcaccctgtg    1260
attaccgaat ctcgaggatc atcacaccac catcatcacc actagtga                 1308
```

<210> SEQ ID NO 11
<211> LENGTH: 20
<212> TYPE: PRT
<213> ORGANISM: Homo sapiens

<400> SEQUENCE: 11

Pro Ala Pro Gly Ser Thr Ala Pro Ala His Gly Val Thr Ser Ala
1               5                   10                  15

Pro Asp Thr Arg
            20

<210> SEQ ID NO 12
<211> LENGTH: 23
<212> TYPE: PRT
<213> ORGANISM: Homo sapiens

<400> SEQUENCE: 12

Ile Thr Thr Thr Thr Thr Val Thr Pro Thr Pro Thr Pro Thr Gly Thr
1               5                   10                  15

Gln Thr Pro Thr Thr Thr Pro
            20

<210> SEQ ID NO 13
<211> LENGTH: 17
<212> TYPE: PRT
<213> ORGANISM: Homo sapiens

<400> SEQUENCE: 13

Ile Thr Thr Thr Glu Thr Ser His Asp Thr Pro Ser Phe Thr Ser
1               5                   10                  15

Ser

<210> SEQ ID NO 14
<211> LENGTH: 16
<212> TYPE: PRT
<213> ORGANISM: Homo sapiens

<400> SEQUENCE: 14

Ala Thr Pro Leu Pro Val Thr Asp Thr Ser Ser Ala Ser Thr Gly His
1               5                   10                  15

<210> SEQ ID NO 15
<211> LENGTH: 8
<212> TYPE: PRT
<213> ORGANISM: Homo sapiens

<400> SEQUENCE: 15

Thr Thr Ser Thr Thr Ser Ala Pro
1               5

<210> SEQ ID NO 16
<211> LENGTH: 29
<212> TYPE: PRT
<213> ORGANISM: Homo sapiens

<400> SEQUENCE: 16

Ala Thr Gly Ser Thr Ala Thr Pro Ser Ser Thr Pro Gly Thr Thr His
1               5                   10                  15

Thr Pro Pro Val Leu Thr Thr Thr Ala Thr Thr Pro Thr
            20                  25

```
<210> SEQ ID NO 17
<211> LENGTH: 23
<212> TYPE: PRT
<213> ORGANISM: Homo sapiens

<400> SEQUENCE: 17

Thr Thr Ala Ala Pro Pro Thr Pro Ser Ala Thr Gln Ala Pro Pro
1               5                   10                  15

Ser Ser Ser Ala Pro Pro Glu
            20

<210> SEQ ID NO 18
<211> LENGTH: 19
<212> TYPE: PRT
<213> ORGANISM: Homo sapiens

<400> SEQUENCE: 18

Glu Glu Ser Thr Thr Val His Ser Ser Pro Gly Ala Thr Gly Thr Ala
1               5                   10                  15

Leu Phe Pro

<210> SEQ ID NO 19
<211> LENGTH: 59
<212> TYPE: PRT
<213> ORGANISM: Homo sapiens

<400> SEQUENCE: 19

Ser Ser Ser Pro Thr Pro Ala Glu Gly Thr Ser Met Pro Thr Ser Thr
1               5                   10                  15

Tyr Ser Glu Gly Arg Thr Pro Leu Thr Ser Met Pro Val Ser Thr Thr
            20                  25                  30

Leu Val Ala Thr Ser Ala Ile Ser Thr Leu Ser Thr Thr Pro Val Asp
        35                  40                  45

Thr Ser Thr Pro Val Thr Asn Ser Thr Glu Ala
    50                  55

<210> SEQ ID NO 20
<211> LENGTH: 19
<212> TYPE: PRT
<213> ORGANISM: Homo sapiens

<400> SEQUENCE: 20

Ser Glu Ser Ser Ala Ser Ser Asp Gly Pro His Pro Val Ile Thr Pro
1               5                   10                  15

Ser Arg Ala

<210> SEQ ID NO 21
<211> LENGTH: 15
<212> TYPE: PRT
<213> ORGANISM: Homo sapiens

<400> SEQUENCE: 21

Ala Thr Asn Ser Glu Ser Ser Thr Val Ser Ser Gly Ile Ser Thr
1               5                   10                  15

<210> SEQ ID NO 22
<211> LENGTH: 6
<212> TYPE: PRT
<213> ORGANISM: Homo sapiens

<400> SEQUENCE: 22

Val Pro Thr Thr Thr Thr
```

```
<210> SEQ ID NO 23
<211> LENGTH: 10
<212> TYPE: PRT
<213> ORGANISM: Homo sapiens

<400> SEQUENCE: 23

Gln Thr Thr Gln Pro Ala Ala Thr Glu Ala
1               5                   10

<210> SEQ ID NO 24
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Ala Ser Ser Glu
        35                  40                  45

Ser Ser Ala Ser Ser Asp Gly Pro His Pro Val Ile Thr Glu Ser Arg
50                  55                  60

Ala Ser Ser Glu Ser Ser Ala Ser Ser Asp Gly Pro His Pro Val Ile
65                  70                  75                  80

Thr Glu Ser Arg Gly Gly Gly Ser Ala Ser Ser Glu Ser Ser Ala
                85                  90                  95

Ser Ser Asp Gly Pro His Pro Val Ile Thr Glu Ser Arg Ala Ser Ser
            100                 105                 110

Glu Ser Ser Ala Ser Ser Asp Gly Pro His Pro Val Ile Thr Glu Ser
        115                 120                 125

Arg Gly Gly Gly Ser Ala Ser Ser Glu Ser Ser Ala Ser Ser Asp
130                 135                 140

Gly Pro His Pro Val Ile Thr Glu Ser Arg Ala Ser Ser Glu Ser Ser
145                 150                 155                 160

Ala Ser Ser Asp Gly Pro His Pro Val Ile Thr Glu Ser Arg Gly Gly
                165                 170                 175

Gly Gly Ser Ala Ser Ser Glu Ser Ser Ala Ser Ser Asp Gly Pro His
            180                 185                 190

Pro Val Ile Thr Glu Ser Arg Ala Ser Ser Glu Ser Ser Ala Ser Ser
        195                 200                 205

Asp Gly Pro His Pro Val Ile Thr Glu Ser Arg Gly Gly Gly Gly Ser
    210                 215                 220

His His His His His His
225                 230

<210> SEQ ID NO 25
<211> LENGTH: 19
<212> TYPE: PRT
<213> ORGANISM: Homo sapiens
<220> FEATURE:
<221> NAME/KEY: MOD_RES
<222> LOCATION: (4)..(6)
<223> OTHER INFORMATION: Any amino acid
<220> FEATURE:
```

-continued

```
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(18)
<223> OTHER INFORMATION: Any amino acid

<400> SEQUENCE: 25

Glu Glu Ser Xaa Xaa Xaa His Xaa Xaa Pro Xaa Xaa Thr Xaa Thr Xaa
1               5                   10                  15

Xaa Xaa Pro

<210> SEQ ID NO 26
<211> LENGTH: 10
<212> TYPE: PRT
<213> ORGANISM: Homo sapiens

<400> SEQUENCE: 26

Gly Val Thr Gly Thr Thr Gly Pro Ser Ala
1               5                   10

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Gly
1

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser
1               5
```